United States Patent
Vujanovic et al.

(10) Patent No.: US 11,064,673 B2
(45) Date of Patent: *Jul. 20, 2021

(54) ENDOPHYTIC MICROBIAL SYMBIONTS IN PLANT PRENATAL CARE

(71) Applicant: UNIVERSITY OF SASKATCHEWAN, Saskatoon (CA)

(72) Inventors: Vladimir Vujanovic, Saskatoon (CA); James J. Germida, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/228,640

(22) Filed: Dec. 20, 2018

(65) Prior Publication Data
US 2019/0320610 A1 Oct. 24, 2019

Related U.S. Application Data

(63) Continuation of application No. 14/766,065, filed as application No. PCT/CA2013/000091 on Feb. 5, 2013, now Pat. No. 10,212,912.

(51) Int. Cl.
| | | |
|---|---|---|
| *A01H 17/00* | (2006.01) | |
| *A01N 63/00* | (2020.01) | |
| *B09C 1/10* | (2006.01) | |
| *C12R 1/465* | (2006.01) | |
| *C12R 1/645* | (2006.01) | |
| *C12R 1/80* | (2006.01) | |
| *A01N 63/30* | (2020.01) | |
| *A01N 25/00* | (2006.01) | |

(52) U.S. Cl.
CPC ............ *A01H 17/00* (2013.01); *A01N 25/00* (2013.01); *A01N 63/00* (2013.01); *A01N 63/30* (2020.01); *B09C 1/105* (2013.01); *C12R 1/465* (2013.01); *C12R 1/645* (2013.01); *C12R 1/80* (2013.01)

(58) Field of Classification Search
CPC ...................................... A01H 17/00
See application file for complete search history.

(56) References Cited

U.S. PATENT DOCUMENTS

| | | |
|---|---|---|
| 2,200,532 A | 5/1940 | Sherman |
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 7/1993 | Nielsen et al. |
| 5,292,507 A | 3/1994 | Charley |
| 5,415,672 A | 5/1995 | Fahey et al. |
| 5,730,973 A | 3/1998 | Morales et al. |
| 5,919,447 A | 7/1999 | Marrone et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,602,500 B1 | 8/2003 | Kharbanda et al. |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |
| 7,084,331 B2 | 8/2006 | Isawa et al. |
| 7,335,816 B2 | 2/2008 | Kraus et al. |
| 7,341,868 B2 | 3/2008 | Chopade et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,143,045 B2 | 3/2012 | Miansnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Yandigeri et al Plant Growth Regul vol. 68, pp. 411-420 published Jun. 23, 2012 (Year: 2012).*

Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.

Abarenkov, K., et al., "The UNITE Database for Molecular Identification of Fungi—Recent Updates and Future Perspectives," New Phytol., 2010, pp. 281-285, vol. 186.

(Continued)

*Primary Examiner* — David H Kruse
(74) *Attorney, Agent, or Firm* — Goodwin Procter LLP

(57) ABSTRACT

The present disclosure provides novel endophyte strains or cultures thereof that have a symbiotic relationship with plants. The present disclosure further provides methods of improving seed vitality, biotic and abiotic stress resistance, plant health and yield under both stressed and unstressed environmental conditions, comprising inoculating a seed with the novel endophyte strains and cultivating a plant therefrom.

20 Claims, 42 Drawing Sheets

Specification includes a Sequence Listing.

(56) References Cited

U.S. PATENT DOCUMENTS

| | | | |
|---|---|---|---|
| 9,532,572 B2 | 1/2017 | von Maltzahn et al. | |
| 9,532,573 B2 | 1/2017 | von Maltzahn et al. | |
| 9,545,111 B2 | 1/2017 | Sword | |
| 9,622,485 B2 | 4/2017 | von Maltzahn et al. | |
| 9,652,840 B1 | 5/2017 | Shriver et al. | |
| 9,687,001 B2 | 6/2017 | Vujanovic et al. | |
| 9,756,865 B2 | 9/2017 | Sword | |
| 10,058,101 B2 | 8/2018 | von Maltzahn et al. | |
| 10,076,120 B2 | 9/2018 | von Maltzahn et al. | |
| 10,104,862 B2 * | 10/2018 | Vujanovic | A01N 25/00 |
| 10,136,646 B2 | 11/2018 | Von Maltzahn et al. | |
| 10,212,912 B2 * | 2/2019 | Vujanovic | A01N 63/10 |
| 10,306,890 B2 | 6/2019 | Mitter et al. | |
| 10,362,787 B2 | 7/2019 | Mitter et al. | |
| 10,499,652 B2 | 12/2019 | von Maltzahn et al. | |
| 10,499,653 B2 | 12/2019 | von Maltzahn et al. | |
| 10,499,654 B2 | 12/2019 | von Maltzahn et al. | |
| 2005/0070435 A1 | 3/2005 | Chopade et al. | |
| 2005/0072047 A1 | 4/2005 | Conkling et al. | |
| 2006/0046246 A1 | 3/2006 | Zeng et al. | |
| 2007/0028318 A1 | 2/2007 | Livore et al. | |
| 2007/0055456 A1 | 3/2007 | Raftery et al. | |
| 2007/0142226 A1 | 6/2007 | Franco | |
| 2007/0292953 A1 | 12/2007 | Mankin et al. | |
| 2008/0229441 A1 | 9/2008 | Young et al. | |
| 2008/0289060 A1 | 11/2008 | De Beuckeleer et al. | |
| 2009/0155214 A1 | 6/2009 | Isawa et al. | |
| 2010/0064392 A1 | 3/2010 | Yang et al. | |
| 2010/0095396 A1 | 4/2010 | Voeste et al. | |
| 2010/0205690 A1 | 8/2010 | Blasing et al. | |
| 2010/0227357 A1 | 9/2010 | Redman et al. | |
| 2011/0182862 A1 | 7/2011 | Green et al. | |
| 2012/0108431 A1 | 5/2012 | Williams et al. | |
| 2012/0131696 A1 | 5/2012 | Aayal et al. | |
| 2012/0144533 A1 | 6/2012 | Craven | |
| 2012/0149571 A1 | 6/2012 | Kloepper et al. | |
| 2012/0178624 A1 | 7/2012 | Kaminskyj et al. | |
| 2012/0324599 A1 | 12/2012 | Kerns et al. | |
| 2013/0031673 A1 | 1/2013 | Grandlic et al. | |
| 2013/0071425 A1 | 3/2013 | Vidal et al. | |
| 2013/0079225 A1 | 3/2013 | Smith et al. | |
| 2013/0150240 A1 | 6/2013 | Newman et al. | |
| 2013/0233501 A1 | 9/2013 | Van Zyl et al. | |
| 2014/0020136 A1 | 1/2014 | Van Der Wolf et al. | |
| 2014/0109249 A1 | 4/2014 | Turner et al. | |
| 2014/0115731 A1 | 4/2014 | Turner et al. | |
| 2014/0147425 A1 | 5/2014 | Henn et al. | |
| 2014/0342905 A1 | 11/2014 | Bullis et al. | |
| 2015/0020239 A1 | 1/2015 | von Maltzahn et al. | |
| 2015/0033420 A1 | 1/2015 | Rodriguez et al. | |
| 2015/0126365 A1 | 5/2015 | Sword | |
| 2015/0230478 A1 | 8/2015 | Vujanovic et al. | |
| 2015/0242970 A1 | 8/2015 | Avey et al. | |
| 2015/0335029 A1 | 11/2015 | Mitter et al. | |
| 2015/0366217 A1 | 12/2015 | Vujanovic et al. | |
| 2015/0368607 A1 | 12/2015 | Arnold et al. | |
| 2015/0370935 A1 | 12/2015 | Starr | |
| 2015/0373993 A1 | 12/2015 | von Maltzahn et al. | |
| 2016/0021891 A1 | 1/2016 | von Maltzahn et al. | |
| 2016/0150796 A1 | 6/2016 | von Maltzahn et al. | |
| 2016/0174570 A1 | 6/2016 | Vujanovic et al. | |
| 2016/0192662 A1 | 7/2016 | Sword | |
| 2016/0205947 A1 | 7/2016 | Sword | |
| 2016/0235074 A1 | 8/2016 | von Maltzahn et al. | |
| 2016/0255844 A1 | 9/2016 | Mitter et al. | |
| 2016/0260021 A1 | 9/2016 | Marek | |
| 2016/0286821 A1 | 10/2016 | Sword | |
| 2016/0290918 A1 | 10/2016 | Xu et al. | |
| 2016/0316760 A1 | 11/2016 | Ambrose et al. | |
| 2016/0316763 A1 | 11/2016 | Sword | |
| 2016/0330976 A1 | 11/2016 | Mitter et al. | |
| 2016/0338360 A1 | 11/2016 | Mitter et al. | |
| 2016/0366892 A1 | 12/2016 | Ambrose et al. | |
| 2017/0020138 A1 | 1/2017 | von Maltzahn et al. | |
| 2017/0164619 A1 | 6/2017 | von Maltzahn et al. | |
| 2017/0164620 A1 | 6/2017 | von Maltzahn et al. | |
| 2017/0215358 A1 | 8/2017 | Franco et al. | |
| 2017/0223967 A1 | 8/2017 | Mitter et al. | |
| 2018/0020677 A1 | 1/2018 | Ambrose et al. | |
| 2018/0092365 A1 | 4/2018 | Sword | |
| 2018/0153174 A1 | 6/2018 | Riley et al. | |
| 2018/0177196 A1 | 6/2018 | Sword | |
| 2018/0213800 A1 | 8/2018 | Djonovic et al. | |
| 2018/0249716 A1 | 9/2018 | Riley | |
| 2018/0251776 A1 | 9/2018 | Riley | |

FOREIGN PATENT DOCUMENTS

| | | |
|---|---|---|
| CA | 2562175 | 1/2013 |
| CA | 2916678 A1 | 12/2014 |
| CA | 2960032 A1 | 3/2015 |
| CA | 2935218 A1 | 7/2015 |
| CA | 2953466 A1 | 12/2015 |
| CA | 2953697 A1 | 12/2015 |
| CN | 1604732 | 4/2005 |
| CN | 1948459 A | 4/2007 |
| CN | 101311262 A | 11/2008 |
| CN | 101423810 A | 5/2009 |
| CN | 101570738 | 11/2009 |
| CN | 101693881 A | 4/2010 |
| CN | 102123596 A | 7/2011 |
| CN | 102168022 A | 8/2011 |
| CN | 102352327 A | 2/2012 |
| CN | 102010835 B | 4/2012 |
| CN | 102533601 B | 10/2013 |
| CN | 103642725 A | 3/2014 |
| CN | 104250616 A | 12/2014 |
| CN | 104388356 A | 3/2015 |
| CN | 104560742 A | 4/2015 |
| EP | 0192342 | 8/1986 |
| EP | 0223662 | 5/1987 |
| EP | 0378000 | 7/1990 |
| EP | 0494802 | 7/1992 |
| EP | 0818135 | 1/1998 |
| EP | 1621632 A1 | 2/2006 |
| EP | 1935245 | 6/2008 |
| EP | 2676536 | 12/2013 |
| JP | 2003300804 A | 10/2003 |
| JP | 2009/072168 | 4/2009 |
| KR | 20100114806 | 10/2010 |
| KR | 101066283 | 9/2011 |
| KR | 101091151 | 12/2011 |
| KR | 20130023491 A | 3/2013 |
| RU | 2043028 C1 | 9/1995 |
| WO | WO 1988/009114 | 1/1988 |
| WO | WO 1994/016076 | 7/1994 |
| WO | WO 2000/029607 | 5/2000 |
| WO | 2001/083697 A2 | 11/2001 |
| WO | WO 2001/083818 | 11/2001 |
| WO | WO 2002/065836 | 8/2002 |
| WO | 2004/046357 A1 | 6/2004 |
| WO | WO 2005/003328 | 1/2005 |
| WO | WO 2007/021200 | 2/2007 |
| WO | WO 2007/107000 | 9/2007 |
| WO | WO 2008/103422 | 8/2008 |
| WO | WO 2009/012480 | 1/2009 |
| WO | WO 2009/078710 | 6/2009 |
| WO | WO 2009/126473 | 10/2009 |
| WO | WO 2010/109436 | 9/2010 |
| WO | WO 2010/115156 | 10/2010 |
| WO | 2011/011627 A1 | 1/2011 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | WO 2012/034996 | 3/2012 |
| WO | WO 2013/016361 | 1/2013 |
| WO | WO 2013/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |

(56) References Cited

FOREIGN PATENT DOCUMENTS

| WO | WO 2014/121366 | 8/2014 |
|---|---|---|
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |
| WO | 2015/192172 A1 | 12/2015 |
| WO | WO 2015/200852 | 12/2015 |
| WO | WO 2015/200902 | 12/2015 |
| WO | 2016/057991 A1 | 4/2016 |
| WO | 2016/090212 A1 | 6/2016 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |
| WO | 2018102733 A1 | 6/2018 |
| WO | 2018160244 A1 | 9/2018 |
| WO | 2018160245 A1 | 9/2018 |

OTHER PUBLICATIONS

Abdellatif, L., et al., "Endophytic hyphal compartmentalization is required for successful symbiotic Ascomycota association with root cells," Mycological Research, 2009, pp. 782-791, vol. 113.

Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.

Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.

Abou-Shanab, R. A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.

Adhikari, M., et al., "A New Record of Pseudeurotium bakeri from Crop Field Soil in Korea," The Korean Journal of Mycology, 2016, pp. 145-149, vol. 44.

Ahmad, F., et al., "Screening of Free-Living Rhizospheric Bacteria for Their Multiple Plant Growth Promoting Activities," Microbiol Res., 2008, pp. 173-181, vol. 163.

Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.

Amann, R., et al., "The Identification of Microorganisms by Fluorescence in Situ Hybridisation," Curr Opin Biotechnol., 2001, pp. 231-236, vol. 12.

Amatuzzi, R.F., et al., "Univers1dade Federal Do Parana," Jan. 1, 2014, 52 Pages. (With English Abstract).

Amatuzzi, R.F., et al., "Potential of endophytic fungi as biocontrol agents of Duponchelia fovealis (Zeller) (Lepidoptera:Crambidae)," Brazilian Journal of Biology, Nov. 9, 2017, 7 Pages.

Apel, K., et al., "Reactive Oxygen Species: Metabolism, Oxidative Stress, and Signal Transduction," Annu Rev Plant Biol., 2004, pp. 373-399, vol. 55.

Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.

Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.

Aveskamp, M., et al., "DNA phylogeny reveals polyphyly of Phoma section Peyronellaea and multiple taxonomic novelties," Mycologia, 2009, vol. 101, No. 3, pp. 363-382.

Bacon, C. W., et al., "Isolation, in Planta Detection, and Uses of Endophytic Bacteria for Plant Protection," Manual of Environmental Microbiology, 2007, pp. 638-647.

Baker, K. F., et al., "Dynamics of Seed Transmission of Plant Pathogens," Annu Rev Phytopathol., 1966, pp. 311-334, vol. 4.

Baltruschat, H., et al., "Salt tolerance of barley induced by the root endophyte *Piriformospora indica* is associated with a strong increase in antioxidants," New Phytologist., 2008, pp. 501-510, vol. 180.

Bensch, K., et al., "Species and ecological diversity within the Cladosporium cladosporioides complex (Davidiellaceae, Capnodiales)," Studies in Mycology, 2010, pp. 1-94, vol. 67.

Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.

Bing, La, et al., "Suppression of Ostrinia nubilalis (Hubner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.

Block, C. C., et al., "Seed Transmission of Pantoea stewartii in Field and Sweet Corn," Plant Disease, 1998, pp. 775-780, vol. 82.

Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.

Brodie, E.L., et al., "Uncultured Bacterium Clone BANW722 16S Ribosomal RNA Gene, Partial Sequence," NCBI GenBank Accession No. DQ264636, Submitted Oct. 25, 2005.

Bulgarelli, D., et al., "Structure and Functions of the Bacterial Microbiota of Plants," Annu Rev Plant Biol., 2013, pp. 807-838, vol. 64.

Buttner, D., et al., "Regulation and secretion of Xanthomonas virulence factors," FEMS Microbiology Reviews, 2010, pp. 107-133, vol. 34, No. 2.

Caporaso, J.G., et al., "Ultra-High-Throughput Microbial Community Analysis on the Illumina HiSeq and MiSeq Platforms," ISME J., 2012, pp. 1621-1624, vol. 6.

Castillo, D., et al., "Fungal Entomopathogenic Endophytes: Negative Effects on Cotton Aphid Reproduction in Greenhouse and Field Conditions," Power Point Presentation dated Mar. 23, 2013.

Castillo, D., et al., "Fungal Endophytes: Plant Protective Agents Against Herbivores," Power Point Presentation dated Aug. 4, 2013.

Cavalier-Smith, T., "A Revised Six-Kingdom System of Life," Biol Rev Camb Philos Soc., 1998, pp. 203-266, vol. 73.

Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.

Chagas, F., et al., "A Mixed Culture of Endophytic Fungi Increases Production of Antifungal Polyketides," J. Chem Ecol., Oct. 2013, pp. 1335-1342, vol. 39.

Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.

Clark, E. M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.

Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.

Clay, K., "Effects of fungal endophytes on the seed and seedling biology of Lolium perenne and Festuca arundinacea," Oecologia, 1987, pp. 358-362, vol. 73.

Clough, S. J., et al., "Floral Dip: A Simplified Method for Agrobacterium-mediated Transformation of *Arabidopsis thaliana*," Plant J., 1998, pp. 735-743, vol. 16, No. 6.

Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.

Compant, S., et al., "Endophytic colonization of Vitis vinfera L. by Burkholderia phytofirmans strain PsJN: from the rhizosphere to inflorescence tissues," FEMS Microbiol Ecol, 2008, pp. 84-93, vol. 63.

(56) References Cited

OTHER PUBLICATIONS

Coombs, J. T., et al., "Isolation and Identification of Actinobacteria from Surface-Sterilized Wheat Roots," Applied and Environmental Microbiology, 2003, pp. 5603-5608, vol. 69, No. 9.

Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.

Cottyn, B., et al., "Phenotypic and genetic diversity of rice seed-associated bacteria and their role in pathogenicity and biological control," Journal of Applied Microbiology, 2009, pp. 885-897, vol. 107.

Cox, C. D., "Deferration of Laboratory Media and Assays for Ferric and Ferrous Ions," Methods Enzymol., 1994, pp. 315-329, vol. 235.

Craine, J. M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.

DBGET, "Orthology: K14454," 2005, 2 pages, can be retrieved at <URL:http://www.genome.jp/dbget-bin/www_bget?ko:K14454>.

De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Djordjevic, D., et al., "Microtiter Plate Assay for Assessment of Listeria monocytogenes Biofilm Formation," Annl Environ Microbiol., 2002, pp. 2950-2958, vol. 68, No. 6.

Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 1 Page.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than Blast," Bioinformatics, 2010, pp. 2460-2461, vol. 26, No. 19.

Edgar, R. C., "UPARSE: Highly Accurate OTU Sequences From Microbial Amplicon Reads," Nat Methods, 2013, pp. 996-998, vol. 10, No. 10.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013, 18 Pages.

El-Shanshoury, A. R., "Growth Promotion of Wheat Seedlings by Streptomyces atroolivaceus," Journal of Agronomy and Crop Science, 1989, pp. 109-114, vol. 163.

Emerson, D., et al., Identifying and Characterizing Bacteria in an Era of Genomics and Proteomics, BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

Faria, D. C., et al., "Endophytic Bacteria Isolated from Orchid and Their Potential to Promote Plant Growth," World J Microbiol Biotechnol., 2013, pp. 217-221, vol. 29.

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161, vol. 8.

Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.

Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.

Fisher, P. J., et al., "Fungal saprobes and pathogens as endophytes of rice (*Oryza sativa* L.)," New Phytol., 1992, pp. 137-143, vol. 120.

Fisher, P. R., et al., "Isolation and Characterization of the Pesticide-Degrading Plasmid pJP1 from Alcaligenes paradoxus," J Bacteriol., 1978, pp. 798-804, vol. 135, No. 3.

Franco, C., et al., "Actinobacterial Endophytes for Improved Crop Performance," Australasian Plant Pathology, 2007, pp. 524-531, vol. 36.

Fulthorpe, R. R., et al., "Distantly Sampled Soils Carry Few Species in Common," ISME J., 2008, pp. 901-910, vol. 2.

Gantner, S., et al., "Novel Primers for 16S rRNA-based Archaeal Community Analyses in Environmental Samples," J Microbiol Methods, 2011, pp. 12-18, vol. 84.

Gao, Z., et al., "Quantitation of Major Human Cutaneous Bacterial and Fungal Populations," J Clin Microbiol., 2010, pp. 3575-3581, vol. 48, No. 10.

Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.

Gasser, I., et al., "Ecology and Characterization of Polyhydroxyalkanoate-Producing Microorganisms on and in Plants," FEMS Microbiol Ecol., 2010, pp. 142-150, vol. 70.

Gavrish, E, et al., "*Lentzea* sp. MS6 16S Ribosomal RNA Gene, Partial Sequence," NCBI GenBank Accession No. EF599958. Submitted May 9, 2007, 1 Page.

Gebhardt, J., et al., "Characterization of a single soybean cDNA encoding cytosolic and glyoxysomal isozymes of aspartate aminostransferase," Plant Molecular Biology, 1998, pp. 99-108, vol. 37.

GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI,

(56) References Cited

OTHER PUBLICATIONS

May 26, 1998, 2 Pages, can be retrieved at <URL:https://www.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "aspartate aminotransferase glyoxysomal isozyme AAT1 precursor [*Glycine max*]," NCBI, Oct. 29, 2016, 2 Pages, can be retrieved at <URL:https://www.ncbi.nlm.nih.gov/protein/NP_001237541.1>.
NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 2 Pages.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, SEQ ID 1." Aug. 15, 2013, 1 Page.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession No. AY016368 sequence.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of Sarocladium (Hypocreales)," Persoonia, 2015, pp. 10-24, vol. 34.
Gitaitis, R., et al., "The Epidemiology and Management of Seedborne Bacterial Diseases," Annu Rev Phytopathol., 2007, pp. 371-397, vol. 45.
Grondona, I., et al., "TUSAL®, a commercial biocontrol formulation based on Trichoderma," Bulletin OILB/SROP, 2004, pp. 285-288, vol. 27, No. 8.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallmann, J., et al., "Bacterial Endophytes in Agricultural Crops," Canadian J Microbiol., 1997, pp. 895-914, vol. 43.
Hamayun, M., et al., "Cladosporium sphaerospermum as a new plant growth-promoting endophyte from the roots of *Glycine max* (L.) Merr," World Journal of Microbiology and Biotechnology, Kluwer Academic Publishers, Feb. 15, 2009, pp. 627-632, vol. 25, No. 4.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, L.E., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P. R., et al., "Dynamics of Seed-Borne Rice Endophytes on Early Plant Growth Stages," PLoS ONE, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., 2011. "Agricultural Potential of Fungal Endophytes of Grasses, Cereals and Wheat," in: Wheat: Genetics, Crops and Food Production. Nova Science Publishers Hauppauge, NY, USA. pp. 333-345.

(56) References Cited

OTHER PUBLICATIONS

Hubbard, M., et al., "Fungal Endophytes Improve Wheat Seed Germination Under Heat and Drought Stress," Botany, 2012, pp. 137-149, vol. 90.

Humann, J., et al., "Complete genome of the onion pathogen Enterobacter cloacae EcWSU1," Standard in Genomic Sciences, Dec. 31, 2011, vol. 5, No. 3, pp. 279-286.

Hung, P.Q., et al., "Isolation and Characterization of Endophytic Bacteria in Soybean (*Glycine* Sp.)," Omonrice, 2004, pp. 92-101, vol. 12.

Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.

Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.

Imoto, K., et al., "Comprehensive Approach to Genes Involved in Cell Wall Modifications in *Arabidopsis thaliana*," Plant Mol Biol., 2005, pp. 177-192, vol. 58.

Impullitti, A.E., et al., "Fungal endophyte diversity in soybean", Journal of Applied Microbiolog, vol. 114, No. 5, May 1, 2013, pp. 1500-1506.

Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.

Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.

Johnston-Monje, D., et al., "Conservation and Diversity of Seed Associated Endophytes in Zea Across Boundaries of Evolution, Ethnography and Ecology," PLOS ONE, vol. 6, No. 6, Jun. 3, 2011, p. e20396, 22 Pages.

Johnston-Monje, D., et al., "Plant and Endophyte Relationships: Nutrient Management," Comprehensive Biotechnol., 2011, pp. 713-727, vol. 4.

Johnston-Monje, D., "Microbial Ecology of Endophytic Bacteria in Zea Species as Influenced by Plant Genotype, Seed Origin, and Soil Environment," Thesis, University of Guelph, 2011, 230 Pages.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Jung, C., et al., "The Effects of Endohyphal Bacteria on Anti-Cancer and Anti-Malaria Metabolites of Endophytic Fungi," Honors Thesis, University of Arizona, May 2012, 15 Pages.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Point Presentation dated Jan. 7, 2013.

Kang, B. H., et al., "Members of the Arabidopsis Dynamin-Like Gene Family, ADL1, are Essential for Plant Cytokinesis and Polarized Cell Growth," Plant Cell, 2003, pp. 899-913, vol. 15.

Kasana, R. C., et al., "A Rapid and Easy Method for the Detection of Microbial Cellulases on Agar Plates Using Gram's Iodine," Curr Microbiol., 2008, pp. 503-507, vol. 57.

Khan, A.L., et al., "Salinity Stress Resistance Offered by Endophytic Fungal Interaction Between Penicillium miniloluteum LHL09 and Glycine max. L," J. Microbiol. Biotechnol., 2011, pp. 893-902, vol. 21, No. 9.

Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.

Klaubauf, S., et al., "Molecular diversity of fungal communities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.

Kruger, M., et al., "DNA-Based Species Level Detection of Glomeromycota: One PCR Primer Set for All Arbuscular Mycorrhizal Fungi," New Phytol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.

Kumar, A., et al., "Bio-control potential of *Cladosporium* sp. (MCPL-461), against a noxious weed Parthenium hysterophorus L.," J. Environ Biol., Mar. 2009, pp. 307-312, vol. 30, Issue 2.

Kusari, S., et al. "Chemical ecology of endophytic fungi: origins of secondary metabolites," Cell Press, Chem & Biol., 2012, pp. 792-798, vol. 19.

Labeda, D.P., et al., "Phylogenetic study of the species within the family Streptomycetaceae," Antonie van Leeuwenhoek, 2012, vol. 101, pp. 73-104, Springer.

Lanver, D., et al., "Sho1 and Msb2-Related Proteins Regulate Appressorium Development in the Smut Fungus Ustilago aydis," Plant Cell, 2010, pp. 2085-2101, vol. 22.

Laus, M. C., et al., "Role of Cellulose Fibrils and Exopolysaccharides of Rhizobium leguminosarum in Attachment to and Infection of Vicia sativa Root Hairs," Mol Plant Microbe Interact., 2005, pp. 533-538, vol. 18, No. 6.

Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.

Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lehman, S.G., "Treat Cotton Seed," Review of Applied Mycology, 1945, 24, 369, 16 Pages.

Lehman, S.G., "Treat Cotton Seed," Research and Farming III, Progr. Rept., 1945, 3, 5, 16 Pages.

Leonard, C. A., et al., "Random Mutagenesis of the Aspergillus oryzae Genome Results in Fungal Antibacterial Activity," Int J Microbiol., 2013, vol. 2013, Article ID 901697, 6 Pages.

Li, H. M., et al., "Expression of a Novel Chitinase by the Fungal Endophyte in Poa ampla," Mycologia, 2004, pp. 526-536, vol. 96, No. 3.

Li, H., et al., "Endophytes and their role in phytoremediation," Fungal Diversity, 2012, pp. 11-18, vol. 54.

Li, Q., "Agrobacterium tumefaciens Strain TA-AT-10 16S Ribosomal RNA Gene, Partial Sequence: GenBank: KF673157.1," Submitted Sep. 17, 2013.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Phylogenetic relationships among ascomycetes: evidence from an RNA polymerase II subunit," Mol. Biol. Evol. 1999. vol. 16, No. 12, pp. 1799-1808.

(56) References Cited

OTHER PUBLICATIONS

Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mandyam, K., et al., "Mutualism-parasitism paradigm synthesized from results of root-endophyte models", Frontiers in Microbiology, Jan. 12, 2015, pp. 1-14, vol. 5.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.

Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol of chickpea root rot using endophytic actinobacteria", Biocontrol, vol. 56, No. 5, Mar. 12, 2011, pp. 811-822, XP036215297.
Miyoshi-Akiyama, T., et al., "Multilocus Sequence Typing (MLST) for Characterization of Enterobacter cloacae," PLoS ONE, 2013, vol. 8, No. 6, 10 Pages, e66358.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: an Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Nassar, A., et al., "Promotion of plant growth by an auxin-producing isolate of the yeast Williopsis saturnus endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato, " Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
O'Hanlon, K., et al., "Exploring the potential of symbiotic fungal endophytes in cereal disease suppression", Biological Control, vol. 63, No. 2, Sep. 5, 2012, pp. 69-78.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orole, O. O., et al., "Bacterial and fungal endophytes associated with grains and roots of maize," Journal of Ecology and the Natural Enviornment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.

(56) References Cited

OTHER PUBLICATIONS

Pearson, W.R., et al., "Rapid and Sensitive Sequence Comparison With FASTP and FASTA," Methods Enzymol., 2011, pp. 63-98, vol. 183.

Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.

Perez-Fernandez, M. A., et al., "Simulation of Germination of Pioneer Species Along an Experimental Drought Gradient," J Environ Biol., 2006, pp. 669-685, vol. 27, No. 4.

Perez-Miranda, S., et al., "O-CAS, A Fast and Universal Method for Siderophore Detection," J Microbiol Methods, 2007, pp. 127-131, vol. 70.

Petti, C. A., "Detection and Identification of Microorganisms by Gene Amplification and Sequencing," Clinical Infectious Diseases, 2007, pp. 1108-1114, vol. 44.

Phalip, V., et al., "A Method for Screening Diacetyl and Acetoin-Producing Bacteria on Agar Plates," J Basic Microbiol., 1994, pp. 277-280, vol. 34.

Philippot, L., et al., "Going Back to the Roots: The Microbial Ecology of the Rhizosphere," Nat Rev Microbiol., Nov. 2013, pp. 789-799, vol. 11.

Philrice Batac, Philippine Rice R&D Highlights, 2012, Area-Based R&D Projects, 52 Pages, [online][Retrieved Aug. 11, 2016] Retrieved from the Internet <URL:http://www.philrice.gov.ph/2012-rd-highlights/>.

Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.

Powell, W. A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.

Quadt-Hallmann, A., et al., "Bacterial Endophytes in Cotton: Mechanisms of Entering the Plant," Can J Microbiol., 1997, pp. 577-582, vol. 43.

R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.

Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.

Rasmussen, S., et al., "Grass-endophyte interactions: a note on the role of monosaccharide transport in the Neotyphodium Iolii-Lolium perenne symbiosis," New Phytologist, 2012, pp. 7-12, vol. 196.

Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.

Redman, R. S., et al., "Thermotolerance Generated by Plant/Fungal Symbiosis," Science, Nov. 2002, vol. 298, 1 Page (with 4 pages of supplemental material).

Reiter, B., et al., "Response of Endophytic Bacterial Communities in Potato Plants to Infection with *Erwinia carotovora* subsp. atroseptica," Appl Environ Microbiol., 2001, pp. 2261-2268, vol. 68, No. 5.

Ren, Y., et al., "Complete Genome Sequence of *Enterobacter cloacae* subsp. cloacae Type Strain ATCC 13047," J. Bacteriol. May 2010, vol. 192, No. 9, pp. 2463-2464.

Riess, K., et al., "High genetic diversity at the regional scale and possible speciation in Sebacina epigaea and S. incrustans," BMC Evolutionary Biology, 2013, vol. 13, No. 102, 17 Pages.

Riken, GI No. GMFL01-01-003, 2 Pages, [online] [Retrieved on Dec. 18, 2017] Retrieved from the internet <URL:http://spectra.psc.riken.jp/menta.cgi/rsoy/datail?id=GMFL01-01-D03>.

Rodriguez, H., et al., "Expression of a Mineral Phosphate Solubilizing Gene From Erwinia herbicola in Two Rhizobacterial Strains," J Biotechnol., 2001, pp. 155-161, vol. 84.

Rodriguez, R.J., et al., "Stress Tolerance in Plants via Habitat-Adapted Symbiosis," ISME J., 2008, pp. 404-416, vol. 2.

Rodriguez-Navarro, D., et al., "Soybean Interactions with Soil Microbes, Agronomical and Molecular Aspects," Agronomy for Sustainable Development, 2011, pp. 173-190, vol. 31, No. 1.

Roessner, U., et al., "Metabolic Profiling Allows Comprehensive Phenotyping of Genetically or Environmentally Modified Plant Systems," Plant Cell, 2001,pp. 11-29, vol. 13.

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.

Rosenblueth, A., et al., "Seed Bacterial Endophytes: Common Genera, Seed-to-Seed Variability and Their Possible Role in Plants," Acta Hort., 2012, pp. 39-48, vol. 938.

Rosenblueth, M., et al., "Bacterial Endophytes and Their Interactions With Host," Molecular Plant-Microbe Interactions, 2006, pp. 827-837, vol. 19, No. 8.

Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Samac, D.A., et al., "Recent Advances in Legume-Microbe Interactions: Recognition, Defense Response, and Symbiosis from a Genomic Perspective," Plant Physiol., 2007, pp. 582-587, vol. 144.

Samways, M.J., et al., "Assessment of the Fungus *Cladosporium oxyspoum* (BERK. and CURT.) as a Potential BioControl Agent Against Certain Homoptera," Elsevier Science Publioshers B.V., Jan. 1, 1986, pp. 231-239.

Sardi, P., et al., "Isolation of Endophytic Streptomyces Strains from Surface Sterilized Roots," Applied and Environmental Microbiology, 1992, pp. 2691-2693, vol. 58, No. 8.

Sarwar, M., et al., "Tryptophan Dependent Biosynthesis of Auxins in Soil," Plant Soil, 1992, pp. 207-215, vol. 147.

Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74 , No. 1.

Schmieder, R., et al., "Quality Control and Preprocessing of Metagenomic Datasets," Bioinformatics, 2011, pp. 863-864, vol. 27, No. 6.

Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay for the Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, Rhizoctonia batatiola," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Shankar, M., et al.,"Root colonization of a rice growth promoting strain of Enterobacter cloacae," Journal of Basic Microbiology, 2011, pp. 523-530, vol. 51.

Shiraishi, A., et al., "Nodulation in black locust by the ammaproteobacteria *Pseudomonas* sp. and the Betaproteobacteria *Burkholderia* sp", Systematic and Applied Microbiology, Aug. 2010, pp. 269-274, vol. 33, No. 5.

(56) References Cited

OTHER PUBLICATIONS

Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, pp. 381-387, vol. 46.
Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.
Soares, M. M. C. N., et al., "Screening of Bacterial Strains for Pectinolytic Activity: Characterization of the Polygalacturonase Produced by *Bacillus* SP," Revista de Microbiolgia, 1999, pp. 299-303, vol. 30.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.
Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A. K., et al., "Variations in Exopolysaccharide Production by Rhizobium tropici," Arch Microbiol., 2012, pp. 197-206, vol. 194.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (*Daucus carota* L. var. sativus): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013.
Sword, G., "Fungal Endophytes to Protect Cotton from Insects and Nematodes," Power Point Presentation dated Dec. 7, 2012, 20 Pages.
Sword, G., "Natural Enemies—The Forgotten Basis of IPM?," Power Point Presentation dated Sep. 6, 2013.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.
Tamura, K., et al., "Estimation of the number of nucleotide substitutions in the control region of mitochondrial DNA in humans and chimpanzees," Molecular Biology and Evolution, 1993, vol. 10, No. 3, pp. 512-526.
Taylor, A. G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in Spodoptera litura (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces Lydicus WYEC108 and the Pea Plant (*Pisum Sativum*)," Applied and Environmental Microbiology, May 2002, pp. 2161-2171, vol. 68, No. 5.
Trichoderma definition, 2016, 6 pages, [online] [Retrieved on Sep. 16, 2016,] Retrieved from the Internet <URL:https://en.wikipedia.org/wiki/Trichoderma>.
Trotel-Aziz, P., et al., "Characterization of New Bacterial Biocontrol Agents *Acinetobacter, Bacillus, Pantoea* and *Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
U'Ren, J.M., et al., "Host and geographic structure of endophytic and endolichenic fungi at the continental scale," American Journal of Botany, May 1, 2012, pp. 898-914, vol. 99, No. 5.
Usadel, B., et al., "The Plant Transcriptome-From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Valencia, E., et al., "Mini-review: Brazilian fungi diversity for biomass degradation," Fungal Genetics and Biology, 2013, pp. 9-18, vol. 60.
Van Der Lelie, D., et al., "Poplar and its Bacterial Endophytes: Coexistence and Harmony," Critical Rev Plant Sci., 2009, pp. 346-358, vol. 28.
Verkley, G., et al., "*Paraconiothyrium*, a new genus to accommodate the mycoparasite *Coniothyrium minitans*, anamorphs of Paraphaeosphaeria, and four new species," Studies in Mycology, 2004, pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.

(56) References Cited

OTHER PUBLICATIONS

Viruel, E., et al., "Pseudomonas thiveralensis Strain IEHa 16S Ribosomal RNA Fene, Partial Sequence," NCBI GenBank Accession No. GQ169380.1, Submitted May 15, 2009.
Visagie, C.M., et al., "Identification and nomenclature of the genus Penicillium," Studies in Mycology, Jun. 2014, pp. 343-371, vol. 78.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al.,"Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol, 2007, vol. 29, p. 451.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.
Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulata," Arch Microbiol., 1975, pp. 207-216, vol. 105.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.

Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
Yezerski, A., et al., "The Effects of the Presence of Stored Product Pests on the Microfauna of a Flour Community," Journal of Applied Microbiology, 2005, pp. 507-515, vol. 98.
You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhang, Y., et al., "BcGsl, a glycoprotein from Botrytis cinerea, elicits defence response and improves disease resistance in host plants," Biochemical and Biophysical Research Communications, 2015, vol. 457, No. 4, pp. 627-634.
Zhang, W., et al., Host range of Exserohilum monoceras, a potential bioherbicide for the control of Echinochloa species, Canadian Journal of Botany/ Journal Canadien De Botan, National Research Council, Ottawa, CA, vol. 75, Jan. 1, 1997, pp. 685-692.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal Endophyte *Paecilomyces* sp. in Cotton on the Roo-Knot Nematode Meloidogyne incognita," poster dated Jan. 7, 2013.
Zhu et al.,Helminthosporium velutinum and *H. aquaticum* sp. nov. from aquatic habitats in Yunnan Province, China. Phytotaxa, 2016, vol. 253, No. 3, pp. 179-190.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
Allard, G. et al., "SPINGO: a rapid species-classifier for microbial amplicon sequences," BMC Bioinformatics, 2015, vol. 16, No. 324, 8 pages.
Anders, S. et al., "Differential expression analysis for sequence count data," Genome Biology, 2010, vol. 11, No. 11, pp. R106.
Ardakani, M.R. et al., "Absorption of N, P, K through triple inoculation of wheat (*Triticum aestivum* L.) by Azospirillum brasilense, *Streptomyces* sp., Glomus intraradices and manure application," Physiol Mol Biol Plants, 2011, vol. 17, No. 2, pp. 181-192.
Bevivino, A. et al., "Characterization of a free-living maize-rhizosphere population of *Burkholderia cepacia*: effect of seed treatment on disease suppression and growth promotion of maize," FEMS Microbiology Ecology, 1998, vol. 27, pp. 225-237.
Chen, F. et al., "Assessing Performance of Orthology Detection Strategies Applied to Eukaryotic Genomes," PLoS ONE, Apr. 2007, No. 4, pp. e383.
Ciccillo. F. et al., "Effects of two different application methods of *Burkholderia ambifaria* MCI 7 on plant growth and rhizospheric bacterial diversity," Environmental Microbiology, 2002, vol. 4, No. 4, pp. 238-245.
Cole, J.R. et al., "Ribosomal Database Project: data and tools for high throughput rRNA analysis," Nucleic Acids Research, 2014, vol. 42, pp. D633-D642.

(56) References Cited

OTHER PUBLICATIONS

De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Deshpande, V. et al., "Fungal identification using a Bayesian classifier and the Warcup training set of internal transcribed spacer sequences," Mycologia, 2016, vol. 108, No. 1, pp. 1-5.
Edgar, R.C., "UNOISE2: Improved Error-Correction for Illumina 16S and ITS Amplicon Sequncing," BioRxiv, 2016, No. 081257, 21 pages.
Enright, A.J. et al., "An efficient algorithm for large-scale detection of protein families," Nucleic Acids Research, 2002, vol. 30, No. 7, pp. 1575-1584.
Enright, A.J. et al., "Protein families and TRIBES in genome sequence space," Nucleic Acids Research, 2003, vol. 31, No. 15, pp. 4632-4638.
Estrada, P. et al., "A N2-fixing endophytic *Burkholderia* sp. Associated with maize plants cultivated in Mexico," Canadian Journal of Microbiology, 2002, vol. 48, No. 4, pp. 285-294.
Friedman, J. et al., "Regularization Path for Generalized Linear Models via Coordinate Descent," Journal of Statistical Software, 2010, vol. 33, No. 1, pp. 1-22.
Koljalg. U. et al., "Towards a unified paradigm for sequence-based identification of fungi," Molecular Ecology, 2013, vol. 22, pp. 5271-5277.
Kozich, J.J. et al., "Development of a Dual-Index Sequencing Strategy and Curation Pipeline for Analyzing Amplicon Sequence Data on the MiSeq Illumina Sequencing Platform," Applied and Environmental Microbiology, Sep. 2013, vol. 79, No. 17, pp. 5112-5120.
Langille, M.G.I. et al., "Predictive functional profiling of microbial communities using 16S rRNA marker gene sequences," Nature Biotechnology, 2013, vol. 31, No. 9, pp. 814-821.
Li, W. et al., "Ultrafast clustering algorithms for metagenomic sequence analysis," Briefings in Bioinformatics, Nov. 1, 2012, vol. 13, No. 6., pp. 656-668.
McMurdie, P.J. et al., "Waste Not, Want Not: Why Rarefying Microbiome Data Is Inadmissible," PLOS Computational Biology, 2014, vol. 10, No. 4, pp. e1003531.
Needleman, S.B. et al., "A General Method Applicable to the Search for Similarities in the Amino Acid Sequence of Two Proteins," Journal of Molecular Biology, 1970, vol. 28, No. 3, pp. 443-453.
Quast, C. et al., "The SILVA ribosomal RNA gene database project: improved data processing and web-based tools," Nucleic Acids Research, 2013, vol. 41, pp. D590-D596.
Rideout, J.R. et al., "Subsampled open-reference clustering creates consistent, comprehensive OTU definitions and scales to billions of sequences," PeerJ, 2014, 2:e545.
Roth, A.C.J. et al., "Algorithm of OMA for large-scale orthology inference," BMC Bioinformatics, 2008, vol. 9, pp. 518.
"Sequence Alignment of JQ047949 with Instant SEQ ID No. 2," Search conducted on Jan. 2, 2019. 2 pages.
Sharma, V.K. et al., "Enhancement of verticillium wilt resistance in tomato transplants by in vitro co-culture of seedlings with a plant growth promoting rhizobacterium (*Pseudomonas* sp. Strain PsJN)," Canadian Journal of Microbiology, Jun. 1998, vol. 44, No. 6, pp. 528-536.
Shenoy, B.D. et al., "Impact of DNA sequence-data on the taxonomy of anamorphic fungi," Fungal Diversity, 2007, vol. 26, No. 10, pp. 1-54.
Smith, T.F. et al., "Identification of Common Molecular Subsequences," Journal of Molecular Biology, 1981, vol. 147, pp. 195-197.
United States Patent Office, Non-Final Office Action, U.S. Appl. No. 14/766,065, dated Oct. 27, 2017, 10 pages.
United States Patent Office, Final Office Action, U.S. Appl. No. 14/766,065, dated Aug. 29, 2018, 6 pages.
Yashiro et al., "Effect of Streptomycin Treatment on Bacterial Community Structure in the Apple Phyllosphere," PLOS ONE, May 21, 2012, vol. 7, No. 5, 10 pages.
Ngom, A et al., "A novel symbiotic nitrogen-fixing member of the Ochrobactrum Glade isolated from root nodues of Acacia mangium". J. Gen. Appl. Microbiol. (2004) 50: 17-27.
Trujillo, M.E et al., "Nodulation of Lupinus albus by strins of *Ochrobactrum lupini* sp. nov." Appl. Environ Microbiol Mar. 2005; 71(3): 1318-1327.
Bal, H.B et al., "Isolation of ACC deaminase producting PGPR from rice rhizosphere and evaluating their plant growth promoting activity under salt stress". Plant Soil (2013) 366: 93-105 doi: 10/1007/s11104-012-1402-5.
Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI:10.1111/j.1365-2672.2009.04242.x <https://doi.org/10.1111/j.1365-2672.2009.04242.x.
Sulistiyani, et al., "Population and Diversity of Endophytic Bacteria Associated with Medicinal Plan Curumma zedoaria", Microbiology Indonesia 8.2 (2014):4.
United States Patent Office, Non-Final Office Action, U.S. Appl. No. 14/964,429, dated Aug. 9, 2016, 6 Pages.
United States Patent Office, Final Office Action, U.S. Appl. No. 14/964,429, dated May 31, 2017, 9 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/063,350, dated Nov. 10, 2016, 18 Pages.
United States Patent Office, Final Office Action, U.S. Appl. No. 14/614,193, dated Dec. 22, 2016, 13 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/107,965, dated Jun. 21, 2018, 27 Pages.
Abello, J., et al., "Agrobacterium-mediated transformation of the endophytic fungus *Acremonium implicatum* associated with Brachiaria grasses", Mycological Research, pp. 407-413, vol. 112, Pt 3.
Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.
Antony-Badu, S., et al., "Multiple Streptomyces species with distinct secondary metabolomes have identical 16S rRNA gene sequences." Scientific Reports 7.1, Sep. 2017, No. 7, 11089, pp. 1-8.
Artursson V. et al., "Interactions between arbuscular mycorrhizal fungi and bacteria and their potential for stimulating plant growth", Environmental Microbiology, vol. 8, No. 1, Jan. 1, 2006, pp. 1-10.
Azcon, R., et al., "Selective interactions between different species of mycorrhizal fungi and Rhizobium meliloti strains, and their

(56) References Cited

OTHER PUBLICATIONS effects on growth, N2-fixation (15N) and nutrition of *Medicago sativa* L.," New Phytol., 1991, vol. 117, pp. 399-404.
Bandara, WM.M.S., et al., "Interactions among endophytic bacteria and fungi: effects and potentials" Journal of Biosciences, Dec. 2006, vol. 31, No. 5, pp. 645-650.
Barnett, S., et al., "Selection of microbes for control of Rhizoctonia root rot on wheat using a high throughput pathosystem", Biological Control, Jul. 6, 2017, 113: 45-57.
Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.
Bashan, Yoav E., et al., "Alginate Beads as Synthetic Inoculant Carriers for Slow Release of Bacteria that Affect Plant Growth," Applied and Environmental Microbiology, pp. 1089-1098, May 1986.
Bragantia, et al, "Identificaqao E Avaliaqao De Rizobacterias Isoladas De Raizes De Milho," Jan. 1, 2010, pp. 905-911, Retrieved from the Internet: URL:scielo.br/pdf/brag/v69n4/v69n4a17.pdf (With English Abstract).
Chenhua Li , et al., "Change in deep soil microbial communities due to long-term fertilization," Soil Biology and Biochemistry, vol. 75, Mar. 5, 2014, pp. 264-272, XP055530941.
Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.
De Medeiros, L., et al., "Evaluation of Herbicidal Potential of Depsides from Cladosporium uredinicola an Endophytic Fungus found in Guava Fruit," J. Braz. Chem. Soc., 2012, vol. 23, No. 8, p. 1551-1557.
Fatima Z et al, "Antifungal activity of plant growth-promoting rhizobacteria isolates against Rhizoctonia solani in wheat", African Journal of Biotechnology, 2009, 8: 219-225.
Fox, G., et al., "How close is close: 16S rRNA sequence identity may not be sufficient to guarantee species identity." International Journal of Systematic and Evolutionary Microbiology 42.1, 1992, pp. 166-170.
NCBI GenBank: Accession No. JX880250.1, "Enterobacteriaceae bacterium Clero1 16S ribosomal RNA gene, partial sequence," NIH, Jun. 24, 2015, 2 Pages, can be retrieved at <URL:ncbi.nlm.nih.gov/nucleotidelJX880250.1?report=genbank&log$=nuclalign&blast_rank=80 &RID=KWUPBV08015>.
GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.
NCBI, GenBankAccession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.
Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hain, T., et al., "Chitinolytic transgenes from Streptomyces albidoflavus as phytochemicals defences against; herbivorous insects, use in transgenic plants and effect in plant development", International Journal of Systematic Bacteriology, Jan. 1997, vol. 47, No. 1, pp. 202-206.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter genomospecies* I", BMC Evolutionary Biology 2007, Apr. 17, 2017, 11 pages.
Joe, M.M. et al., "Development of alginate-based aggregate inoculants of *Methylobacterium* sp. and Azospirillum brasilense tested under in vitro conditions to promote plant growth," Journal of Applied Microbiology 2013, 116(2):408-423, XP055225426, Nov. 22, 2013.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Li, M., et al., "ATP Modulates the Growth of Specific Microbial Strains", Current Microbiology, May 30, 2010, vol. 62, No. 1, pp. 84-89.
Manoharan, M. J. et. Al., "Survival of flocculated cells in alginate and its inoculatin effect on growth and yield of maize under water deficit conditions," EP J of Soil Biology, Gauthier-Villars, Montrouge, FR, vol. 50, Mar. 7, 2012, pp. 198-206, XP028421147.
Murali, Gopal, et al., "Microbiome Selection Could Spur Next-Generation Plant Breeding Strategies," Frontiers in Microbiology, vol. 7, Dec. 7, 2016, XP055531064.
Ogbo, F., et al., "Some Characteristics of a Plant Growth Promoting; iEnterobacter/isp. Isolated from the Roots of Maize", Advances in Microbiology, Jan. 1, 2012, vol. 02, No. 03, pp. 368-374.
Orakçi GE et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
Sarkar, S., et al., "New report of additional enterobacterial species causing wilt in West Bengal, India," Canadian Journal of Microbiology, 2015, vol. 61, No. 7, pp. 477-486.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
NCBI, GenBankAccession No. KX641980.1, Jul. 29, 2017, Scott, M., et al., "*Dothideomycetes* sp. isolate FT14-6 internal transcribed spacer 1, partial sequence; 5.85 ribosomal RNA gene and internal transcribed spacer 2, complete sequence; and large subunit ribosomal RNA gene, partial sequence," 2 Pages, Can be retrieved at<URL:ncbi.nlm.nih.gov/nuccore/KX641980>.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" World J Microbiol Biotechnol., 2014, pp. 835-845, vol. 30.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
PCT International Search Report and Written Opinion for PCT/US2017/064361, dated May 11, 2018, 22 Pages.
PCT International Search Report and Written Opinion, PCT Application No. PCT/US2017/064292, dated May 11, 2018, 20 Pages.
European Patent Office, Extended European Search Report, European Patent Application No. EP 15876324.3, dated Jun. 12, 2018, 9 Pages.

(56) References Cited

OTHER PUBLICATIONS

PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT International Search Report and Written Opinion, PCT Application No. PCT/US2017/068255, dated Mar. 19, 2018, 14 Pages.
European Patent Office, Communication Pursuant to Article 94(3) EPC for European Patent Application No. EP 14748326.7, dated Feb. 15, 2018, 7 Pages.
European Patent Office, Supplementary European Search Report for European Patent Application No. 15810847.2, dated Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14874589.6, dated Jul. 11, 2017, 9 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
PCT Invitation to Pay Additional Fees, PCT Application No. PCT/US2015/068206, dated Apr. 12, 2016, 5 Pages.
European Patent Office, Supplementary European Search Report, European Patent Application No. 13874703.5, dated Jun. 21, 2016, 3 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
International Search Report and Written Opinion, Application No. PCT/US2014/054160, dated Dec. 9, 2014, 21 Pages.
Invitation to Pay Additional Fees, PCT Application No. PCT/US2014/064411, dated Feb. 5, 2015, 2 Pages.
International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
International Search Report and Written Opinion, International Application No. PCT/US2014/072399, dated Jun. 26, 2015, 22 Pages.
Invitation to Pay Additional Fees, PCT Application No. PCT/US2014/072400, dated Apr. 16, 2015, 6 Pages.
International Search Report and Written Opinion, Application No. PCT/US2014/072400, dated Jul. 8, 2015, 38 Pages.
Invitation to Pay Additional Fees, PCT Application No. PCT/US2015/038110, dated Sep. 22, 2015, 8 Pages.
Invitation to Pay Additional Fees, PCT Application No. PCT/US2015/038187, dated Oct. 14, 2015, 5 Pages.
PCT International Search Report and Written Opinion for PCT/AU2018/050387, dated Jul. 12, 2018, 8 pages.
PCT International Search Report and Written Opinionfor PCT/US2018/051467, dated Mar. 25, 2019 26 pages.
PCT Invitation to Pay Additional Fees, PCT Application No. PCT/CA2013/000091, dated Mar. 27, 2013, 2 Pages.
PCT International Search Report and Written Opinion for PCT/EP2013/062976, dated Dec. 22, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2015/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Supplementary European Search Report, European Patent Application No. 14860187.5, dated May 24, 2017, 9 Pages.
Hanshew, A., et al., "Characterization of Actinobacteria Associated with Three Ant-Plant Mutualisms", Microbiol Ecology, Aug. 6, 2014, vol. 69, No. 1, pp. 192-203.
NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https://www.ncbi.nlm.nih.gov/nuccore/J Q765415.1/.
NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/K C355340.
NCBI GenBank: Accession No. XP55670279, "Uncultured bacterium clone bb2s4 16S ribosomal RNA gene, partial seque—

(56) References Cited

OTHER PUBLICATIONS

Nucleotide", May 6, 2005, 1 Page, can be retreived at URL:https://www.ncbi.nlm.nih.gov/nuccore/D Q068880.

European Patent Office, Communication Pursuant to Article 94(3) EPC for European Patent Application No. EP 14777213.1, dated Jun. 18, 2018, 4 Pages.

Result 11 from a search in the GenEmbl database, GenEmbl Record No. EU 977189, Smith et al., "Bioactive endophytes warrant intensified exploration and conservation," PLoS ONE 3(8):E3052, 2008.

Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.

PCT International Search Report and Written Opinion for PCT/US2018/051467, dated Feb. 4, 2019, 22 pages.

Chaves, J., et al., "Identification and Phylogeny of Streptomyces Based on Gene Sequences", Research Journal of Microbiology, vol. 13, No. 1, Dec. 15, 2017, pp. 13-20, XP055675917.

Girard, G., et al., "A novel taxonomic marker that discriminates between morphologically complex actinomycetes", Open Biology, vol. 3, No. 10, Oct. 2013, p. 130073,XP055675916.

Guo, Y., et al. "A multi locus phylogeny of the Streptomyces griseus 16S rRNA gene Glade: use of multilocus sequence analysis for streptomycete systematics", International Journal of Systematic and Evolutionary Microbiology, vol. 58, No. 1, 2008, pp. 149-159, XP055675936.

PCT Invitation to Pay Additional Fees, PCT Application No. PCT/US2017/064292, dated Mar. 6, 2018, 15 Pages.

PCT International Search Report and Written Opinion PCT/AU2018/050387, dated Jul. 12, 2018 (Filing date is Apr. 27, 2018).

PCT International Search Report and Written Opinion for PCT/US2017/064292, dated May 11, 2018, 20 Pages.

Bentley, S.D., et al, Complete genome sequence of the model actinomycete Streptomyces coelicolor A3(2), Nature. May 9, 2002;417(6885):141-7. (Year: 2002).

Gabor, J., et al., "Mycorrhizal fungi effects on nutrient composition and yield of soybean seeds," Journal of Plant Nutrition, 20:4-5, 581-591, 1997.

Gopalakrishnan, S. et al., "Plant growth-promoting activities of *Streptomyces* spp. in sorghum and rice", SpringerPlus, 2/1/574, pp. 1-8, http://www.springerplus.com/content/2/1/574, 2013.

Groppe, K., et al., "Interaction between the endophytic fungus Epichloë bromicola and the grass Bromus erectus: effects of endophyte infection, fungal concentration and environment on grass growth and flowering," Mol Ecol., 8:1827-1835, 1999.

Hubbard, M., "Fungal Endophytes that Confer Heat and Drought Tolerance to Wheat," Doctoral dissertation, University of Saskatchewan, 2012.

Ikeda, H., et al., "Complete genome sequence and comparative analysis of the industrial microorganism *Streptomyces avermitilis*," Nat Biotechnol. May 2003;21 (5) :526-31. Epub Apr. 14, 2003. (Year: 2003).

Lee, J. et al., "*Streptomyces koyangensis* sp. nov., a novel actinomycete that produces 4-phenyl-3-butenoic acid," Int J Syst Evol Microbiol. Jan. 2005;55(Pt 1):257-62. (Year: 2005).

Lind, A., et al., "Drivers of genetic diversity in secondary metabolic gene clusters within a fungal species", PLOS Biology, Nov. 17, 2017, 26 pages.

Pacovsky, R., "Carbohydrate, protein and amino acid status of Glycine-Glomus-Bradyrhizobium symbioses," Physiologia Pantarium; 75:346-354, 1989).

Sha, T. et al., "Genetic diversity of the endemic gourmet mushroom *Thelephora ganbajun* from southwestern China", Microbiology (2008), 154, 3460-3468.

Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.

Wiebold M. et al., "Agriculture Experiment Station, College of Agriculture, Food & Natural Resources, University of Missouri, Special Report 589, pp. 1-124)."

United States Patent Office, Non-Final Office Action, U.S. Appl. No. 15/143,398, dated Sep. 22, 2017, 16 Pages.

PCT International Search Report and Wlitten Opinion, PCT Application No. PCT/US2015/068206, dated Jun. 27, 2016, 20 Pages.

PCT International Search Report and Wrrtten Opinion, PCT Application No. PCT/US2016/030292, dated Aug. 12, 2016, 20 Pages.

PCT International Search Report and Wrrtten Opinion, PCT Application No. PCT/US2016/030293, dated Aug. 11, 2016, 23 Pages.

PCT International Search Report and Wlitten Opinion, PCT Application No. PCT/US2016/036504, dated Nov. 4, 2016, 18 Pages.

Soe, K.M, et al, "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).

Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.

Ciccillo, F., et al., Effects of two different application methods of Burkholderia ambifaria MCI 7 on plant growth and rhizospheric bacterial diversity.

Estrada, P., et al., "A N2- fixing endophytic Burkholderia sp. associated with maize plants culitvated in Mexico", Canadian Journal of Microbiology (2002), vol. 48(4), pp. 528-536.

Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.

Grady, E., et al., "Current knowledge and perspectives of Paenibacillus: a review" Microb Cell Fact (2016) 15:203.

Li, J., et al., "Antitumour and antimicrobial activities of endophytic stretomycetes from pharmaceutical plants in rainforest", Lett Appl Microbiol. Dec. 2008; 47(6): 574-80. (Year: 2008).

Hamayun, M., et al., "Gibberellin production and plant growth promotion from pure cultures of Cladosporium sp. MH-6 isolated from cucumber (*Cucumis sativus* L.)", Mycologia, 102 (5), 2010, pp. 989-995.

Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.

Kim, S., et al., "Physiological and proteomic analyses of Korean F1 maize (*Zea mays* L.) hybrids under water-deficit stress during flowering", Appl. Biol. Chem. (2019) 62:32.

Halligan, B., et al., "Cloning of the murine cDNA encoding VDJP, a protein homologous to the large subunit of replication factor C and bacterial DNA ligases", GENE (1995) 217-222.

Arend, J., et al., "Hydroquinone: O-glucosytransferase from cultivated Rauvolfia cells: enrichment and partial amino acid sequences", Phytochemistry (2000) 53:187-193.

Enchev, R., et al., "Protein neddylation: beyond cullin-RING ligases", (Nature Reviews: Molecular Cell Biology (2015) 16:30-44.

Bais, H, et al., "The Role of Root Exudates in Rhizosphere Interactions with Plants and Other Organisms", Annual Review. Plant Biol. (2006) 57:233-266.

Goepfert, S., et al., "Molecular Identification and Characterization of the Arabidopsis D3,5, D2,4-Dienoyl-Coenzym A Isomerase, a Peroxisomal Enzyme Participating in the b-Oxidation Cycle of Unsaturated Fatty Acids1", Plant Physiology (2005) 138:1947-1956.

Thomas, P., et al: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.

Database Geneseq [Online] Sep. 30, 2010 (Sep. 30, 2010), "Cellulomonas fermentans 16s rRNA gene SEQ ID:39.", retrieved from

(56) References Cited

OTHER PUBLICATIONS

EBI accession No. GSN:AWL84299 Database accession No. AWL84299; & JP 2009 072168 A (Univ of Occupational & Environ) Apr. 9, 2009 (Apr. 9, 2009).
European Patent Office, Partial European Search Report, European Patent Application No. 20171870.7, dated Nov. 20, 2020, 18 Pages.

* cited by examiner

SEQUENCE LISTING

```
<160> NUMBER OF SEQ ID NOS: 19

<210> SEQ ID NO 1
<211> LENGTH: 581
<212> TYPE: DNA
<213> ORGANISM: Cladosporium sp.

<400> SEQUENCE: 1
cctatagctg actgcggagg gacattacaa gtgacccegg tctaaccacc gggatgttca        60
taaccctttg ttgtccgact ctgttgcctc cggggcgacc ctgccttcgg gcgggggctc       120
cgggtggaca cttcaaactc ttgcgtaact ttgcagtctg agtaaactta attaataaat       180 taaaacttt aacaacggat ctcttggttc tggcatcgat gaagaacgca gcgaaatgcg        240
ataagtaatg tgaattgcag aattcagtga atcatcgaat ctttgaacgc acattgcgcc      300
ccctggtatt ccggggggca tgcctgttcg agcgtcattt caccactcaa gcctcgcttg       360
gtattgggca acgcggtccg ccgcgtgcct caaatcgacc ggctgggtct tctgtccect       420 aagcgttgtg gaaactattc gctaaagggt gttcgggagg ctacgccgta aaacaacccc       480
atttctaagg ttgacctcgg atcaggtagg gatacccgct gaacttaagc atatcaataa      540
gcggaggaaa agaaaccaac agggattgcc ccagtaacga a                           581

<210> SEQ ID NO 2
<211> LENGTH: 571
<212> TYPE: DNA
<213> ORGANISM: Cladosporium sp.

<400> SEQUENCE: 2
tcgatctagc tcatagtgac tgcggaggga cattacaagt gacccggtc taaccaccgg        60 gatgttcata acccttttgtt gtccgactct gttgcctccg gggcgaccct gccttcgggc     120
gggggctccg ggtggacact tcaaactctt gcgtaacttt gcagtctgag taaacttaat     180
taataaatta aaacttttaa caacggatct cttggttctg gcatcgatga agaacgcagc     240
gaaatgcgat aagtaatgtg aattgcagaa ttcagtgaat catcgaatct tgaacgcac     300 attgcgccc ctggtattcc gggggcatg cctgttcgag cgtcatttca ccactcaagc      360
ctcgcttggt attgggaaac gcggaccgac gcgtgcctca aatcgaccgg cagggtcttc    420
```

```
tgtcccctaa acgttgtgaa aattattcga taaaggatgt tccgtgctac attgtgaata      480
gaaccgcatt tataacattg attataaact aattacgact acatggtaag atagatatat      540
caaggaactt cctctaaatg accaagaaac c                                     571

<210> SEQ ID NO 3
<211> LENGTH: 592
<212> TYPE: DNA
<213> ORGANISM: Penicillium sp.

<400> SEQUENCE: 3
tcgacggcgt atcctagtga ctgcggagga tcattaccga gtgagggccc tctgggtcca       60
acctcccacc cgtgtttaat ttaccttgtt gcttcggcgg gcccgcctta actggccgcc      120
gggggcttac cgcccccggg cccgcgcccg ccgaagacac cctcgaactc tgtctgaaga      180
ttgtagtctg agtgaaaata taaattattt aaaactttca acaacggatc tcttggttcc      240
ggcatcgatg aagaacgcag cgaaatgcga tacgtaatgt gaattgcaaa ttcagtgaat      300
catcgagtct ttgaacgcac attgcgcccc ctggtattcc gggggcatg cctgtccgag       360 cgtcattgct gccctcaagc acggcttgtg tgttgggccc cgtcctccga tcccggggga      420
cgggcccgaa aggcagcggc ggcaccgcgt ccggtcctcg agcgtatggg gctttgtcac      480
ccgctctgta ggcccggccg gcgcttgccg atcaacccaa attttttatcc aggttgacct      540 cggatcaggt agggataccc gctgaactta agcatatcaa taagcggagg aa              592

<210> SEQ ID NO 4
<211> LENGTH: 605
<212> TYPE: DNA
<213> ORGANISM: Pseudeurotium sp.

<400> SEQUENCE: 4
taactgattt ggcggactgg cggaaggaca ttaaagagac gttgcccttc ggggtatacc       60 tcccacccctt tgtttacctt ttcctttgtt gctttggcgg gccgtcctc ggaccaccgg      120 tttcggctgg tcagtgcccg ccagaggacc taaaactctg tttgttcata ttgtctgagt      180
actatataat agttaaaact ttcaacaacg gatctcttgg ttctggcatc gatgaagaac      240
gcagcgaaat gcgataagta atgtgaattg cagaattcag tgaatcatcg aatctttgaa      300
cgcacattgc gcccctggt attccggggg gcatgcctgt cgagcgtca ttacaaccct       360 caagctctgc ttggtattgg gctctgccgg tcccggcagg ccttaaaatc attggcggtg      420
ccattcggct tcaagcgtag taattcttct cgctttggag accgggtgc gtgcttgcca       480 tcaaccccca attttttcag gttgacctcg gatcaggtag ggataccgc tgaacttaag      540 catatcaata agcggaggaa aagaaaccaa cagggattgt cccaataacg aatttataaa      600
taata                                                                 605

<210> SEQ ID NO 5
<211> LENGTH: 579
<212> TYPE: DNA
<213> ORGANISM: Paraconyothirium sp.

<400> SEQUENCE: 5
tcgagagttc ggactaagtg cctgatccga ggtcaagacg gtaatgttgc ttcgtggacg       60
cgggccacgc cccccgcag acgcaattgt gctgcgcgag aggaggcaag gaccgctgcc      120
aatgaatttg gggcgagtcc gcgcgcgaag gcgggacaga cgcccaacac caagcagagc      180
ttgagggtgt agatgacgct cgaacaggca tgccccatgg aataccaagg ggcgcaatgt      240
```

```
gcgttcaaag attcgatgat tcactgaatt ctgcaattca cactacttat cgcatttcgc      300
tgcgttcttc atcgatgcca gagccaagag atccattgtt gaaagttgta acgattgttt      360
gtatcagaac aggtaatgct agatgcaaaa aaggttttgt taagttccag cggcaggttg      420
ccccgccgaa ggagaacgaa aggtgctcgt aaaaaagga tgcaggaatg cggcgcgtga      480
gggtgttacc cctaccaccc gggagagaac ccccgagggc cgcgaccgca cctggttgag      540
atggataatg atccttccgc aggttcacct acggaaacc                            579

<210> SEQ ID NO 6
<211> LENGTH: 1160
<212> TYPE: DNA
<213> ORGANISM: Streptomyces sp.

<400> SEQUENCE: 6
ccgggggcac tccactgcgt atgtgtgacg agtagaccgc tgcgcttagc tgaggtctga       60
tgaaatgtag aacacttaac aaaaatatgc ccggatggat atacttttca acgacagggc      120
tgcgattgga tgatctcctt tgaaacacag aactagtcac ggcgacgaat actcaacttc      180 gaccccccc ctttctggag gcgcgtctta gtcccctcct tgatggagct gccccgtgct      240
cggcggccgg agtcggcggt gttttccgct gtacctgaga cgctggacca actccttcgg      300
gaggcagcag tggggaatat tgcacaatgg gcgcaagcct gatgcagcga cgccgcgtga      360
gggatgacgg ccttcgggtt gtaaacctct ttcagcaggg aagaagcgca agtgacggta      420
cctgcagaag aagcgccggc taactacgtg ccagcagccg cggtaatacg tagggcgcaa      480
gcgttgtccg gaattattgg gcgtaaagag ctcgtaggcg gcttgtcacg tcgattgtga      540
aagcccgagg cttaacctcg gtctgcagt cgatacgggc aggctagagt gtggtagggg      600
agatcggaat tcctggtgta gcggtgaaat gcgcagatat caggaggaac accggtggcg      660
aaggcggatc tctgggccat tactgacgct gaggagcgaa agcgtgggga gcgaacagga      720
ttagataccc tggtagtcca cgccgtaaac ggtgggaact aggtgttggc gacattccac      780
gtcgtcggtg ccgcagctaa cgcattaagt tccccgcctg gggagtacgg ccgcaaggct      840
aaaactcaaa ggaattgacg ggggcccgca caagcggcgg agcatgtggc ttaattcgac      900
gcaacgcgaa gaaccttacc aaggcttgac atacaccgga acatccaga tgggtgcc       960 cccttgtggt cggcgtacag gtcgtgcatg gctgtcgtca gctcgtgtcg tgagatgttg     1020
ggtaagtccc gcaacgagcg caaccttgtt ctggtgctgc cagcatgccc ttcgggtgat     1080
gggacttcac cacggagacc gcggctccac tccgacgagg tggggacga cgtcagtcat     1140 catgccctaa tgtctggctg                                                1160

<210> SEQ ID NO 7
<211> LENGTH: 1176
<212> TYPE: DNA
<213> ORGANISM: Rhizobium sp.

<400> SEQUENCE: 7 ggaaggggg cggcttacca tgcaagtcga gcgccccgca aggggagcgg cagacgggtg       60
agtaacgcgt gggaatctac ccttgactac ggaataacgc agggaaactt gtgctaatac      120
cgtatgtgtc cttcgggaga aagatttatc ggtcaaggat gagcccgcgt tggattagct      180
agttggtggg gtaaaggcct accaaggcga cgatccatag ctggtctgag aggatgatca      240
gccacattgg gactgagaca cggcccaaac tcctacggga ggcagcagtg gggaatattg      300
```

```
gacaatgggc gcaagcctga tccagccatg ccgcgtgagt gatgaaggcc ctagggttgt    360
aaagctcttt caccggagaa gataatgacg gtatccggag aagaagcccc ggctaacttc    420
gtgccagcag ccgcggtaat acgaaggggg ctagcgttgt tcggaattac tggccgtaaa    480
gcgcacgtag gcggatcgat cagtcagggg tgaaatccca gggctcaacc ctggaactgt    540
ctttgatact gtcgatctgg agaacttcct gctcgagtga tttacccaca tggcgagcac    600
cggcaccccg tttcgacatg caaaaaatga tgcccaggct tatgtttgac ctggctgcta    660
cggctctctt cggcgtggac cccggcctcc tatccccgga gatgccaccc atggacgccg    720
cagtctccat ggatatatca tggaggtggg ttttctccga ctcatgatgc cggcttcttg    780
ctggaagttg atgaagcaac taaacatcag ccctgagaga aagcttcgca tgccgcgcag    840
ggtgctccga gtgttcgtct ggagatgatg aaatagacga agatcatctc atgtcatgtt    900
ggtaacgacg agaacaagat ggtgtggatt ttgtgtcttc catcctccat gaccctgacg    960
atgctgatga tgacgtggtt catgctatga tgactcgata ctggtcgctg caagcggata   1020
cagttgggac ctaccgctaa catggttctt tctacaacct ccccccaaac cgcataggat   1080
cgtggtcaat cattcggcac gaacctcttc ccccattgcc tccaactagt ttatcgctct   1140
agagttgggg agccctgtgt gacctttcgt acgcga                             1176
```

<210> SEQ ID NO 8
<211> LENGTH: 24
<212> TYPE: DNA
<213> ORGANISM: Pea-Pisum sativum

<400> SEQUENCE: 8
ccacattacc tgtatcggat gaca                                           24

<210> SEQ ID NO 9
<211> LENGTH: 22
<212> TYPE: DNA
<213> ORGANISM: Pea-Pisum sativum

<400> SEQUENCE: 9
gagcccagaa caggagctaa ca                                             22

<210> SEQ ID NO 10
<211> LENGTH: 25
<212> TYPE: DNA
<213> ORGANISM: Pea-Pisum sativum

<400> SEQUENCE: 10
gcagaaaaac cctatcctcc gtgct                                          25

<210> SEQ ID NO 11
<211> LENGTH: 20
<212> TYPE: DNA
<213> ORGANISM: Pea-Pisum sativum

<400> SEQUENCE: 11
gctccaaagc tccgtagtcg                                                20

<210> SEQ ID NO 12
<211> LENGTH: 20
<212> TYPE: DNA
<213> ORGANISM: Pea-Pisum sativum

<400> SEQUENCE: 12
ctgtactcgc tgttggggtg                                                20

```
<210> SEQ ID NO 13
<211> LENGTH: 20
<212> TYPE: DNA
<213> ORGANISM: Pea-Pisum sativum

<400> SEQUENCE: 13
gcatggatat ggaagccgtg                                               20

<210> SEQ ID NO 14
<211> LENGTH: 20
<212> TYPE: DNA
<213> ORGANISM: Pea-Pisum sativum

<400> SEQUENCE: 14
aatggccgaa agcattgcca                                               20

<210> SEQ ID NO 15
<211> LENGTH: 24
<212> TYPE: DNA
<213> ORGANISM: Pea-Pisum sativum

<400> SEQUENCE: 15
aaggacggtg atgccgatgg actc                                          24

<210> SEQ ID NO 16
<211> LENGTH: 21
<212> TYPE: DNA
<213> ORGANISM: Wheat-Triticum aestivum

<400> SEQUENCE: 16
acatcaagcg cggcaacttc a                                             21

<210> SEQ ID NO 17
<211> LENGTH: 23
<212> TYPE: DNA
<213> ORGANISM: Wheat-Triticum aestivum

<400> SEQUENCE: 17
gagccgcttc ttgaggtggg tgt                                           23

<210> SEQ ID NO 18
<211> LENGTH: 20
<212> TYPE: DNA
<213> ORGANISM: Wheat-Triticum aestivum

<400> SEQUENCE: 18
ccagggagga cggacaacga                                               20

<210> SEQ ID NO 19
<211> LENGTH: 20
<212> TYPE: DNA
<213> ORGANISM: Wheat-Triticum aestivum

<400> SEQUENCE: 19
ctctgcgccg tctcgaagga                                               20
```

ENDOPHYTIC MICROBIAL SYMBIONTS IN PLANT PRENATAL CARE

CROSS REFERENCE TO RELATED APPLICATIONS

This application is a continuation of U.S. patent application Ser. No. 14/766,065, filed Aug. 5, 2015, (pending), which is the National Stage of International Application No. PCT/CA2013/000091, filed Feb. 5, 2013, both of which is herein incorporated in its entirety by reference.

SEQUENCE LISTING

The instant application contains a Sequence Listing with 19 sequences which was submitted via EFS-Web on Dec. 20, 2018 and incorporated by reference in its entirety. Said ASCII copy, created on Dec. 20, 2018 is named 42397_US_Sequece_Listing.txt, and is 9675 bytes in size.

FIELD

The present disclosure relates to fungal and bacterial endophytes of plants that enhance seed vitality and/or plant health, conferring general improvements in the plants agricultural traits, under normal and stressed conditions. The disclosure also relates to these isolated endophytes.

BACKGROUND

Fungi and bacteria are ubiquitous microorganisms. Endophyte is the term first coined by de Bary [1866] defining those microbes that colonize asymptomatically plant tissues [Stone et al., 2000]. The existence of endophytes has been known for more than one century [Freeman 1904] and it seems that each individual host, among the 300,000 plant species, inhabits several to hundreds of endophytes [Tan and Zou, 2001]. Endophytes are microbial organisms mostly symbiotically or mutualistically associated with living tissues of plant hosts. Many are capable of conferring plant tolerance to abiotic stressors or can be used by the plant for defense against pathogenic fungi and bacteria [Singh et al. 2011]. Some of these microorganisms have proven useful for agriculture, forestry and horticulture sectors, as well as plant production of medicinally important compounds.

Endophytes largely determine plant cell and whole plant genome regulation, including plant's vital cycles: (i) seed pre- and post-germination events (mycovitalism) [Vujanovic and Vujanovic 2007], (ii) plant nutrient uptake and growth-promoting mechanisms (mycoheterotrophism) [Smith and Read 2008], and (iii) plant environmental stress tolerance and induced systemic resistance against diseases and pests (mycosymbionticism) [Wallin 1927; Margulis, 1991]. They could play a major role in plant biomass production, $CO_2$ sequestration, and/or yield and therefore be significant players in regulating the ecosphere, ensuring plant health and food security. In addition, they can be important sentinels (bioindicators) of environmental changes, as alterations in the structure and biomass of endophytic communities can herald changes not only in pathways of nutrient (N, P, K), energy transfer in food-webs and biogeochemical cycles but also in UV-B, heat, drought or salt tolerance influencing the overall plant ecosystem establishment and stability. Despite their abundance and likely importance in all terrestrial ecosystems, nearly nothing about the composition of endophytes in seeds or spermosphere, their interactions, or their common response to environmental changes is known.

While the spermosphere represents a rapidly changing and microbiologically dynamic zone of soil surrounding a germinating seed [Nelson, 2004], the rhizosphere is a microbiologically active zone of the bulk soil surrounding the plants roots [Smith and Read 2008]. The rhizosphere supports mycoheterotrophy or a plant-mycorrhiza symbiotic relationship. The spermosphere, on the other hand, promotes mycovitality or an endophytic fungi relationship with the plant seeds—enhancing seed vigour, energy and uniformity of germination that could be fairly predicted. Fungal endophytes are distinct from mycorrhizae in that they can colonize not only roots, but also other plant organs including seeds [Vujanovic et al. 2000; Hubbard et al. 2011]. They belong to the multicellular phyla Ascomycota and Basidiomycota and form colonization symbiotic structures different from those produced by unicellular or cenocytic phylum Glomeromycota, known as vesicular-arbuscular mycorrhizal symbiosis [Abdellatif et al. 2009]. Endophytic bacteria have been also found in virtually every plant studied, where they colonize an ecological niche similar to that of fungi, such as the internal healthy tissues. Although most bacterial endophytes appear to originate from the rhizosphere or phyllosphere; some may be transmitted through the seed [Ryan et al. 2008].

Seed germination is a vital phenophase to plants' survival and reproduction in either optimal or stressful environmental conditions. Microbial endophytic colonization at the seed state is especially critical because of the role of the seed as a generative organ in regeneration and dispersion of flowering plants [Baskin and Baskin 2004] and the role of mycobionts and symbiotically associated bacteria (bactobionts) as potential drivers of seedling recruitment in natural—undisturbed, disturbed and polluted—habitats [Mühlmann and Peintner 2000; Adriaensen et al. 2006; White and Torres 2010]. Thus, developing methods by which seedling emergence can be enhanced and protected under the limitations of disease pressure, heat or drought is precious. The use of endophytic symbionts is a promising method by which seed germination can be enhanced [Vujanovic et al. 2000; Vujanovic and Vujanovic 2006; Vujanovic and Vujanovic 2007]. It was hypothesized that plant stress hardiness can be conferred via a mycobiont-seed relationship known as mycovitality—a phenomenon that had been reserved for Orchidaceae [Vujanovic 2008] and via bactovitality which refers to a form of bactosymbiosis, using different endophytic strains with variety of activities.

SUMMARY

Endophytes can benefit plant hosts such as wheat, barley, pulses, canola, tree, shrub or grass in a variety of ways, including bactovitality, mycovitality and mycoheterotrophy, and enhanced tolerance to environmental stresses, as demonstrated herein. Prenatal care in agriculture, as demonstrated herein with six endophytic strains, is more than just seed or germinant vitality, health or vigour. It also determines what to expect before and during the germination process, seedling establishment, and, later crop productivity or yield.

Several parameters of symbiotic efficacy (dormancy breakdown, germination, growth and yield) were assessed using efficient endophytic Saskatchewan Microbial Collection and Database (SMCD) strain(s)-crop(s) interaction(s) under in vitro, phytotron, greenhouse and field conditions.

Also tested was the bacterial endophyte capacity to confer seed vitality. For both fungal and bacterial endosymbionts, improved seed vitality can increase tolerance for abiotic and biotic stresses in plants that have progressed beyond the seedling stage to the plants maturity via mycoheterotrophy.

Accordingly, the present disclosure provides an isolated endophyte of *Streptomyces* sp. strain or culture thereof which is deposited under the International Depositary Authority of Canada (IDAC, National Microbiology Laboratory. Public Health Agency of Canada. 1015 Arlington Street, Winnipeg, Manitoba, Canada, R3E 3R2) accession number 081111-06 or which comprises the 16S rDNA sequence as shown in SEQ ID NO:6; an isolated endophyte of *Paraconyothirium* sp. strain or culture thereof which is deposited as IDAC accession number 081111-03 or which comprises the ITS rDNA sequence as shown in SEQ ID NO:5; an isolated endophyte of *Pseudeurotium* sp. or culture thereof which is deposited under IDAC accession number 081111-02 or which comprises the ITS rDNA sequence as shown in SEQ ID NO:4; an isolated endophyte of *Penicillium* sp. or culture thereof which is deposited under IDAC accession number 081111-01 or which comprises the ITS rDNA sequence as shown in SEQ ID NO:3; an isolated culture of *Cladosporium* sp. which is deposited under IDAC accession number 200312-06 or which comprises the ITS rDNA sequence as shown in SEQ ID NO:1, and/or an isolated endophyte of *Cladosporium* sp. or culture thereof which is deposited under IDAC accession number 200312-05 or which comprises the ITS rDNA sequence as shown in SEQ ID NO:2.

Also provided herein is a composition comprising an isolated endophyte or culture disclosed herein or a combination or mixture thereof and a carrier.

Further provided herein is a seed comprising an endophyte or culture disclosed herein. In one embodiment, the seed is coated with the endophyte. In another embodiment, the seed is cultured or planted near the endophyte such that the endophyte is able to colonize the seed.

The present disclosure also provides methods for improving seed vitality and enhancing plant health and yield under normal and stressed conditions. Accordingly, there is provided a method of improving seed vitality, plant health and/or plant yield comprising inoculating a seed with an endophyte or culture disclosed herein or a combination or mixture thereof or with a composition disclosed herein; and cultivating the seed into a first generation plant.

In one embodiment, the method comprises inoculating the seed with an isolated endophyte or culture thereof of *Streptomyces* sp. strain which is deposited under IDAC 081111-06 or which comprises the 16S rDNA sequence as shown in SEQ ID NO:6. In an embodiment, the method increases seed germination, decreases time to reach energy of germination, reduces hydrothermal time required for germination, increases seed germination vigour, increases the fresh weight of seedlings, enhances *Rhizobium* activity and nodulation frequency, and/or increases the yield of seedlings. In another embodiment, the method comprises reducing the effects of stress, such as drought, heat and/or biotic stress, such as *Fusarium* infection.

In another embodiment, the method comprises inoculating the seed with an isolated endophyte or culture thereof of *Paraconyothirium* sp. strain which is deposited as IDAC 081111-03 or which comprises the ITS rDNA sequence as shown in SEQ ID NO:5. In an embodiment, the method increases seed germination, decreases time to reach energy of germination, reduces hydrothermal time required for germination, increases seed germination vigour, increases the fresh weight of seedlings and/or increases yield of seedlings. In another embodiment, the method comprises reducing the effects of stress, such as drought, heat and/or biotic stress, such as *Fusarium* infection.

In yet another embodiment, the method comprises inoculating the seed with an isolated endophyte or culture thereof of *Pseudeurotium* sp. which is deposited under IDAC 081111-02 or which comprises the ITS rDNA sequence as shown in SEQ ID NO:4. In an embodiment, the method decreases time to reach energy of germination, reduces hydrothermal time required for germination, increases seed germination vigour, and/or increases the fresh weight of seedlings. In another embodiment, the method comprises reducing the effects of stress, such as drought and/or heat stress.

In a further embodiment, the method comprises inoculating the seed with an isolated endophyte or culture thereof of *Penicillium* sp. which is deposited under IDAC 081111-01 or which comprises the ITS rDNA sequence as shown in SEQ ID NO:3. In an embodiment, the method increases seed germination, decreases time to reach energy of germination, reduces hydrothermal time required for germination, increases seed germination vigour, and/or increases yield of seedlings. In another embodiment, the method comprises enhancing stratification, breaking dormancy and increasing stress resistance by modulating hormonal ent-kaurenoic (KAO), repression of shoot growth (RSG), abscisic acid (ABA), gibberellic acid GA, 14-3-3 or nitric oxide (NO) genes and/or stress resistance superoxide dismutase (SOD), manganese SOD (MnSOD), proline (Pro) or MYB genes expressions, reducing the effects of stress, such as drought, heat and/or biotic stress, such as *Fusarium* infection.

In yet a further embodiment, the method comprises inoculating the seed with an isolated endophyte or culture thereof of *Cladosporium* sp. which is deposited under IDAC 200312-06 or which comprises the ITS rDNA sequence as shown in SEQ ID NO:1. In an embodiment, the method decreases time to reach energy of germination, reduces hydrothermal time required for germination, increases seed germination vigour, and/or increases the fresh weight of seedlings. In an embodiment, the method comprises reducing the effects of stress, such as drought and/or heat.

In yet another further embodiment, the method comprises inoculating the seed with an isolated endophyte or culture thereof of *Cladosporium* sp. which is deposited under IDAC 200312-05 or which comprises the ITS rDNA sequence as shown in SEQ ID NO:2. In an embodiment, the method comprises reducing the effects of stress, such as drought and/or heat stress.

In an embodiment, the seed is coated with the endophyte, cultured with the endophyte or planted near the endophyte. In a particular embodiment, the seed planted near the endophyte is about 4 cm away from the endophyte.

The plant may be any plant. In one embodiment, the plant is a cereal (wheat or barley), pulse (pea, lentil or chickpea), flax, canola plant, coniferous tree (spruce or pine), broadleaf tree (willow or poplar), shrub (caragana or winterfat) or grass (fescue or wildrye).

In another aspect, there is provided a method of improving plant health and/or plant yield comprising treating plant propagation material or a plant with an endophyte or culture disclosed herein or a combination or mixture thereof or a composition disclosed herein; and cultivating the plant propagation material into a first generation plant or allowing the plant to grow.

In an embodiment, the plant propagation material is any plant generative/sexual (seed, generative bud or flower) and vegetative/asexual (stem, cutting, root, bulb, rhizome, tuber, vegetative bud, or leaf) part that has the ability to be cultivated into a new plant.

In an embodiment, the isolated endophyte or culture thereof is an isolated endophyte of *Streptomyces* sp. strain or culture thereof which is deposited under the International Depositary Authority of Canada (IDAC, National Microbiology Laboratory. Public Health Agency of Canada. 1015 Arlington Street, Winnipeg, Manitoba, Canada, R3E 3R2) accession number 081111-06 or which comprises the 16S rDNA sequence as shown in SEQ ID NO:6; an isolated endophyte of *Paraconyothirium* sp. strain or culture thereof which is deposited as IDAC accession number 081111-03 or which comprises the ITS rDNA sequence as shown in SEQ ID NO:5; an isolated endophyte of *Pseudeurotium* sp. or culture thereof which is deposited under IDAC accession number 081111-02 or which comprises the ITS rDNA sequence as shown in SEQ ID NO:4; an isolated endophyte of *Penicillium* sp. or culture thereof which is deposited under IDAC accession number 081111-01 or which comprises the ITS rDNA sequence as shown in SEQ ID NO:3; an isolated culture of *Cladosporium* sp. which is deposited under IDAC accession number 200312-06 or which comprises the ITS rDNA sequence as shown in SEQ ID NO:1, and/or an isolated endophyte of *Cladosporium* sp. or culture thereof which is deposited under IDAC accession number 200312-05 or which comprises the ITS rDNA sequence as shown in SEQ ID NO:2.

In an embodiment, the methods enhance landscape development and remediation. Accordingly, in one embodiment, there is provided a method of reducing soil contamination comprising treating plant propagation material or a plant with an endophyte or culture disclosed herein or a combination or mixture thereof or a composition disclosed herein; and cultivating the plant propagation material into a first generation plant or allowing the plant to grow. In one embodiment, the soil contaminant is hydrocarbons, petroleum or other chemicals, salts, or metals, such as lead, cadmium or radioisotopes.

In another embodiment, the methods reduce the effects of stress, such as heat, drought and/or biotic stress.

The plant may be any plant. In one embodiment, the plant is a cereal (wheat and barley), pulse (pea, lentil or chickpea), flax, canola plant, coniferous tree (spruce or pine), broadleaf tree (willow or poplar), shrub (caragana or winterfat) or grass (fescue or wild rye).

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description and respective drawings and drawing legends.

BRIEF DESCRIPTION OF THE DRAWINGS

The disclosure will now be described in relation to the drawings in which.

DETAILED DESCRIPTION

Novel Strains, Compositions and Seeds

Figure 1:
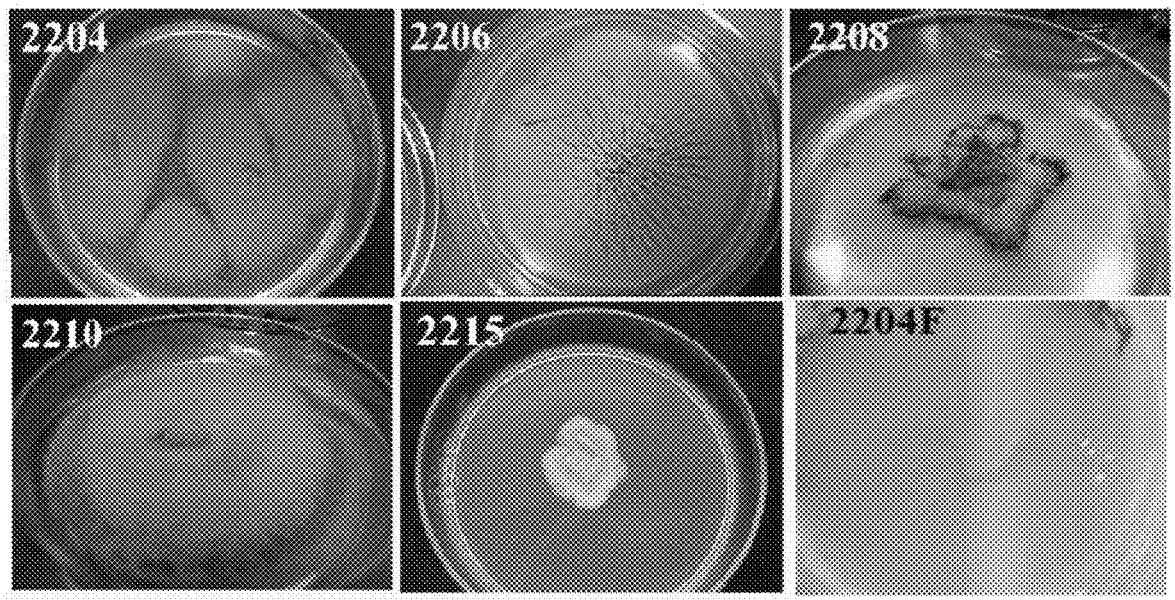
FIG. 1 shows the phenotypic appearance of the endophytic fungal strains SMCD 2204, 2004F, 2206, 2208, and 2210 and bacterial strain SMCD 2215; after 10 days of growth on PDA at 21° C.
Figure 2:
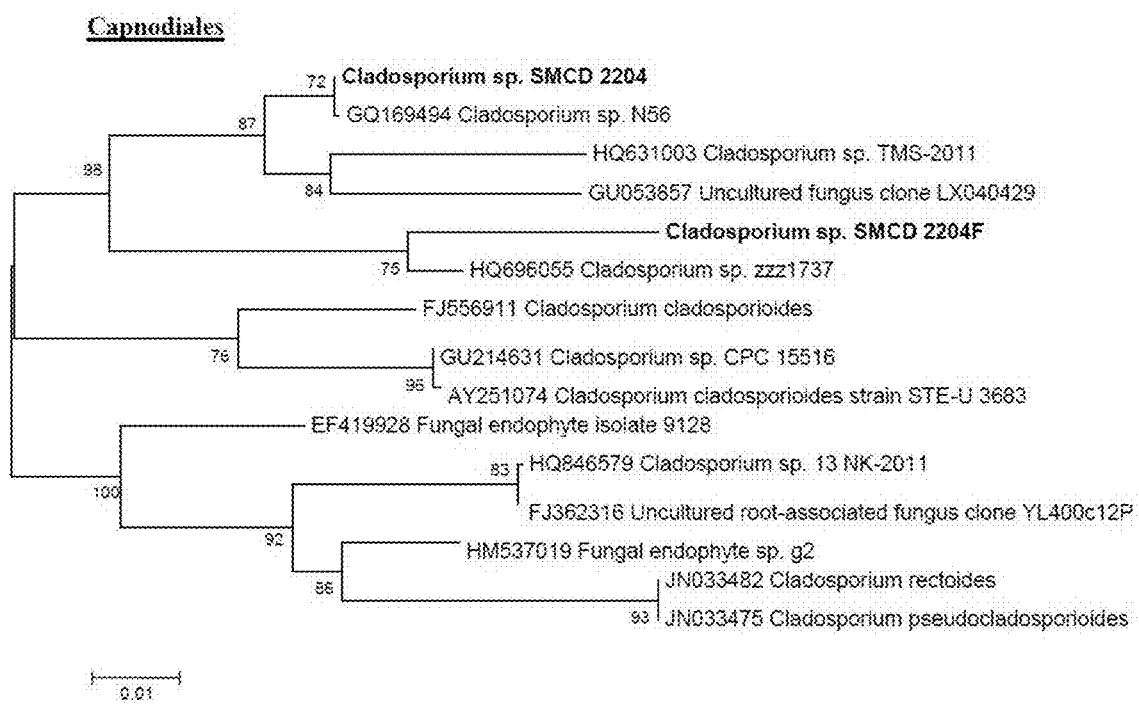
FIG. 2 shows the inferred neighbour-joining phylogenetic tree of the *Cladosporium* spp. SMCD 2204 and SMCD 2204F based on ITS rDNA. Numbers at nodes indicate bootstrap support values for 1000 replicates; only values that were >70% are given. Bar indicates 0.01 nucleotide substitutions per site (nucleotide position).
Figure 3:
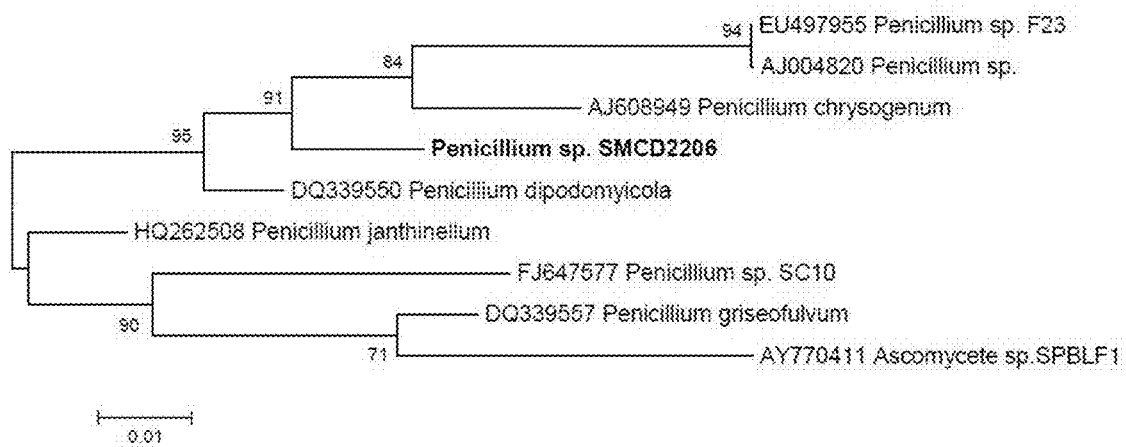
FIG. 3 shows the inferred neighbour-joining phylogenetic tree of the *Penicillium* sp. SMCD 2206 based on ITS rDNA. Numbers at nodes indicate bootstrap support values for 1000 replicates; only values that were >70% are given. Bar indicates 0.01 nucleotide substitutions per site (nucleotide position).
Figure 4:
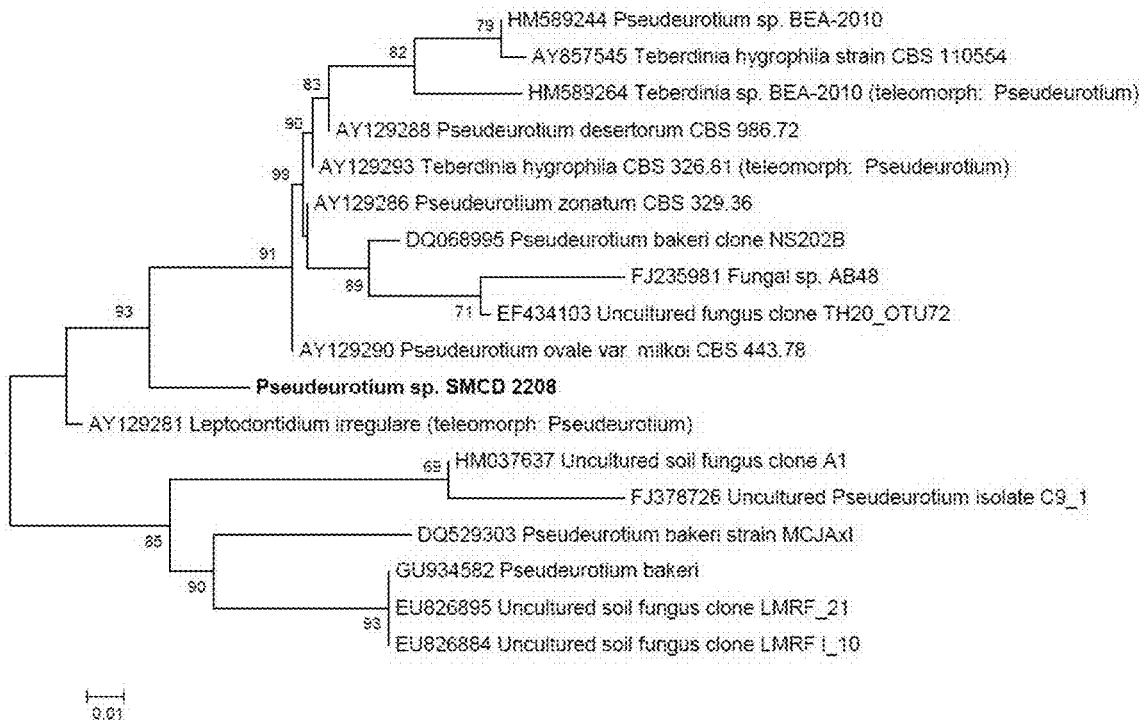
FIG. 4 shows the inferred neighbour-joining phylogenetic tree of the *Pseudeurotium* sp. SMCD 2208 based on ITS rDNA. Numbers at nodes indicate bootstrap support values for 1000 replicates; only values that were >70% are given. Bar indicates 0.01 nucleotide substitutions per site (nucleotide position).
Figure 5:
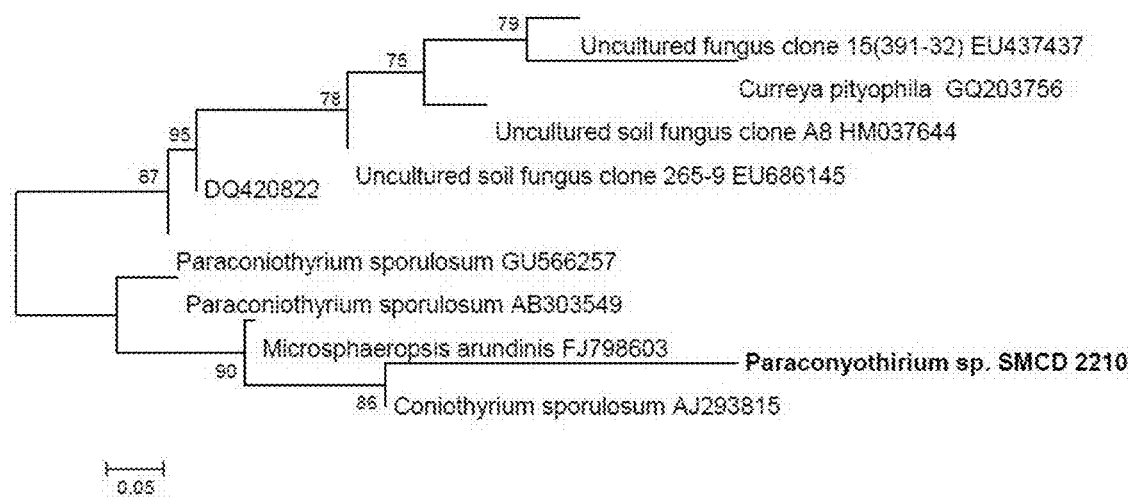
FIG. 5 shows the inferred neighbour-joining phylogenetic tree of the *Coniothyrium* strain SMCD 2210 based on ITS rDNA. Numbers at nodes indicate bootstrap support values for 1000 replicates; only values that were >70% are given. Bar indicates 0.05 nucleotide substitutions per site (nucleotide position).
Figure 6:
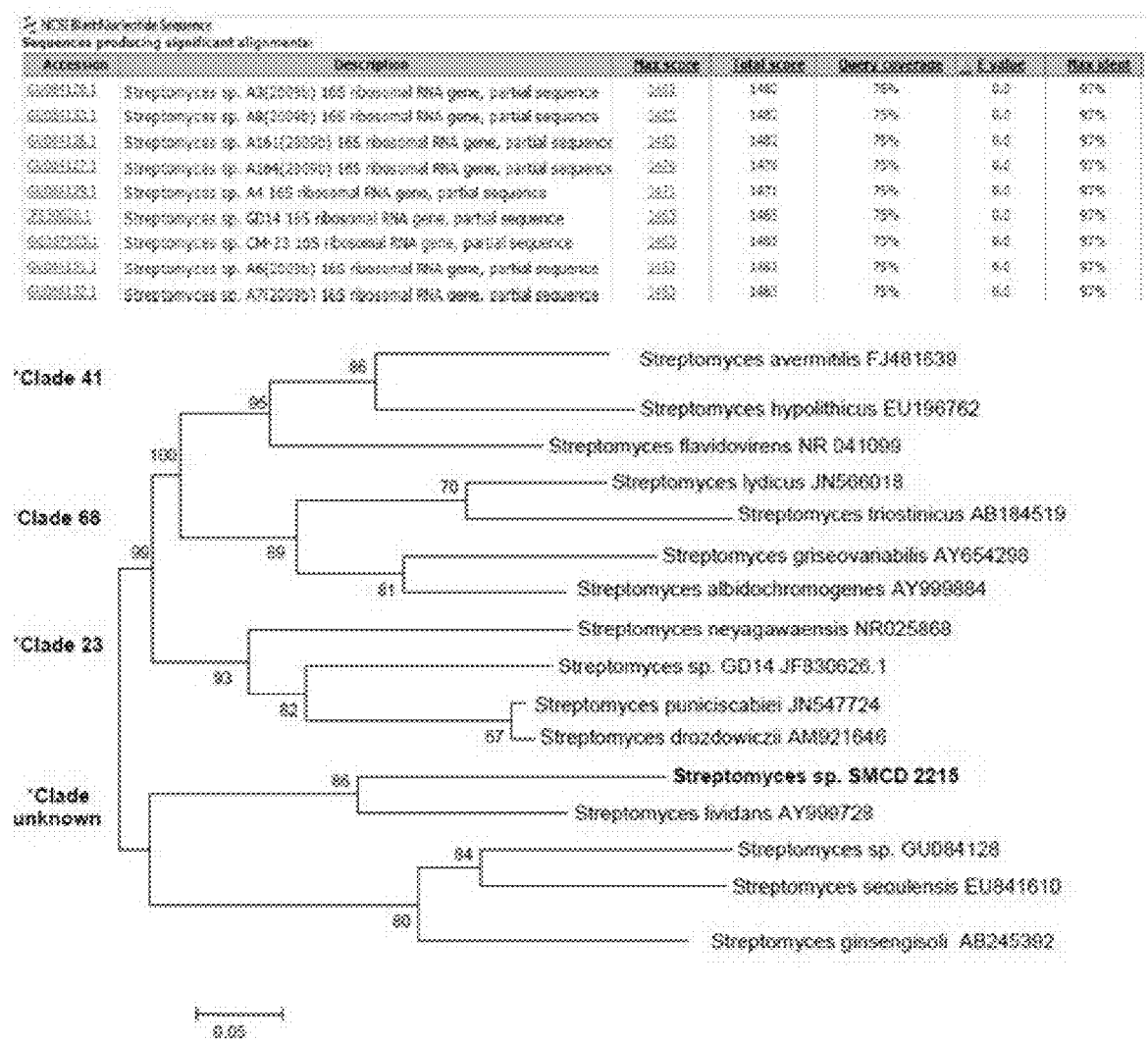
FIG. 6 shows the inferred neighbour-joining phylogenetic tree of the *Streptomyces* sp strain SMCD 2215 based on 16S rDNA. Numbers at nodes indicate bootstrap support values for 1000 replicates; only values that were >60% are given. Bar indicates 0.05 nucleotide substitutions per site (nucleotide position).

The present inventors have isolated 6 novel endophyte strains that enhance seed vitality and plant health and yield under normal and/or stressed conditions. These endophytes have been deposited as follows: International Depository Authority of Canada—IDAC (original strains deposited—IDAC, National Microbiology Laboratory, Public Health Agency of Canada, 1015 Arlington Street, Winnipeg, Manitoba, Canada, R3E 3R2; receipts and viability in Appendix A) and Saskatchewan Microbial Collection and Database—SMCD (copies of strains deposited) Strains:

(a) IDAC 081111-06=SMCD 2215;
(b) IDAC 081111-03=SMCD 2210;

(c) IDAC 081111-02=SMCD 2208;
(d) IDAC 081111-01=SMCD 2206;
(e) IDAC 200312-06=SMCD 2204; and
(f) IDAC 200312-05=SMCD 2204F.

Accordingly, the present disclosure provides an isolated endophyte of *Streptomyces* sp. strain or culture thereof which is deposited under IDAC 081111-06 or which comprises the 16S rDNA sequence as shown in SEQ ID NO:6; an isolated endophyte of *Paraconyothirium* sp. strain or culture thereof which is deposited as IDAC 081111-03 or which comprises the ITS rDNA sequence as shown in SEQ ID NO:5; an isolated endophyte of *Pseudeurotium* sp. or culture thereof which is deposited under IDAC 081111-02 or which comprises the ITS rDNA sequence as shown in SEQ ID NO:4; an isolated endophyte of *Penicillium* sp. or culture thereof which is deposited under IDAC 081111-01 or which comprises the ITS rDNA sequence as shown in SEQ ID NO:3; an isolated culture of *Cladosporium* sp. which is deposited under IDAC 200312-06 or which comprises the ITS rDNA sequence as shown in SEQ ID NO:1; and/or an isolated endophyte of *Cladosporium* sp. or culture thereof which is deposited under IDAC 200312-05 or which comprises the ITS rDNA sequence as shown in SEQ ID NO:2; or combinations or mixtures thereof.

The term "endophyte" as used herein refers to a fungal or bacterial organism that can live symbiotically in a plant and is also referred to herein as "endosymbiont". A fungal endophyte may be in the form of a spore, hypha, or mycelia. A bacterial endophyte may be a cell or group of cells. The term "endophyte" as used herein includes progeny of the strains recited herein.

Also provided herein is a composition comprising an isolated endophyte or culture disclosed herein or a combination or mixture thereof and a carrier. Typical carriers include, without limitation, an inert (non-carbon based) material used to support and deliver the densely populated active ingredient to the target, and optionally adjuvants—compounds that; promote and sustain the function of the active ingredient by protection from UV radiation; ensure rain fastness on the target; retain moisture or protect against desiccation; and/or promote the spread and dispersal of the biopesticide using standard agriculture equipments such as those disclosed by Hynes and Boyetchko (2006, Soil Biology & Biochemistry 38: 845-84).

In another embodiment, the compositions comprises at least 2, at least 3, at least 4, at least 5 or 6 of the endophyte strains or cultures disclosed herein.

Further provided herein is a seed comprising an endophyte or culture disclosed herein or a combination or mixture thereof.

In one embodiment, the seed is inoculated by soil based inoculation. In another embodiment, the seed is coated with the endophyte or culture thereof. In yet another embodiment, the seed is sprayed, injected, inoculated, grafted, coated or treated with the endophyte or culture thereof.

Methods

Further provided herein is a method of enhancing seed vitality, plant health and/or yield comprising inoculating a seed with an endophyte or culture disclosed herein or a combination or mixture thereof or with a composition disclosed herein; and cultivating a first generation plant from the seed.

The phrase "inoculating a seed" as used herein refers to applying, infecting, co-planting or coating the seed with the endophyte. Techniques for inoculating the seed are known in the art, for example, as disclosed by Hynes and Boyetchko (2006, Soil Biology & Biochemistry 38: 845-84).

The term "enhancing seed vitality" as used herein refers to plant prenatal care improving the ability of the seed to germinate and produce a plant under normal and/or stressed conditions and includes, without limitation, any one or more of the following: breaking dormancy, providing seed stratification, increasing seed germination, modulating gene expression, decreasing time to reach energy of germination, protecting against biotic stresses, protecting against abiotic stresses, reducing hydrothermal time required for germination, increasing seed germination vigour, increasing seed germination efficacy, increasing uniformity of seed germination, ameliorating drought/heat tolerance efficacy, increasing the weight of seedlings, and increasing the yield of seedlings. Drought/Heat Tolerance Efficiency (DTE/THE) is the term opposed (antonym) to susceptibility.

Energy of germination is defined as 50% of germination, relative to the number of seeds tested. The seed germination vigour shows the difference between total percentage of germinating treated seeds and germinating untreated seeds. The hydrothermal time postulates that an individual seed begins to germinate when the sum of both temperatures and water potential are sufficiently accumulated over a period of time allowing germination. Germination efficacy is defined as the percentage of treated seeds germinating after a set time period after planting, relative to the number of seeds tested in an untreated control. Biological stratification is defined as releasing seed dormancy by a symbiont in promoting germination. Uniformity of seed germination represents the maximum percentage of seed germination within a minimal time of incubation.

The term "enhancing plant health and/or yield" as used herein refers to general improvements in the plant agricultural traits (e.g. health and productivity) of the resulting plant under normal and/or stressed conditions and includes without limitation, any one or more of the following: modulating gene expression of RSG, KAO, ABAs, GAs, 14-3-3 or NO to improve plant hormonal activities, modulating gene expression of MYBs, Pro, SOD, or MnSOD to enhance stress resistance, such as resistance to abiotic and biotic stresses, increasing the weight of the various tissues, such as root, stem, leaves and pods, increasing *Rhizobium* activity and nodulation frequency and improving the characteristics of the first or subsequent generation seeds, including, without limitation, any one or more of the following: subsequent generation seed weight and subsequent generation energy of germination.

Hormonal KAO, RSG, ABAs, GAs, 14-3-3 genes and primer sets are as disclosed by Zhang et al. [2007]. Stress resistance SOD, MnSOD, Pro and MYB genes and primer sets are presented in Table 6 and Table 9 (SEQ ID NO: 8-19).

The term "decreasing" or "increasing" as used herein refers to a decrease or increase in a characteristic of the endophyte treated seed or resulting plant compared to an untreated seed or resulting plant. For example, a decrease in a characteristic may be at least 5%, 10%, 15%, 25%, 50%, 75%, 100%, or 200% or more lower than the untreated control and an increase may be at least 5%, 10%, 15%, 25%, 50%, 75%, 100%, or 200% or more higher than the untreated control.

In one embodiment, the plant is cultivated under abiotic or biotic stressed conditions.

The term "abiotic stress" as used herein refers to a non-living stress that typically affects seed vitality and plant health and includes, without limitation, heat and drought stress. In one embodiment, the abiotic stress is heat stress. In another embodiment, the abiotic stress is drought stress, osmotic stress or salt stress. The term "biotic stress" as used herein refers to a living stress that typically affects seed vitality and plant health, and includes without limitation, microbial plant infections. In one embodiment, the biotic stress is a *Fusarium* infection.

In one embodiment, the method comprises inoculating the seed with an isolated endophyte or culture thereof of *Streptomyces* sp. strain which is deposited under IDAC 081111-06 or which comprises the 16S rDNA sequence as shown in SEQ ID NO:6. In an embodiment, the method increases seed germination, for decreasing time to reach energy of germination, for reducing hydrothermal time required for germination, for increasing seed germination vigour, for increasing the fresh weight of seedlings, for increasing *Rhizobium* activity and nodulation frequency and/or for increasing yield of seedlings. In one embodiment, the method comprises reducing the effects of stress, such as drought, heat and/or biotic stress.

In another embodiment, the method comprises inoculating the seed with an isolated endophyte or culture thereof of *Paraconyothirium* sp. strain which is deposited as IDAC 081111-03 or which comprises the ITS rDNA sequence as shown in SEQ ID NO:5. In an embodiment, the method increases seed germination, decreases time to reach energy of germination, reduces hydrothermal time required for germination, increases seed germination vigour, increases the fresh weight of seedlings and/or increases yield of seedlings. In another embodiment, the method comprises reducing the effects of stress, such as drought, heat and/or biotic stress.

In yet another embodiment, the method comprises inoculating the seed with an isolated endophyte or culture thereof of *Pseudeurotium* sp. which is deposited under IDAC 081111-02 or which comprises the ITS rDNA sequence as shown in SEQ ID NO:4. In an embodiment, the method decreases time to reach energy of germination, reduces hydrothermal time required for germination, increases seed germination vigour, and/or increases fresh weight of seedlings. In another embodiment, the method comprises reducing the effects of stress, such as drought and/or heat stress.

In a further embodiment, the method comprises inoculating the seed with an isolated endophyte or culture thereof of *Penicillium* sp. which is deposited under IDAC 081111-01 or which comprises the ITS rDNA sequence as shown in SEQ ID NO:3. In an embodiment, the method increases seed germination, decreases time to reach energy of germination, reduces hydrothermal time required for germination, increases seed germination vigour, and/or increases yield of seedlings. In another embodiment, the method comprises reducing the effects of stress, such as drought, heat and/or biotic stress. In another embodiment, the method comprises enhancing stratification, breaking dormancy and increasing stress resistance by modulating hormonal KAO, RSG, ABAs, GAs, 14-3-3 or NO genes and/or stress resistance SOD, MnSOD, Pro or MYB gene expressions, reducing the effects of stress, such as drought, heat and/or biotic stress.

In yet a further embodiment, the method comprises inoculating the seed with an isolated endophyte or culture thereof of *Cladosporium* sp. which is deposited under IDAC 200312-06 or which comprises the ITS rDNA sequence as shown in SEQ ID NO:1. In an embodiment, the method decreases time to reach energy of germination, reduces hydrothermal time required for germination, increases seed germination vigour, and/or increases the fresh weight of seedlings. In an embodiment, the method comprises reducing the effects of stress, such as drought and/or heat.

In yet another further embodiment, the method comprises inoculating the seed with an isolated endophyte or culture thereof of *Cladosporium* sp. which is deposited under IDAC 200312-05 or which comprises the ITS rDNA sequence as shown in SEQ ID NO:2. In an embodiment, the method comprises reducing the effects of stress, such as drought and/or heat stress.

The term "plant" as used herein refers to a member of the Plantae Kingdom and includes all stages of the plant life cycle, including without limitation, seeds. In one embodiment, the plant is a cereal (wheat and barley), pulse (pea, lentil or chickpea), flax, or canola plant.

In an embodiment, the seed is coated with the endophyte, cultured with the endophyte or planted near the endophyte. In a particular embodiment, the seed planted near the endophyte is about 4 cm away from the endophyte.

In another aspect, there is provided a method of improving plant health and/or plant yield comprising treating plant propagation material or a plant with an endophyte or culture disclosed herein or a combination or mixture thereof or with a composition disclosed herein; and cultivating the plant propagation material into a first generation plant or allowing the plant to grow.

The term "plant propagation material" as used herein refers to any plant generative/sexual and vegetative/asexual part that has the ability to be cultivated into a new plant. In an embodiment, the plant propagation material is generative seed, generative bud or flower, and vegetative stem, cutting, root, bulb, rhizome, tuber, vegetative bud, or leaf parts.

In an embodiment, the isolated endophyte or culture thereof is an isolated endophyte of *Streptomyces* sp. strain or culture thereof which is deposited under the International Depositary Authority of Canada (IDAC, National Microbiology Laboratory. Public Health Agency of Canada. 1015 Arlington Street, Winnipeg, Manitoba, Canada, R3E 3R2) accession number 081111-06 or which comprises the 16S rDNA sequence as shown in SEQ ID NO:6; an isolated endophyte of *Paraconyothirium* sp. strain or culture thereof which is deposited as IDAC accession number 081111-03 or which comprises the ITS rDNA sequence as shown in SEQ ID NO:5; an isolated endophyte of *Pseudeurotium* sp. or culture thereof which is deposited under IDAC accession number 081111-02 or which comprises the ITS rDNA sequence as shown in SEQ ID NO:4; an isolated endophyte of *Penicillium* sp. or culture thereof which is deposited under IDAC accession number 081111-01 or which comprises the ITS rDNA sequence as shown in SEQ ID NO:3; an isolated culture of *Cladosporium* sp. which is deposited under IDAC accession number 200312-06 or which comprises the ITS rDNA sequence as shown in SEQ ID NO:1, and/or an isolated endophyte of *Cladosporium* sp. or culture thereof which is deposited under IDAC accession number 200312-05 or which comprises the ITS rDNA sequence as shown in SEQ ID NO:2.

In another embodiment, the methods reduce the effects of stress, such as heat, drought and/or biotic stress.

In an embodiment, the methods enhance landscape development and remediation.

Accordingly, in one embodiment, there is provided a method of phytoremediation or phytoreclamation of a contaminated site comprising treating plant propagation material or a plant with an endophyte or culture disclosed herein or a combination of mixture thereof or a composition disclosed herein, and cultivating the plant propagation material into a first generation plant or allowing the plant to grow; thereby remediating or reclaiming the site.

The term "phytoremediation" as used herein refers to the use of plants for removal, reduction or neutralization of substances, wastes or hazardous material from a site so as to prevent or minimize any adverse effects on the environment.

The term "phytoreclamation" as used herein refers to the use of plants for reconverting disturbed land to its former or other productive uses.

In one embodiment, the site is soil, such as at a landfill. In an embodiment, the substances, wastes or hazardous materials comprise hydrocarbons, petroleum or other chemicals, salts, or metals, such as lead, cadmium or radioisotopes.

The phrase "treating a plant propagation material or plant" as used herein refers to applying the endophyte or culture thereof alone or with any solid or liquid carrier to the plant propagation material or plant or a part of said plant. In an embodiment, treating comprises foliar application or soil application of the endophyte or combination thereof with any solid or liquid carrier at all growing stages of the plant.

The plant may be any plant. In one embodiment, the plant is a cereal (e.g. wheat or barley), pulse (e.g. pea, lentil or chickpea), flax, canola plant, coniferous tree (e.g. spruce or pine), broadleaf tree (e.g. willow or poplar), shrub (e.g. caragana or winterfat) or grass (e.g. fescue or wild rye).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Examples (1-14)

Dormancy and germination depend on several processes and factors. To ensure seedling establishment and success, it is important to control the underlying processes or conditions. The role of plant genetics, hormones, and different seed tissues have been relatively well studied. The present examples study the endophyte-plant seed relationship, transitting into a root symbiotic stage towards plant maturation.

Example 1

Taxonomy

International Depository Authority of Canada—IDAC (original strains deposited) and Saskatchewan Microbial Collection and Database—SMCD (copies of strains deposited) Strains: IDAC 081111-06=SMCD 2215; IDAC 081111-03=SMCD 2210; IDAC 081111-02=SMCD 2208; IDAC 081111-01=SMCD 2206; IDAC 200312-06=SMCD 2204; IDAC 200312-05=SMCD 2204F (FIGS. 1-6 and Table 1).

SMCD 2215 strain was originally isolated as endophytic bacterium of *Phyalocephala sensu* lato plant endophytic SMCD fungus. Classification according to Labeda et al. [2012]. This phylogenetic study examines almost all described species (615 taxa) within the family Streptomycetaceae based on 16S rDNA gene sequences and illustrates the species diversity within this family, which is observed to contain 130 statistically supported clades.

The present 16S rDNA sequence data confirm that *Streptomyces* sp. strain SMCD 2215 can be assigned to a separate unknown clade according to Labeda et al [2012] but separate species from *Streptomyces lividans*.

Example 2

Symbiotic Microbe-Plant Association and Level of Compatibility

Figure 7:
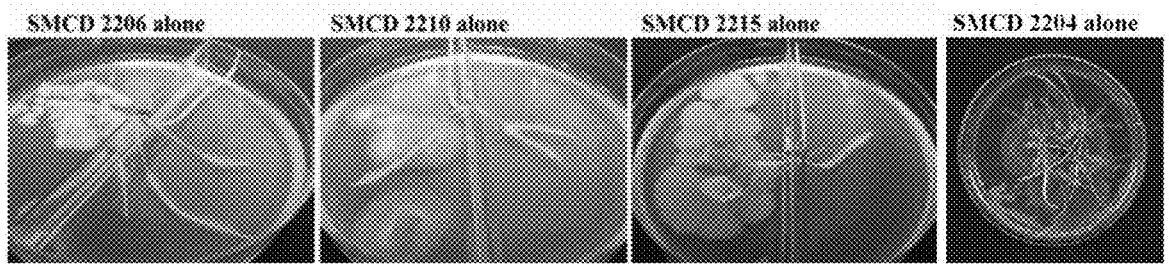
FIG. 7 shows left compartments of split plates (plant with microbial partner): healthy phenotypic appearance of wheat when the root is grown in contact with the microbial mats; and right-compartments of split plates (plant without microbial partner): massive formation of root hairs of wheat due to the plant-fungus association made in the left compartments of the split plates.

The level of microbe-plant compatibility was assessed using a slightly modified method of Abdellatif et al. [2009]. In a bicompartmental agar 10 cm plate without nutrients (FIG. 7), the plants health and the formation of root hairs—the absorbants of water and minerals—were characterized in co-culture, with and without microbial partners. In FIG. 7, the left compartment of each split plate shows a culture with the microbial partner, and the right compartment of each split plate shows a culture without the microbial partner. The experiment was repeated twice in three replicates.

As shown in the left compartment of each split plate, healthy plant tissue formed even when the plant roots were grown directly on the dense microbial mats. The biomass of root hairs is enhanced to about twice as much compared to the right compartment of each split plate where the microbial partner is absent (see left compartments).

Figure 8:
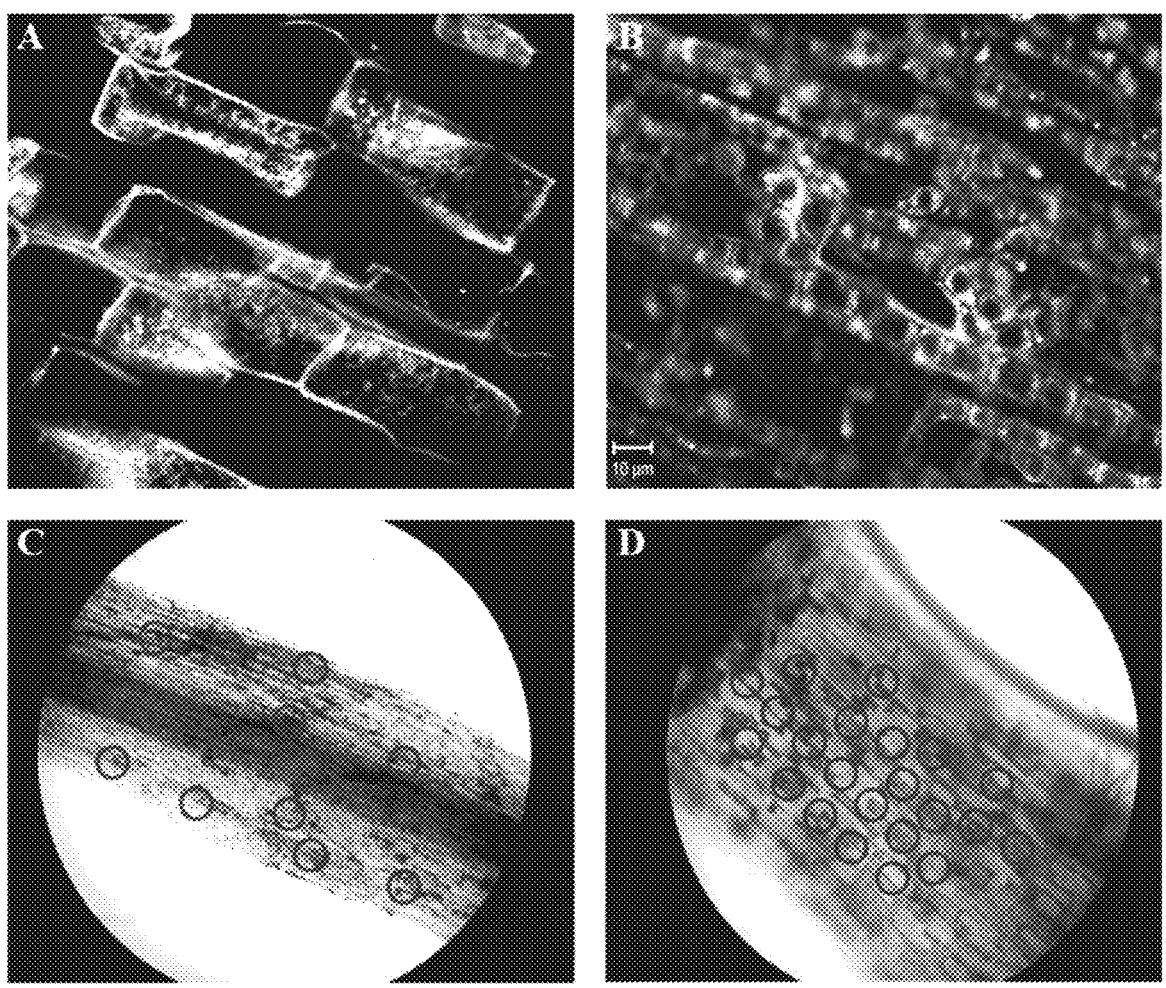
FIGS. 8 (A) and (C) shows SMCD2206 discontinuous colonization of wheat root (epidermis and cortex) tissue compared to (B) and (D) which shows pathogenic *Fusarium graminearum*'s uniform/continual cell colonization of wheat root including vascular cylinder.

The plant efficacy to establish symbiotic association is dependent on the type of endophyte distribution within the root endodermis. Typical endophytic root colonization is discontinuous and partial with a lower number of occupied cells <50% (Table 2) compared to the colonization of fungal pathogens which is characterized by a uniform/continual (frequency: 60-80%) colonization of cells (FIG. 8).

Figure 9:
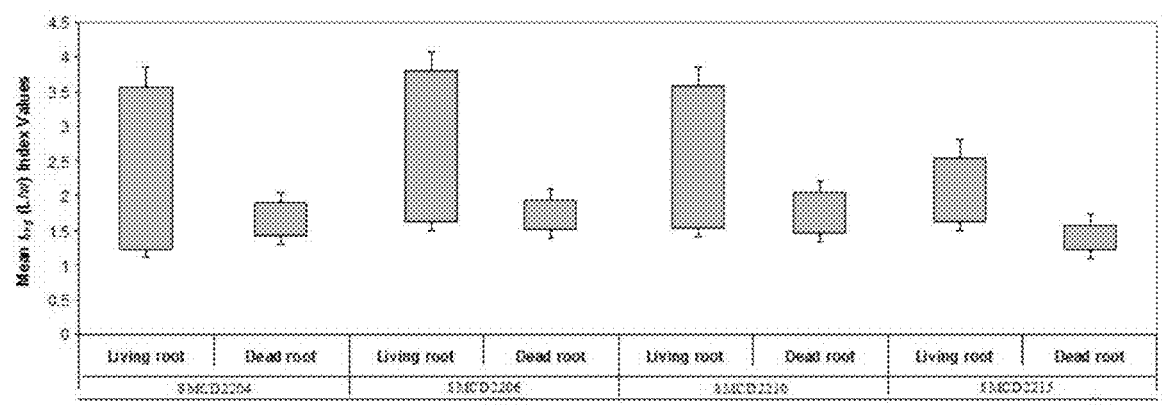
FIG. 9 shows Ireg index—level of deviation (irregularity) in endophyte (SMCDs) cell form.
Figure 10:
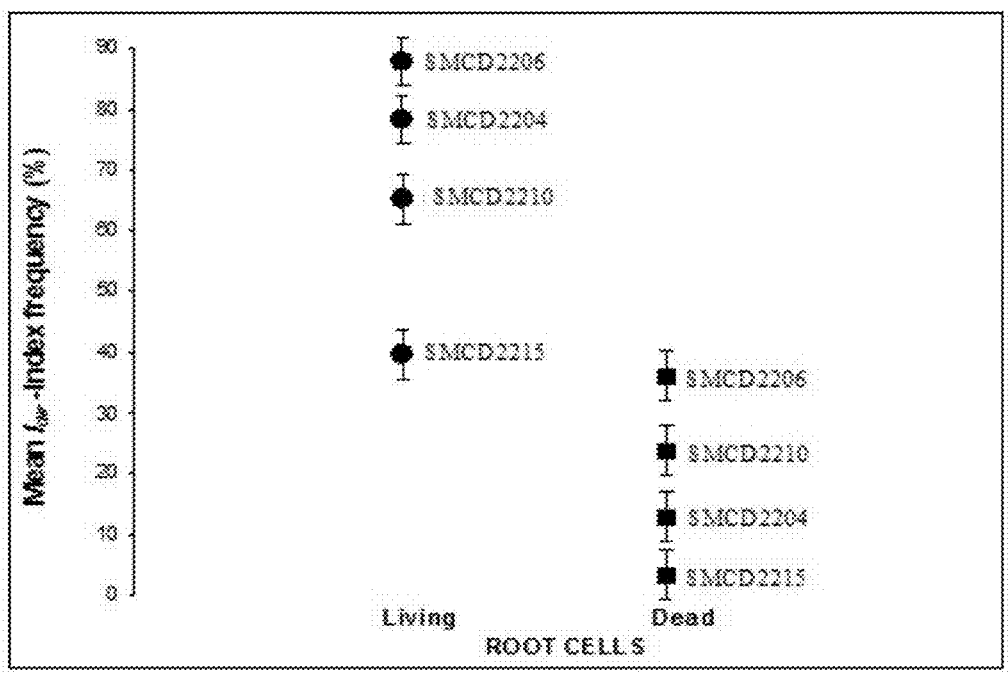
FIG. 10 shows Idir index—level of direction changes when colonizing living plant-host cell.

An endophyte's performance should not only be assessed by measuring biomass production, because what underlies the visibly increased yield is the endophyte's efficiency in colonizing the plant. This can be assessed by characterizing their association with plant cells, tissues, or organs (i.e. seed and radicles) using mathematical Indices which have been developed [Abdellatif et al. 2009] and applied in this study (FIG. 9 and FIG. 10).

These Indices are based on the following observations: Endophytic symbionts show different radicle (root)-colonization patterns (regularity or level of deviation in endophyte cell form-Ireg and direction-Idir when colonizing living cell) compared to dead radicle-cell (which usually remain colonized by true saprophytes).

High Ireg and Idir index values determine mutualistic (beneficial) plant-symbiont relationships. In conclusion, the results show that the symbiotic microbe-plant association is characterised by a high level of compatibility between the two partners, leading to an equilibrated (<50% of colonized cortex cells) and discontinuous root colonisation by the microbial endophytes measured using mathematical indices [Abdellatif et al. 2009]. This mutualistic partnership is further characterised by the direct effect of endophytic microbes on plant healthy growth (bacto- and mycodependency) when the plant is challenged to use the microbial partners as the only source of nutrients or energy for growth. In addition, the enhancement of the root hairs biomass by the endophytes was observed and measured even in roots in distal compartments of split plates where microbial partners were absent, indicating a possible systemic plant growth promoting function of the endophytes.

Example 3

Symbiotic Organs of Endophytes on Wheat

Figure 11:
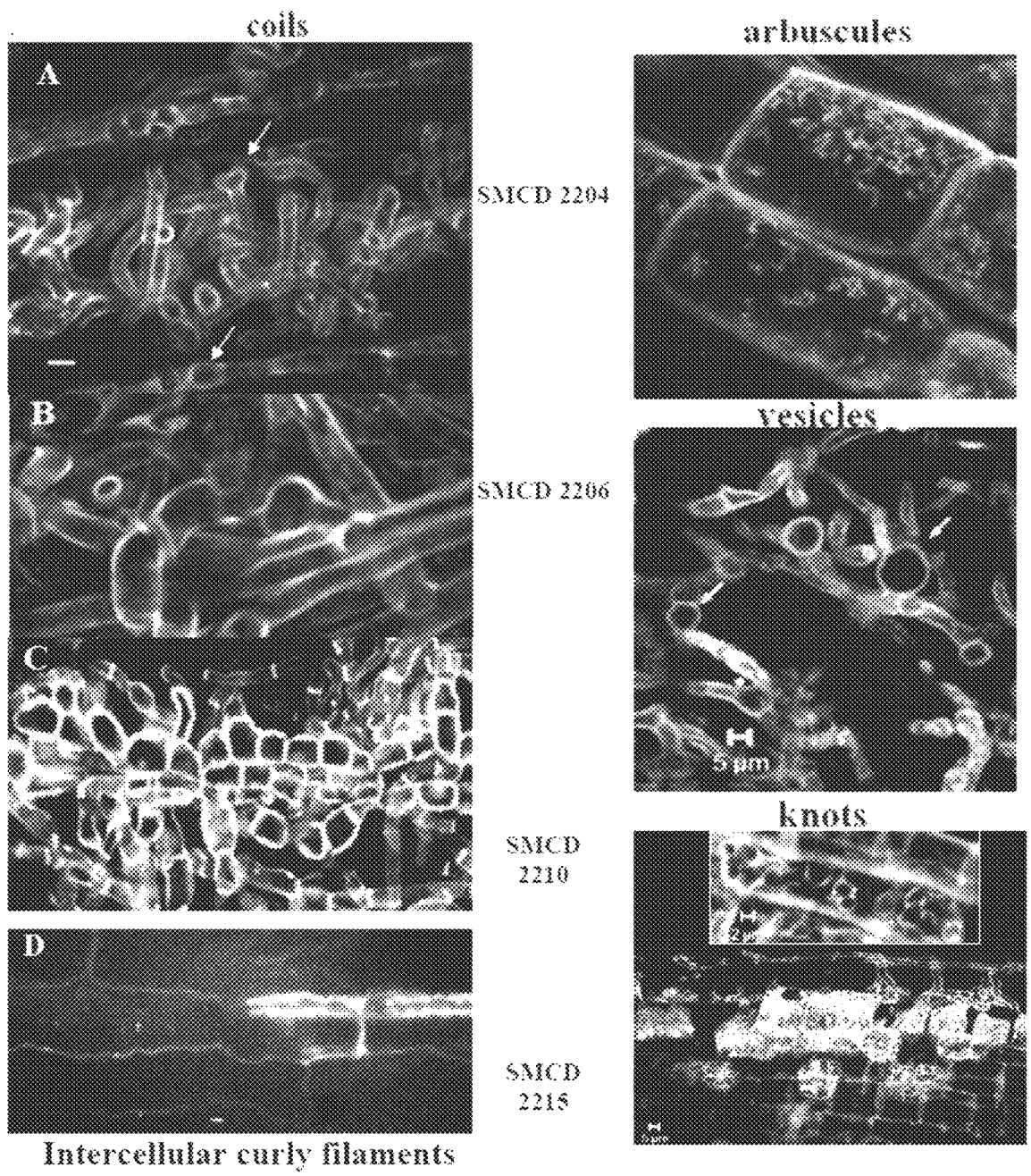
FIG. 11 shows endophytic hyphae in root of wheat germinant (A—SMCD 2204; B—SMCD 2206; C—SMCD 2210; and D—SMCD-2215) visualized with lactofuchsin staining and fluorescence microscopy. Symbiotic structures/organs: (D) SMCD 2215 bacterial endophyte mostly formed curly intercellular filaments, whereas endophytic fungi (Figures to the right) produced: SMCD 2204 intracellular coils and arbuscules, SMCD 2206 intracellular vesicles, and SMCD 2110 intracellular knots.

Each taxonomical group of endophytes establishes a unique type of mycovitalism, consequently forming different symbiotic organs. Characterization of the mycovitalism was done using Abdellatif et al. [2009]methodology, consisting of in vitro seed and microbe co-cultures assessing an early stage of the microbe-plant symbiotic association. The diversity of microbial symbiotic organs formed by SMCD 2204, 2206, 2210, and 2215 on wheat germinants is shown in FIG. 11.

In summary, the results show differential types of symbiotic organs formed in wheat root by each endophyte likely related to their different symbiotic functions. An equilibrated colonization abundance, patchy colonization patterns, increased hypha septation in living root cells, as well as formation of arbuscules, knots, coils and vesicles—putative symbiotic functional organs—may indicate local specialization within the fungal endophytes to promote plant mycovitality and mycoheterotrophy. Bactovitality is mostly characterized by *Streptomyces* intercellular curly filaments.

Figure 12:
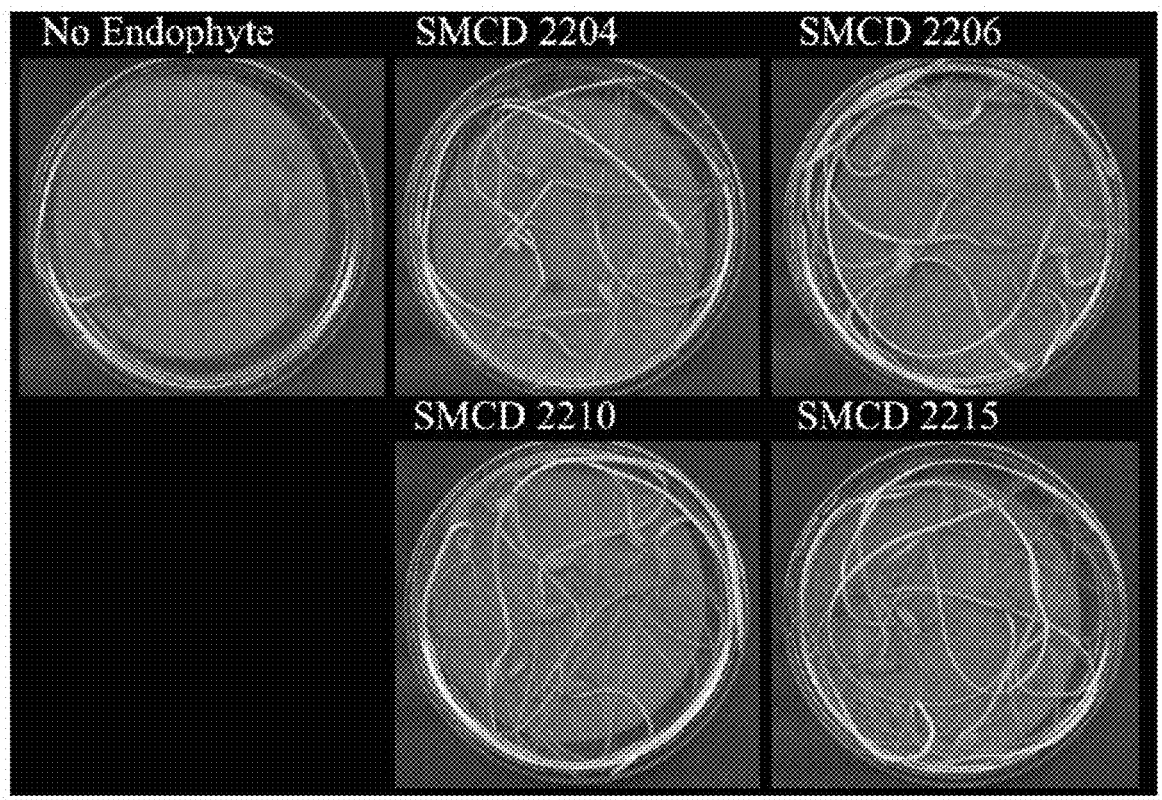
FIG. 12 shows the appearance of symbiotic germinating wheat seedlings after 10 days on moist filter paper at 21° C.
Figure 13:
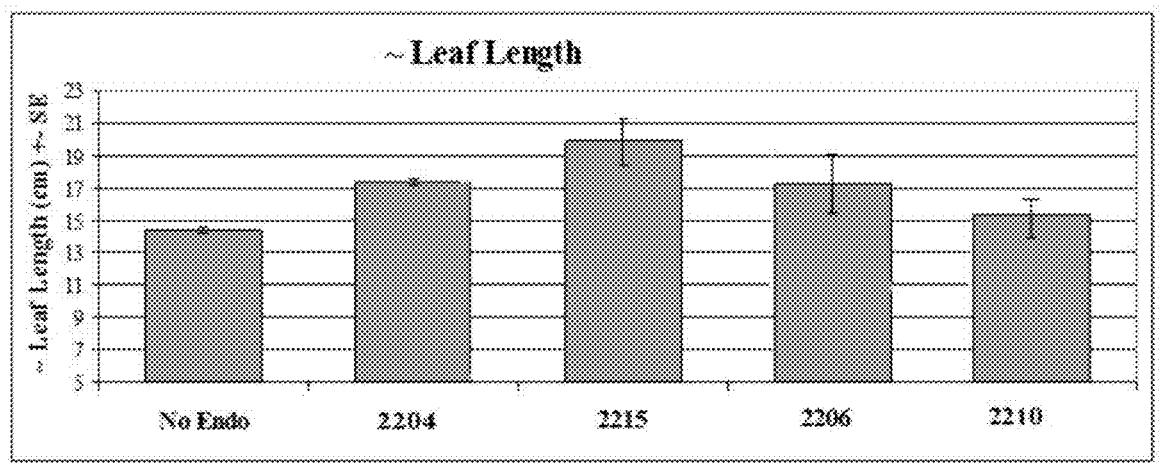
FIG. 13 shows leaf length of germinating wheat seedlings after 10 days at moisture filter paper at 21° C.

Symbiosis at the seed level resulted in increased wheat germinants after 10 days of co-inoculation (FIG. 12 and FIG. 13).

Example 4

Endophytes Improve Wheat Seed Germination Under Heat and Drought Stress

Seed germination is a critical life stage for plant survival and timely seedling establishment especially in stressful environments. It was hypothesized that endophytes would improve wheat seed germination under heat and drought stress. The hydrothermal time (HTT) model of germination is a conceptual model useful for predicting the timing and energy of germination (EG) under a given set of conditions. The HTT and EG are applied to determine if one or more compatible endophytes enhance heat or drought tolerance in wheat. Endophytes tested dramatically increased the percent of germination, improved EG and HTT values, and diminished wheat susceptibility to heat and drought as measured by fresh weight of seedlings. When colonised by the most effective endophyte, the values of the parameters tested in wheat seeds exposed to heat stress resembled those of unstressed seeds.

Materials and Methods

Hydrothermal Time Model of Germination and Energy of Germination

The hydrothermal time (HTT) model [Gummerson 1986] postulates that an individual seed begins to germinate when two conditions are met. First, the sum of daily temperatures, above a minimum cardinal value ($T_{min}$), accumulated over a period of time, must pass a threshold value ($\theta_T$), measured in degree days. Second, the seed must accumulate sufficient water potential ($\theta_H$) per degree-day. Thus, HTT ($\theta_{HT}$) can be expressed as:

$$\theta_{HT}=(\theta_H)(\theta_T). \quad \text{(Equation 1)}$$

According to Köchy and Tielbörger [2007], $$\theta_T=(T_{substrate}-T_{min})t \quad \text{(Equation 2)}$$

with t representing the time elapsed in days, and $$\theta_H=\psi_{substrate}-\psi_{min} \quad \text{(Equation 3)}$$

in a constant environment assuming that $T_{substrate}$ is equal to or less than the optimal temperature for seed germination. In Equation 3, $\psi_{substrate}$ and $\psi_{min}$ represent the water potential of the substrate and the minimum water potential at which germination is possible, in MPa, respectively. Consistent with Bradford [2002], equations 2 and 3 can be substituted into equation 1 to yield:

$$\theta_{HT}=(\psi_{substrate}-\psi_{min})(T_{substrate}-T_{min})t \quad \text{(Equation 4).}$$

However, in the present study, the temperature exceeds the optimal temperature for the germination of wheat [reviewed by McMaster (2009)], necessitating the consideration of a maximum temperature ($T_{max}$) above which germination cannot occur. Thus, equation 2 was modified to:

$$\theta_T=\sqrt{[(T_{substrate}-T_{min})(|T_{substrate}-T_{max}|)]}t \quad \text{(Equation 5)}$$

where $T_{min} \leq T_{substrate} \leq T_{max}$. If equation 5 is substituted for 2 in equation 4, the following results:

$$\theta_{HT}=(\psi_{substrate}-\psi_{min})\sqrt{[(T_{substrate}-T_{min})(|T_{substrate}-T_{max}|)]}t \quad \text{(Equation 6)}$$

where $T_{min} \leq T_{substrate} \leq T_{max}$.

Energy of germination (EG) can be defined in several ways, including the percentage of seeds germinating after a set time period after planting, relative to the number of seeds tested [Ruan et al. 2002; Dong-dong et al. 2009], or 50% of germination attained [Allen 1958]. In order to integrate EG with the HTT model of germination the latter definition was used, meaning that EG is equal to t in Equation 2.

Estimation of Parameters

The estimation of $T_{min}$ and $T_{max}$ for wheat was based on both information available in the literature and the present inventors' own observations. McMaster [2009] summarizes data originating from Friend et al. [1962], Cao and Moss [1989], and Jame et al. [1998] indicating the existence of a curvilinear relationship between wheat development rate and temperature. Since germination and development of wheat does not take place below 0° C. or above 40° C., $T_{min}$ and $T_{max}$ were assigned the values of 0° C. and 40° C., respectively.

The parameter $\psi_{min}$ was estimated in vitro by germinating wheat seeds grown on potato dextrose agar (PDA; Difco) media containing a range of polyethylene glycol (PEG) 8000 concentrations (Amresco Inc.). The water activity ($a_w$) of PDA alone and PDA containing 8%, 12% and 16% PEG was measured using the AquaLab 4TE, Series 4 Quick Start, Decagon Devices. Water activity was converted to water potential ($\psi$) using the relationship adapted from Bloom and Richard [2002]:

$$\psi=[(RT)\ln(a_w)]/V \quad \text{(Equation 7)}$$

where R is the universal gas constant (8.314 J mol$^{-1}$ K$^{-1}$), T is the temperature in ° K, and V is the partial molar volume of water (18 mL/mol). For unit conversions, 1 J/mL=1 MPa=10 bar. Water potential is zero for a free water surface or a saturated medium; all other values are negative.

The water activities of PDA and PDA containing 8%, 12% and 16% PEG were 0.9974, 0.9890, 0.9863, and 0.9825, respectively. These values are equivalent to −0.35, −1.51, −1.88, and −2.41 MPa, respectively and are consistent with those reported in the literature [Leone et al. 1994].

Plant and Fungal Material

Figure 14:
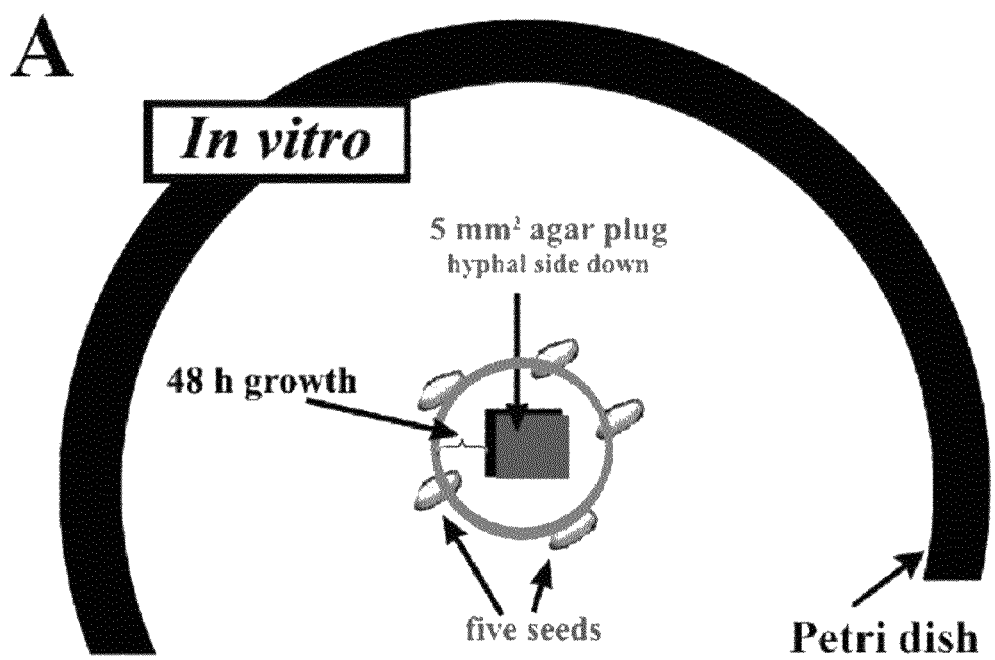
FIG. 14 shows an in vitro inoculation method (A). A 5 mm² agar plug, cut from the margin of the parent colony, was placed hyphal side down in the centre of a 60 mm Petri dish containing potato dextrose agar (PDA) media. Next, five surface-sterilized seeds were placed a distance equivalent to 48 h hyphal growth from the agar plug and germinated in the dark. The impact of three seed surface sterilization methods on seed germination (B). Bars labeled with one or two asterisks (**) are significantly, or highly significantly, different from the same endophyte grown under control conditions (p≤0.05 or p≤0.01, respectively; ANOVA, followed by post-hoc LSD test). Error bars represent standard error of the mean (SE).
Figure 14:
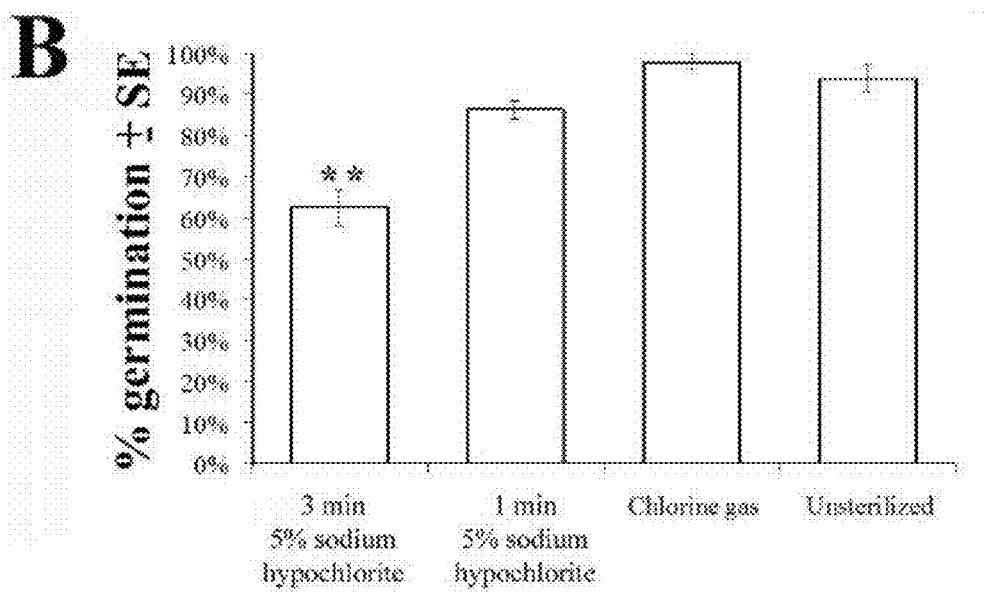

The plant material used was the durum wheat cultivar AC Avonlea, which has low resistance to environmental stressors [SaskSeed guide 2008]. The seeds used in the first round of experiments were produced by Paterson Grain in 2008, under field conditions, and not certified to be free of microbes. Seeds used in the second set of experiments were produced by the Agriculture and Agri-Food Canada (AAFC) Seed Increase Unit Research Farm in 2006 under greenhouse conditions, and were certified to be free of microbes. Wheat seeds were surface-sterilized with 95% ethanol for 10 s, rinsed in sterile distilled water for 10 s, submerged for either 3 min (first round of experiments involving seeds not certified to be free of microbes) or 1 min (second round of experiments using seeds certified to be microbe-free) in 5% sodium hypochlorite (Javex), rinsed three times in sterile distilled water and PDA for germination [Abdellatif et al. 2009]. A third seed sterilization method, involving a 3 hr exposure to chlorine gas (produced by combining 25 mL 6% sodium hypochlorite with 1.0 mL concentrated hydrochloric acid in a beaker) in a closed plastic box placed in a fumehood [Rivero et al. 2011] was also tested. The percent germination of seeds subjected to each sterilization protocol and placed on PDA for three days is shown in FIG. 14B. Only the 3 min submersion in sodium hypochlorite resulted in a significant decrease in germination ($p \leq 0.01$). Seed surface sterilization was intended to eliminate microbes which could compete with the endophytes being investigated. In addition, microbes present on the surface of the seeds could overgrow the plate and emerging seedling, inhibiting plant growth. All seeds used in the study were determined to be free from microorganisms after sterilization, based on the absence of unintended microbial growth on the plate.

Four endophytic Ascomycota mitosporic fungal isolates (classified according to Kiffer and Morelet [2000]): SMCD 2204, SMCD 2206, SMCD 2208, and SMCD 2210, plus the Actinomycetes filamentous gram positive bacterial isolate SMCD 2215; compatible with *Triticum turgidum* L. [Abdellatif et al. 2009] were used in this study. Endophytes were grown on PDA for at least three days at room temperature in darkness prior to experimental use.

Endophytes as Free-Living Organisms

Agar plugs (5 mm$^2$) cut from the margins of the parent colony were placed in the centre of a 90-mm Petri dish containing either PDA alone or amended with 8% PEG (drought). The Petri dish was sealed with parafilm (Pechiney Plastic Packaging) to maintain sterility and placed in a bench-top incubator (Precision Thermo Scientific, model 3522) at either 23° C., or under heat stress, 36° C., in darkness. The diameter of the colony was measured at 24, 48, 72, 96 h, and five and six days. The changes in diameter were used to calculate colony growth rate. The growth of a minimum of three replicates per isolate was measured.

Endophytes Ability to Confer Heat and Drought Tolerance to Wheat

Each isolate was applied individually to wheat seeds prior to germination according to the method described in Abdellatif et al. [2010] and shown in FIG. 14A. Briefly, five surface-sterilized seeds were placed at a distance equivalent to 48-h hyphal growth from a 5 mm$^2$-agar plug, placed hyphal side down in the centre of a 60-mm Petri dish. For slow growing isolates, the agar plug of endophyte colony was placed in the Petri dish one to four days prior to the introduction of the seeds. The seedlings were germinated for one week under abiotic stress and control conditions.

Drought stress was induced using PDA containing 8% PEG. Heat stress was induced in a bench-top incubator in darkness; the temperature was gradually raised by 2° C. every 2 h from 28° C. to 36° C. In the initial round of experiments, percent germination at three days and fresh weight at one week was assessed. Each experiment consisted of six Petri plates and was repeated, independently, three times. In subsequent experiments, percent germination was assessed every 24 hrs for seven days. Each experiment consisted of 10 Petri plates and was repeated either twice (heat and drought stress combined) or three times (heat stress, drought stress and control conditions).

The stable internal colonization of wheat roots by the intended endophytes was confirmed by re-isolation of the endophytic organism from roots which had been surface sterilized to remove an external microbial growth using a procedure modified from Larran et al. [2002]. Root fragments (~0.5 cm) were surface sterilized in 95% ethanol for 10 s, rinsed in sterile distilled water for 10 s, submerged for 20 s in 5% sodium hypochlorite (Javex), rinsed three times in sterile distilled water and placed on PDA in a 60 mm diameter Petri dish. The Petri dish was sealed with parafilm and incubated in the dark at room temperature for four to seven days prior examination.

Statistical Analysis

The colony growth rates of free-living endophytic organisms grown under heat or drought stress were compared to those of the same organism grown under control conditions using analysis of variance (ANOVA) followed by post-hoc Fischer's' least significant difference (LSD) test. Percent germination data was subjected to arcsine transformation prior to statistical analysis [McDonald 2009]. Statistical differences between percent germination after both three and seven days, and fresh weight at seven days were assessed using a single factor ANOVA to compare all treatments. Subsequently, a post-hoc LSD test was used to evaluate the significance of differences between the no endophyte control and seeds treated with each mycobiont. The level of statistical significance associated with differences between the EG and HTT required to reach 50% germination of endophyte-colonized and control seeds were assessed by evaluating the EG for each of the three independent replicates of the experiment. The resulting data were subjected to an ANOVA and post-hoc LSD analysis. P-values less than 0.05 and 0.01 were considered to be significant and highly significant, respectively. Statistical tests were run with SPSS Inc. 2011.

Results

Within each section, the results are organised according to the type of stress: heat, drought, heat and drought, or no stress. Within each stress, the results dealing with plant material are presented according to the germinant and/or seedling traits measured: percent germination at three and seven days, fresh weight at seven days, EG and HTT.

Free Living Endophytes

Figure 15:
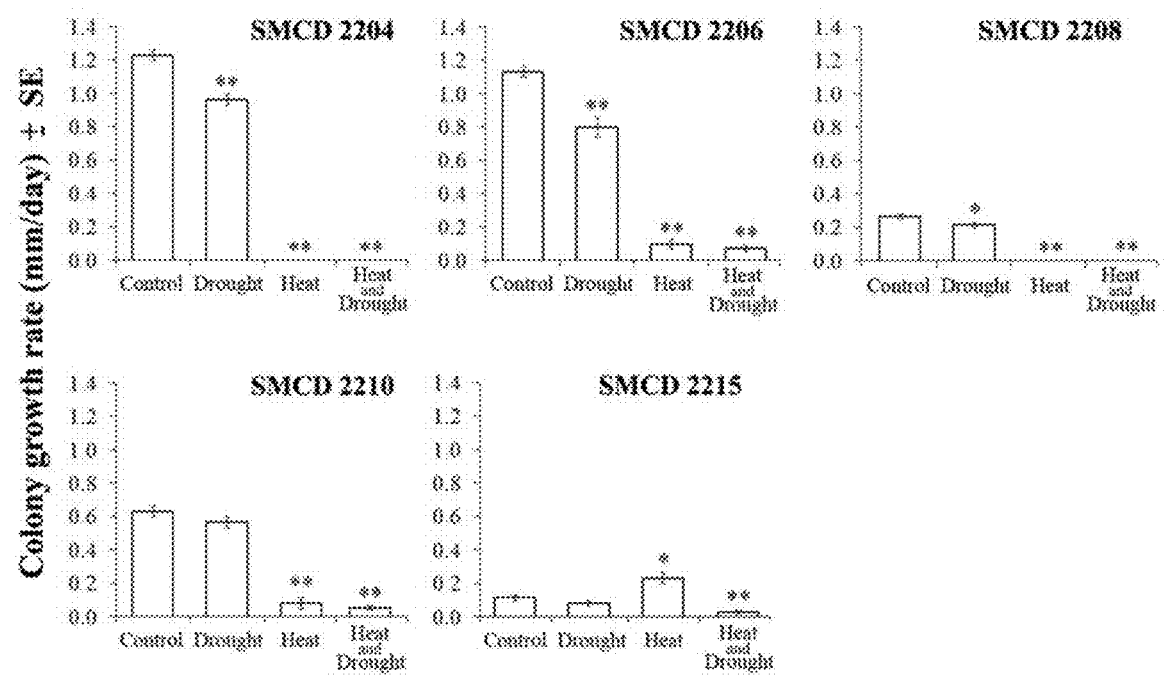
FIG. 15 shows growth rates of free-living endophytes SMCD 2204, 2206, 2208, 2210, and 2215 in vitro on potato dextrose agar (PDA) under heat stress (36° C.), drought (8% polyethylene glycol (PEG) 8000) stress and control conditions for five days and simultaneous heat (36° C.) and drought (8% PEG) for six days. Bars labeled with one or two asterisks (**) are significantly, or highly significantly, different from the same endophyte grown under control conditions (p≤0.05 or p≤0.01, respectively; ANOVA, followed by post-hoc LSD test). Error bars represent standard error of the mean (SE).

The phenotypes of SMCD 2206, 2210 and 2215 were not altered by heat (36° C.), while SMCD 2204 and 2208 did not grow at 36° C. The colony growth rates of SMCD 2206 and 2210 were reduced by 36° C. as compared to non-stressed conditions ($p \leq 0.01$), while the growth rate of SMCD 2215 at 36° C. was increased ($p \leq 0.05$) (FIG. 15). At 36° C. SMCD 2215 grew the most rapidly, followed in decreasing order by 2206 and 2210 (FIG. 15).

The morphology of SMCD 2204, 2206, 2208 and 2215 was not appreciably altered by drought (8% PEG). However, when SMCD 2210 was exposed to drought, this organism lost its "woolly" appearance and instead acquired a "shiny" or "slimy" appearance. The colony growth rates of SMCD 2204, 2206, and 2208 were reduced by drought ($p \leq 0.01$, $p \leq 0.01$, and $p \leq 0.05$ respectively), while the rate of colony growth of all other endophytes remained unchanged (FIG. 15). When drought stress was applied, SMCD 2204 grew at the highest rate followed in decreasing order by 2206, 2210, 2208 and 2215 (FIG. 15).

When challenged by 36° C. heat and drought (8% PEG) simultaneously, SMCD 2204, and 2208 failed to grow, while SMCD 2206, 2210 and 2215 grew at a significantly slower rate than under control conditions ($p \leq 0.01$) (FIG. 15). In control conditions, SMCD 2204 grew the fastest, followed in decreasing order by SMCD 2206, 2210, 2208 and 2215 (FIG. 15).

Response of Endophyte-Colonized Wheat to Heat

Figure 16:
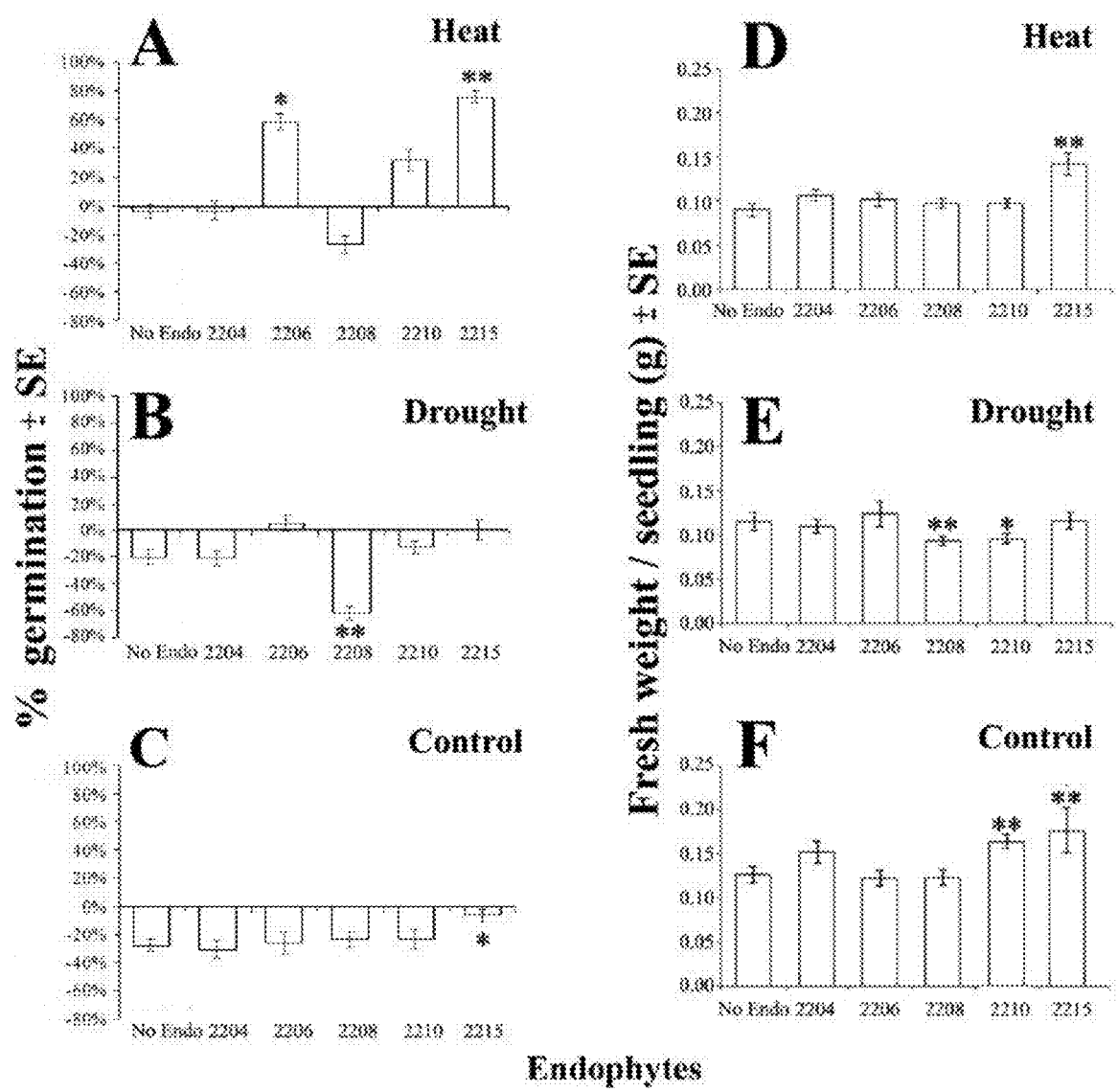
FIG. 16 shows percent germination and fresh weight of seedlings from initial experiments in which seeds were surface sterilized in 5% sodium hypochlorite for 3 min. Percent germination of wheat seeds in vitro after three days on potato dextrose agar (PDA) under heat stress (36° C.), drought stress (8% polyethylene glycol (PEG) 8000) and control conditions (A, B and C) with the y axis normalized to percent germination obtained under the same conditions by seeds surface sterilized in 5% sodium hypochlorite for 1 min. Fresh weight of seedlings in vitro at seven days on PDA under heat stress, drought stress and control conditions (D, E and F). Bars labeled with one (*) or two asterisks (**) are significantly, or highly significantly, different from the no endophyte control (p≤0.05 or p≤0.01, respectively; ANOVA, followed by post-hoc LSD test). Error bars represent the standard error of the mean (SE).
Figure 17:
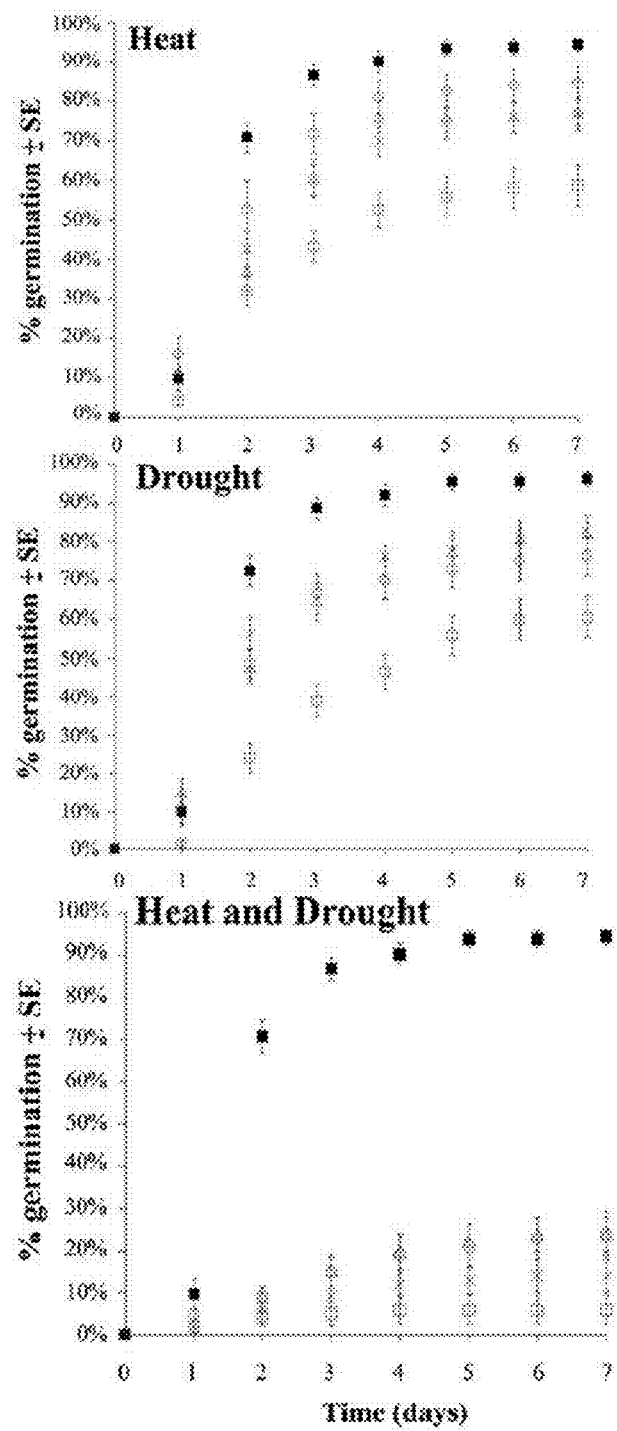
FIG. 17 shows percent germination over time of wheat seeds co-cultured with the endophytes most effective at conferring abiotic stress tolerance (SMCD 2206, 2210 and 2215) compared to uncolonized, unstressed seeds (positive control) and uncolonized, stressed seeds (negative control). Energy of germination (EG) is related to the time, in days (x axis) at which 50% germination (y axis) is reached. The symbols "■", "x", "○", "Δ", and "□" represent the positive control, SMCD 2206 treated seeds, SMCD 2210 treated seeds, SMCD 2215 treated seeds and the negative control, respectively. Heat and drought treatments correspond to 36° C. and 8% polyethylene glycol (PEG) 8000, respectively. Error bars represent the standard error of the mean (SE). Note: The seeds used in EG determination were from the second round of experiments, and hence sterilized in 5% sodium hypochlorite for one minute, rather than three.

At 36° C., colonization by SMCD 2206 and 2215 increased germination after three days (p≤0.05 and p≤0.01, respectively; FIG. 16A), whereas SMCD 2204, 2208 and 2210 did not alter this parameter (p>0.1; FIG. 16A). After seven days, 63% and 56% of seeds germinated in co-culture with SMCD 2204 and 2208, respectively. These values were not statistically different (p>0.1) from the 59% germination achieved by the uncolonized control. In contrast, the endosymbionts SMCD 2206, 2210 and 2215 promoted germination after seven days (p≤0.01; FIG. 17).

When subjected to 36° C., the fresh weight of wheat seedlings was stable in co-culture with SMCD 2204, 2206, 2208, and 2210, while SMCD 2215 significantly increased this parameter (p≤0.01 respectively; FIG. 16D).

The EG for wheat seeds co-cultured at 36° C. with fungal endophyte SMCD 2210 (p≤0.05; Table 3, FIG. 17) improved compared to endophyte-free seeds. However, SMCD 2204, 2206, 2208 and 2215 did not alter EG (p>0.1; Table 3) relative to the control. SMCD 2210 augmented the EG to the greatest extent, followed by SMCD 2206 and 2215 (Table 3). SMCD 2210 reduced the time required for 50% of seeds to germinate to a mere two days.

Figure 18:
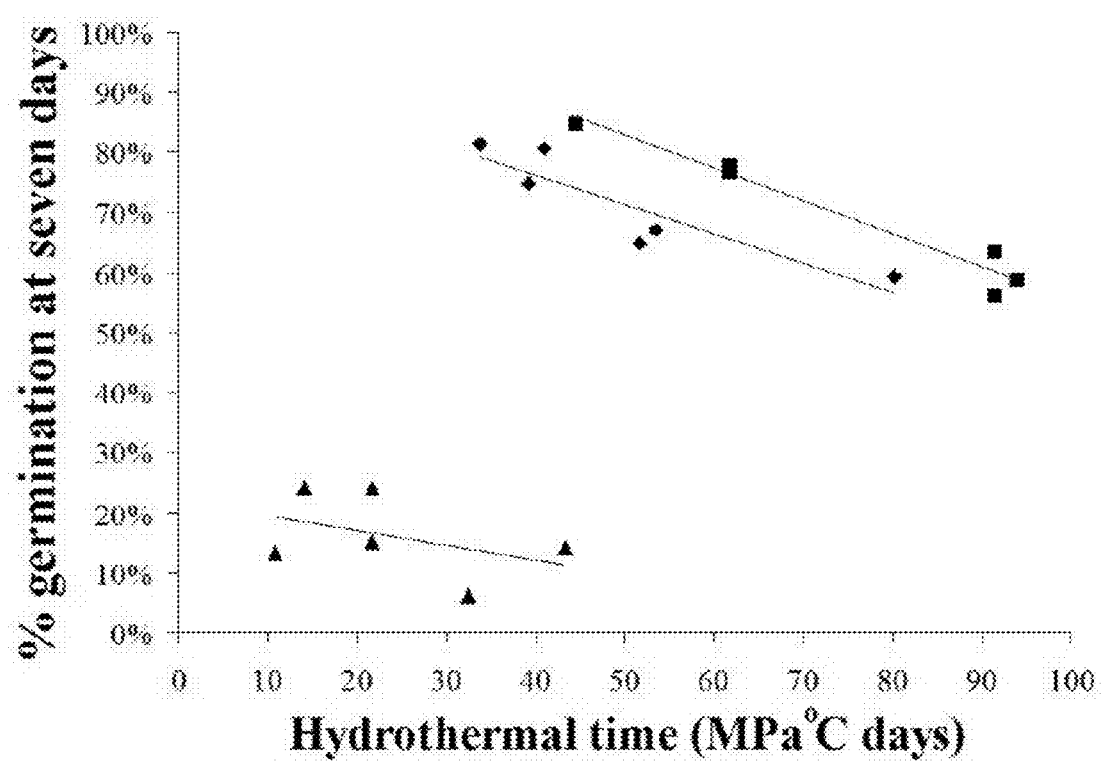
FIG. 18 shows the relationship between hydrothermal time (HTT) required to achieve 50% germination for heat and drought alone and 5% germination for heat and drought combined (x axis) and percent germination attained after seven days (y axis). Germination after seven days and HTT were based on the results of the second round of experiments. The symbols "■", "□" and "▲" represent seeds exposed to heat (36° C.), drought (8% polyethylene glycol (PEG) 8000) or both heat and drought stress, respectively. The R-squared values associated with the trendlines are 0.96, 0.80 and 0.18 for seeds exposed to heat, drought or both heat and drought stress, respectively. Note: The seeds used to determine percent germination at seven days and HTT were from the second round of experiments, and hence treated with 5% sodium hypochlorite for one minute, rather than three.

When exposed to heat stress, the HTT required for germination was reduced for wheat seeds colonized by SMCD 2210 (p≤0.05; Table 3), but not any of the other endophytes tested (p>0.1; Table 3). Endophyte-free wheat seeds needed 50 MPa ° C. days more than seeds colonized by SMCD 2210 (the most effective endophyte tested) to achieve 50% germination (Table 3). There was a clear, negative, linear correlation between the HTT necessary for 50% germination and the percent germination after seven days under heat stress (FIG. 18).

Response of Endophyte-Colonized Wheat to Drought

When subjected to drought stress for three days, a diminished percentage of wheat seeds germinated in co-culture with SMCD 2208, compared to endophyte-free seeds (p≤0.01; FIG. 16B), while SMCD 2204, 2206, 2210, and 2215 did not alter this trait (p>0.1; FIG. 16B). After seven days, treatment with SMCD 2206, 2210 and 2215 led to an increase in seed germination (p≤0.01, p≤0.05, and p≤0.01, respectively; FIG. 17). In contrast, 65 and 67% of seeds co-cultured with SMCD 2204 and 2208 had germinated after seven days. Neither of these values differed statistically from the 59% of uncolonized seeds that germinated under the same conditions (p>0.1). Under drought conditions, SMCD 2208 and 2210 decreased fresh weight after seven days (p≤0.05 and p≤0.01. respectively; FIG. 16E). None of the other mycobionts altered this parameter (p>0.1; FIG. 16E).

The EG decreased for wheat seeds co-cultured in drought conditions with all endophytes tested, as compared to endophyte-free seeds (0.05<p≤0.1 for SMCD 2204 and 2208 and p≤0.05 for 2206, 2210 and 2215; Table 3). SMCD 2206 improved the EG to the greatest extent, decreasing the time elapsed before 50% germination was achieved after 2.6 days (Table 3; FIG. 17).

The HTT required for germination was reduced for wheat seeds treated with all endophytes tested under drought stress (Table 3). While uncolonized seeds needed 80 MPa ° C. days to achieve 50% germination, seeds colonized by endophyte SMCD 2206 (the most effective endophyte tested) required only 34 MPa ° C. days, representing a drop of 46 MPa ° C. days (Table 3). There was a visible, negative, linear correlation between the HTT required for 50% germination and the percent germination at seven days under drought stress (FIG. 18). However, the $R^2$ value associated with this linear relationship was smaller than for the correlation found under heat stress. The ranges of HTTs needed to achieve 50% germination differ between heat and drought stress, with values between 34 and 44 MPa ° C. days and 80 and 94 MPa ° C. days being unique to seeds exposed to drought and heat stress, respectively (FIG. 18; Table 3). The ranges of percent germination after seven days are similar between seeds exposed to drought and those subjected to heat, though the germination levels of heat-stressed seeds cover a slightly larger range (FIG. 18).

Response of Endophyte-Colonized Wheat to Drought and Heat in Combination

Very few wheat seeds germinated when exposed to drought (8% PEG) and heat stress (36° C.) simultaneously (FIG. 17). Colonization by endophytes SMCD 2210 and 2215 increased the percent germination after seven days (p≤0.01; FIG. 17). On the other hand, SMCD 2204, 2206 and 2208 failed to improve this trait (p>0.1). Seeds co-cultured with SMCD 2215 (the most beneficial microorganism tested for this parameter) reached 24% germination, four times the level attained by their endophyte-free counterparts (FIG. 17).

Because neither uncolonized seeds nor those colonized by any of the endophytes reached 50% germination within seven days, EG could not be determined and HTT was calculated for 5%, rather than 50%, germination. The time required to reach 5% germination ranged from 24 h to four days. None of the endophytes tested decreased the time required to attain 5% germination or HTT values (p>0.1). Overall, the HTT needed to reach 5% germination varied from 11 to 43 MPa ° C. days ($HTT_{mean}$=23.9) (FIG. 18; Table 3).

The range of HTT values for seeds subjected to both heat and drought stress were unique, as compared to the HTT values when either heat or drought was applied alone. There was a negative, linear relationship between HTT required and the percent germination under combined heat and drought stress. However, the $R^2$ value associated with this linear relationship was smaller than for the correlation found when either heat or drought stress was applied individually (FIG. 18).

Response of Endophyte-Colonized Wheat to Control Conditions

Under non-stressed conditions, SMCD 2215 significantly increased seed germination compared to uncolonized seeds after three days (p≤0.01) (FIG. 16C). SMCD 2206, 2208 and 2210 positively impacted, whereas SMCD 2204 did not alter percent of germination. In unstressed conditions, SMCD 2204, 2210 and 2215 increased the fresh weight of wheat seedlings after seven days (p≤0.05 and p≤0.01, respectively). Furthermore, SMCD 2206 and 2208 showed no impact on the fresh weight as compared to uncolonized seedlings (FIG. 16F).

In control conditions, EG and HTT parameters were slightly improved by SMCD 2206 and 2215 endosymbionts (Table 3). Relatively little alteration in EG and HTT parameters was measured associated with non-stressed wheat seeds in co-culture with different isolates.

Example 5

Endophytes Enhance Yield of Wheat and Barley Genotypes Under Severe Drought Stress

Figure 19:
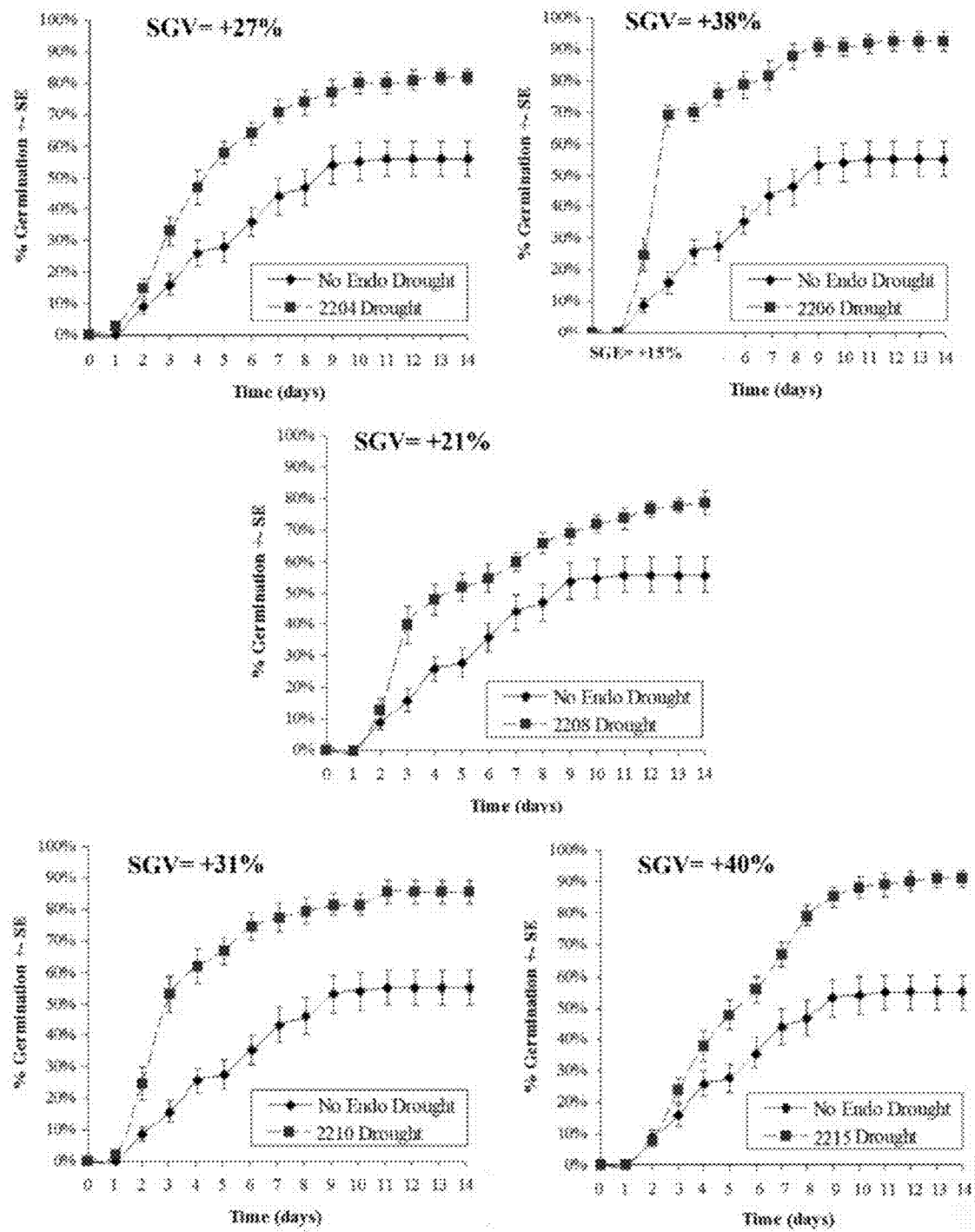
FIG. 19 shows seeds treated or inoculated with SMCD strains demonstrate improvement in all tested seed germination parameters including seed germination vigour (SGV) efficacy.
Figure 20:
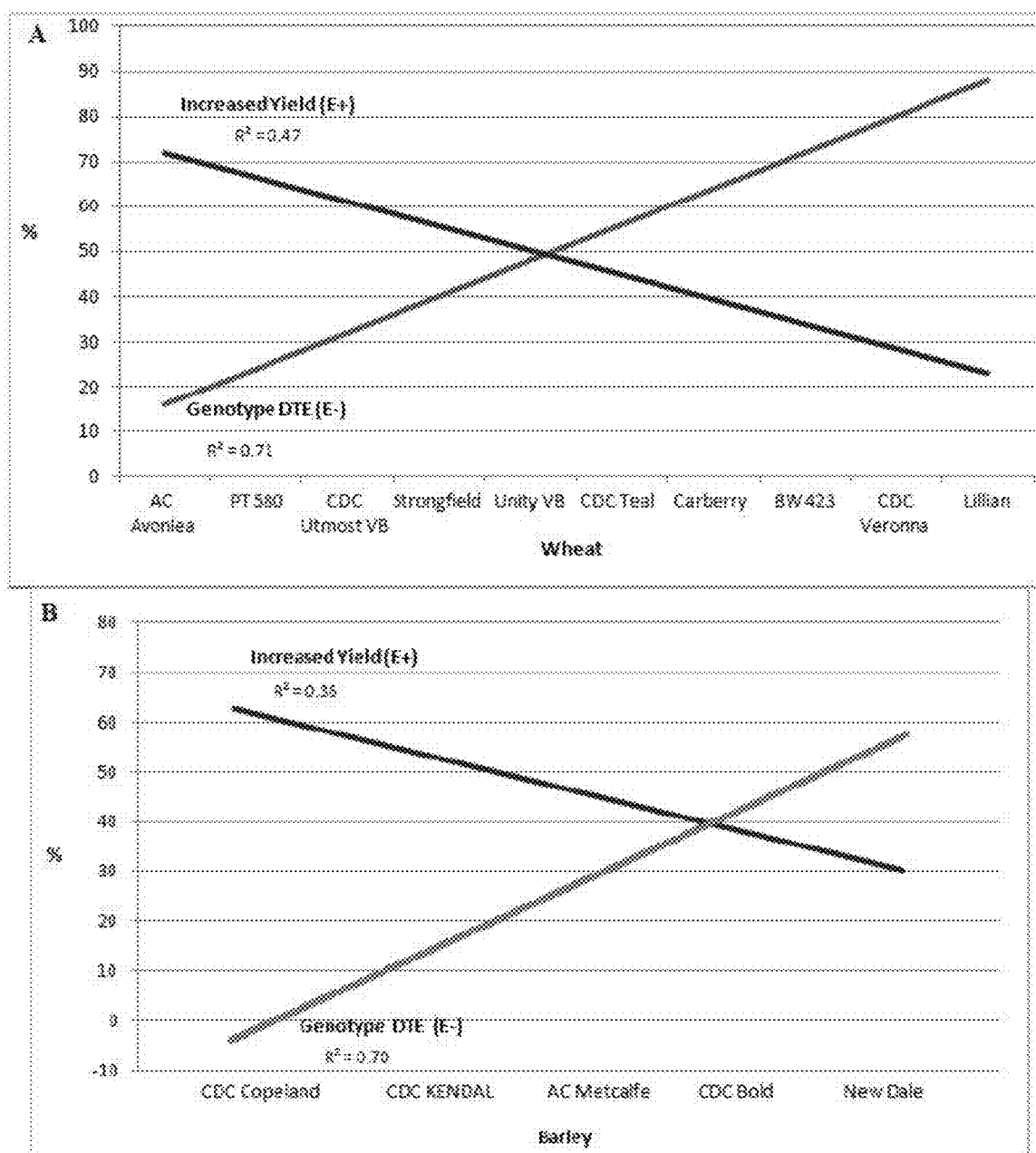
FIG. 20 shows the relationship between drought tolerance efficiency (DTE) values in wheat (A) and barley (B) cultivars without (E−) and with (E+) endophytes, based on the average effect of symbiosis using all tested SMCD isolates, on yield exposed to drought stress in greenhouse.
Figure 21A:
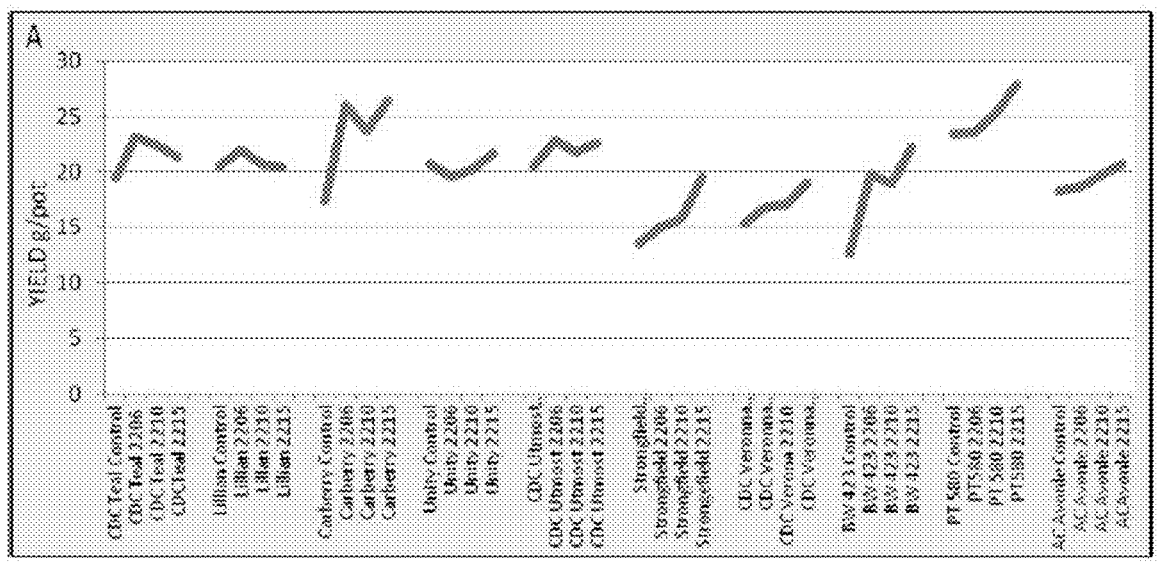
FIG. 21 shows (A) endophytic (E+) inoculants (SMCD 2206, SMCD 2210, and SMCD 2215) improve kernel yield in wheat genotypes compared to control (E−) treatment (yield g/3 pots). (B) Endophytic inoculants (SMCD 2206, SMCD 2210, and SMCD 2215) improve kernel yield in two row barley ($B_a$) and six row barley ($B_b$) genotypes (kernel yield: 3plants/pot).
Figure 21B:
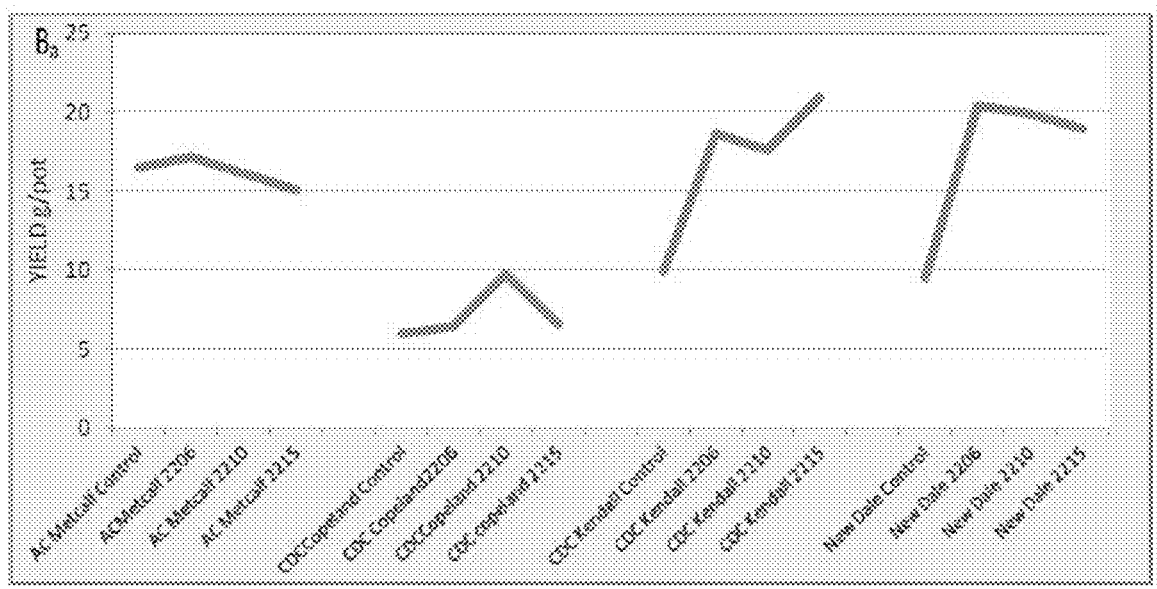
Figure 21B:
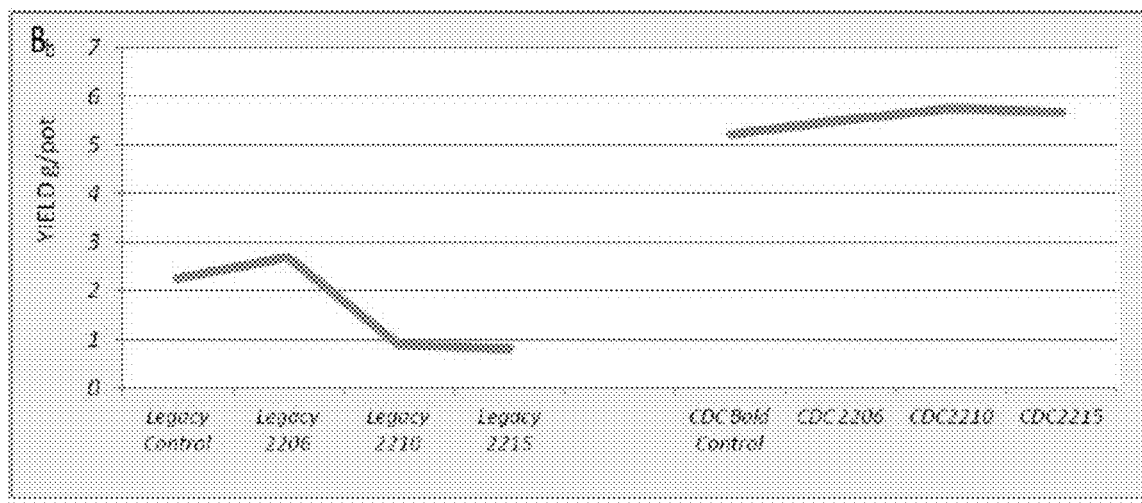

Summary:

Due to climate change and population growth, the development of techniques increasing agriculture crop tolerance in stressful environments is critical. Inoculation with three symbiotic endophytes, indigenous to the Canadian prairies, increases wheat and barley resistance to heat or drought stress, as well as grain yield and seed weight. The use of such fungal and bacterial endophytes in the field has the potential to increase the seed germination vigour (SGV=difference between total percentage of E-germinating seeds and E+ germinating seeds) (FIG. 19, FIGS. 20A and B), and to enhance yield in stress-prone conditions (Table 4; FIG. 21 A, Ba, and Bb). Evidence supports that SMCD strains increase seed-vitality and plant vigour (FIG. 22A-D). Overall results demonstrate that the prenatal care of seed using endophytic microbes, particularly SMCD strains, ensures superior crop yield of wheat and barley genotypes through physiological improvements.

Materials and Methods

Seeds of the wheat and barley cultivars were produced at University of Saskatchewan experimental plots and Crop Science Field Laboratory (Saskatoon). Visually healthy seeds were surface sterilized in 95% ethanol for 10 s, rinsed in sterile distilled water for 10 s, submerged for 1 min in 5% sodium hypochlorite (Javex) and then rinsed three times in sterile distilled water.

The endophytic isolates used in this study were originally isolated from the roots of durum wheat *Triticum turgidum* L. grown at field sites in Saskatchewan, Canada [Vujanovic 2007b]: SMCD 2204, 2206, 2208, 2210, 2215. All endophytic isolates are culturable on potato dextrose agar (PDA; Difco) in the absence of a host plant. Isolates were grown on PDA for three days at room temperature (23° C.) in darkness prior to experimental use.

The experiment inoculations were done in pots. Each of the endophytic isolates was applied to cereal (wheat and barley) seeds prior to germination according to the method described in Abdellatif et al. [2010]. Briefly, five surface-sterilized seeds were positioned at a distance equivalent to 48 h hyphal growth from a 5 mm$^2$ agar plug, placed hyphal side down in the centre of a 2 L plastic pot filled with 300 grams (dry weight) of autoclaved, field capacity Sunshine mix 4 potting soil. The seeds and agar plug were then covered with a 3.5-4.0 cm layer of Sunshine mix 4. Five seeds were planted per pot and there were twelve pots per treatment. Pots containing plants were placed in a greenhouse for drought stress and control treatments. The pots were arranged in a randomized block design.

Drought stress was induced from May to September when night-day maximum temperatures in the greenhouse ranged from 18 to 26° C. On sunny days, natural sunlight provided irradiation, while on cloudy or winter days with a shorter photoperiod, 1000 watt high pressure sodium light bulbs, suspended from the ceiling roughly 2 m above the plants, supplemented sunlight. In the first experiment, drought stressed and control (well watered) plants were grown at 25% soil water content by weight and 100% water retention capacity, respectively. During the experiment control plants were watered to 100% water retention capacity three times per week, while drought stressed plants were water to 100% water retention capacity weekly. This drought regime was adopted in order to mimic the natural cycle of drought that can occur during the growing season in North American prairies [Chipanshi et al. 2006].

Mature spikes were collected and dry kernels weighed on a Mettler Toledo PG802-S balance in laboratory.

Results and Discussion

Increased Wheat Seed Germination Vigour (SGV)

Under in vitro control conditions, SMCD (2204, 2206, 2208, 2210, 2215) treated wheat seeds germinated consistently faster, more uniformly, and with much higher SGE (seed germination efficacy). The SGV of seeds inoculated with SMCD (E+) was 15% to 40% greater compared to untreated (E−) seeds (FIG. 19), demonstrating SMCD's efficacy in controlling seed dormacy and enhancing seed vigor. Positive effects of SMCD strains on yield of wheat and barley genotypes under severe drought were also demonstrated.

Barley genotypes generally show higher drought susceptibility (low DTE (Drought Tolerance Efficacy) values) and lower yield performance than wheat (Table 4), possibly due to the extreme drought conditions in the greenhouse more fitting to wheat. In particular, CDC Kendall-two row barley, without endophyte (E−), shows high susceptibility to drought stress compared to other barley genotypes. However, the endophyte treatments (E+) demonstrate a remarkable positive effect on yield of all genotypes (Table 4). Conferred resistance ranges from low drought resistant CDC Kendall to highly resistant New Dale genotypes, whereas conferred resistance to wheat was consistently high.

During the maturity stage of wheat and barley, SMCD endophytes dramatically increase the genotypes drought tolerance parameters such as DTE efficacy and yield. SMCD application on Avonlea, the most drought susceptible wheat cultivar detected (DTE=16.1), resulted in a high increase in yield (77%) under drought conditions compared to control or standard watering. Carberry profited the most from endophytes under control or normal conditions, whereas CDC Utmost VB and BW 423 performed equally well under both dry and control conditions.

In conclusion, combining drought resistant genotypes with compatible endophytic SMCD 2206, SMCD 2210, and SMCD 2215 microbial symbionts maximizes plant drought resistance, an important aspect in ensuring food security. Without wishing to be bound by theory, this suggests that the most drought susceptible (low DTE values) wheat (FIG. 19A) and barley (FIG. 19B) cultivars will gain the most from the symbiotic association when exposed to the drought stress.

The only exception seemed to be the six row barley genotype Legacy showing an extremely low DTE=1.1. Although it responded positively to the endophyte presence with increased yield of 26.9% under control conditions, it ameliorated yield only for 5% in symbiosis under stress. Thus, this cultivar was excluded from the barley model presented in FIG. 19B.

Effect of Individual SMCD Strains on Wheat and Barley Productivity

Individual SMCD strains positively affect the average kernel yield of each genotype, although the actual magnitude varies by genotype-strain combination. FIG. 21 presents results obtained under drought conditions in the greenhouse (FIG. 21: A—Wheat; B$_a$—Barley (two row), and B$_b$—Barley (six row)).

Early seed contact with compatible SMCD isolates is a prerequisite for protecting crop against drought, resulting in a higher yield or production of kernels. SMCD 2206 generally confers the highest degree of improvement for most genotypes. However, strain-cultivar specificity ensures highest improvements on an individual basis, e.g. Wheat-PT580 and Barley-CDC Copeland prefer SMCD 2210; whereas Wheat-BW423 and PT580, as well as CDC Kendall show higher performance and drought resistance when inoculated with SMCD 2215.

Figure 22:
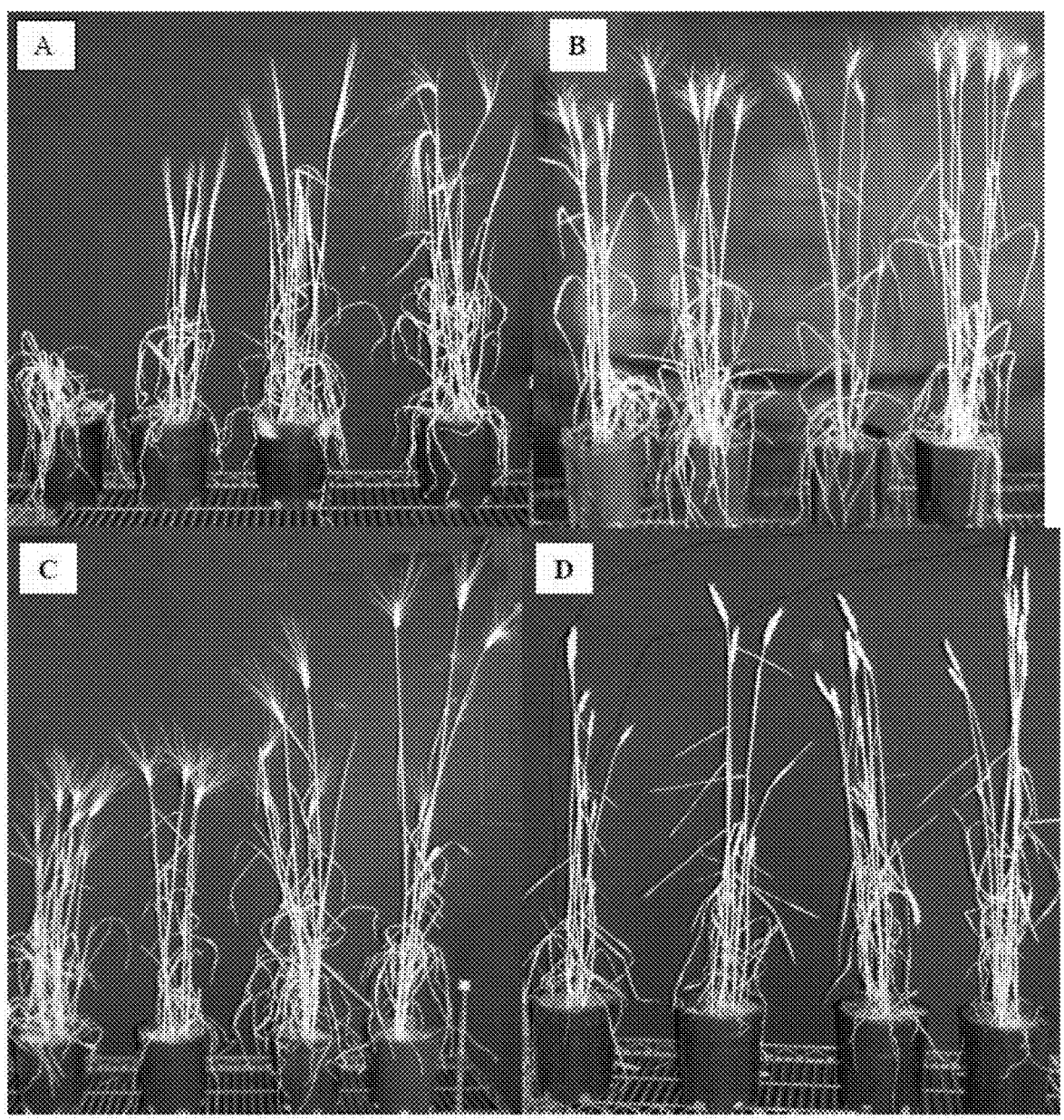
FIG. 22 shows (A) Barley-six row AC Metcalfe, from left to the right: Drought (E−), Drought and SMCD 2206 (E+), Control (E−), Control and SMCD 2206 (E+); (B) Wheat-Unity cultivar, from left to the right: Drought (E−), Drought and SMCD 2215 (E+), Control (E−), Control and SMCD 2215 (E+); (C) Wheat-Verona cultivar, from left to the right: Drought (E−), Drought and SMCD 2215 (E+), Control (E−), Control and SMCD 2215 (E+); and (D) Durum wheat-TEAL, from left to the right: Drought (E−), Drought and SMCD 2210 (E+), Control (E−), Control and SMCD 2210 (E+).

Results highlight the importance of mycovitalism in stress-challenged wheat and barley seeds, assisting breeders in the making of highly productive cultivars capable of withstanding drought conditions significantly better than any cultivar alone (FIG. 22: A-D). Upon demonstrated performance of SMCD strains in fields, producers will have green symbiotic products to secure crop yield, and the agro-business will benefit from a guaranteed level of positive crop outcomes independent of fluctuations in environmental conditions.

Example 6

Phytotron Heat Stress Experiment on Pulses

This experiment was conducted under phytotron conditions. All seed varieties were inoculated with endophytes (SMCD 2204F, SMCD 2206, SMCD 2210, and SMCD 2215) and without endophytes in pots containing the soil mix. Details about the approaches used for endophyte inoculation on plant are described above under Example 5. Pots containing plants for heat stress were placed in a phytotron Conviron PGR15 growth chamber (Controlled Environments Ltd.) using a randomized block design. A temperature of about 33° C. was selected for heat stress. Plants were exposed to this temperature for 8 h, after which time the plants were exposed to a temperature of 21° C. for 16 h up to 10 days. After heat shock, temperatures were changed to 16° C. for 8 h and 21° C. for 16 h.

Results

Figure 23:
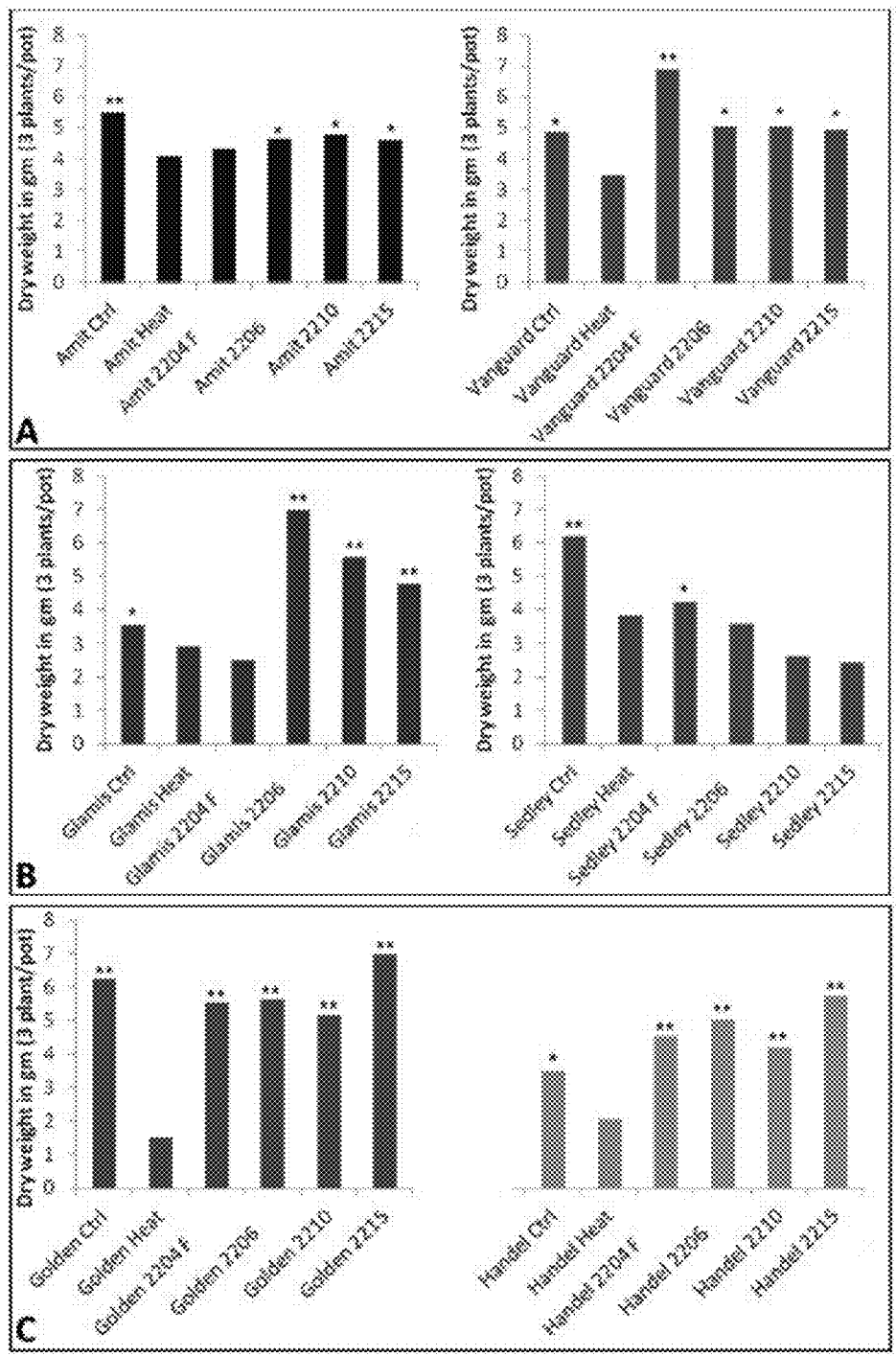
FIG. 23 shows stem dry weight of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).
Figure 24:
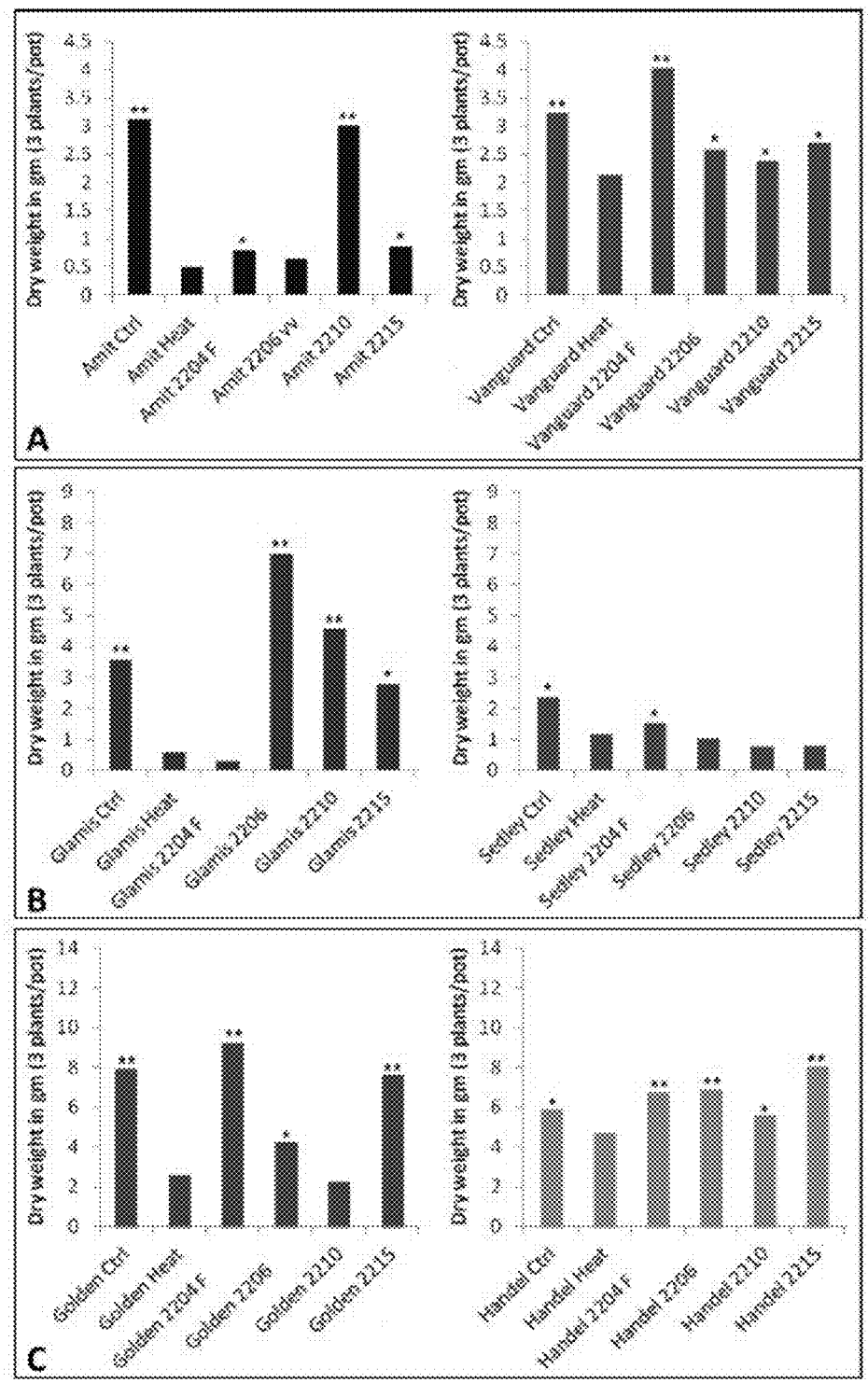
FIG. 24 shows pods dry weight of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).
Figure 25:
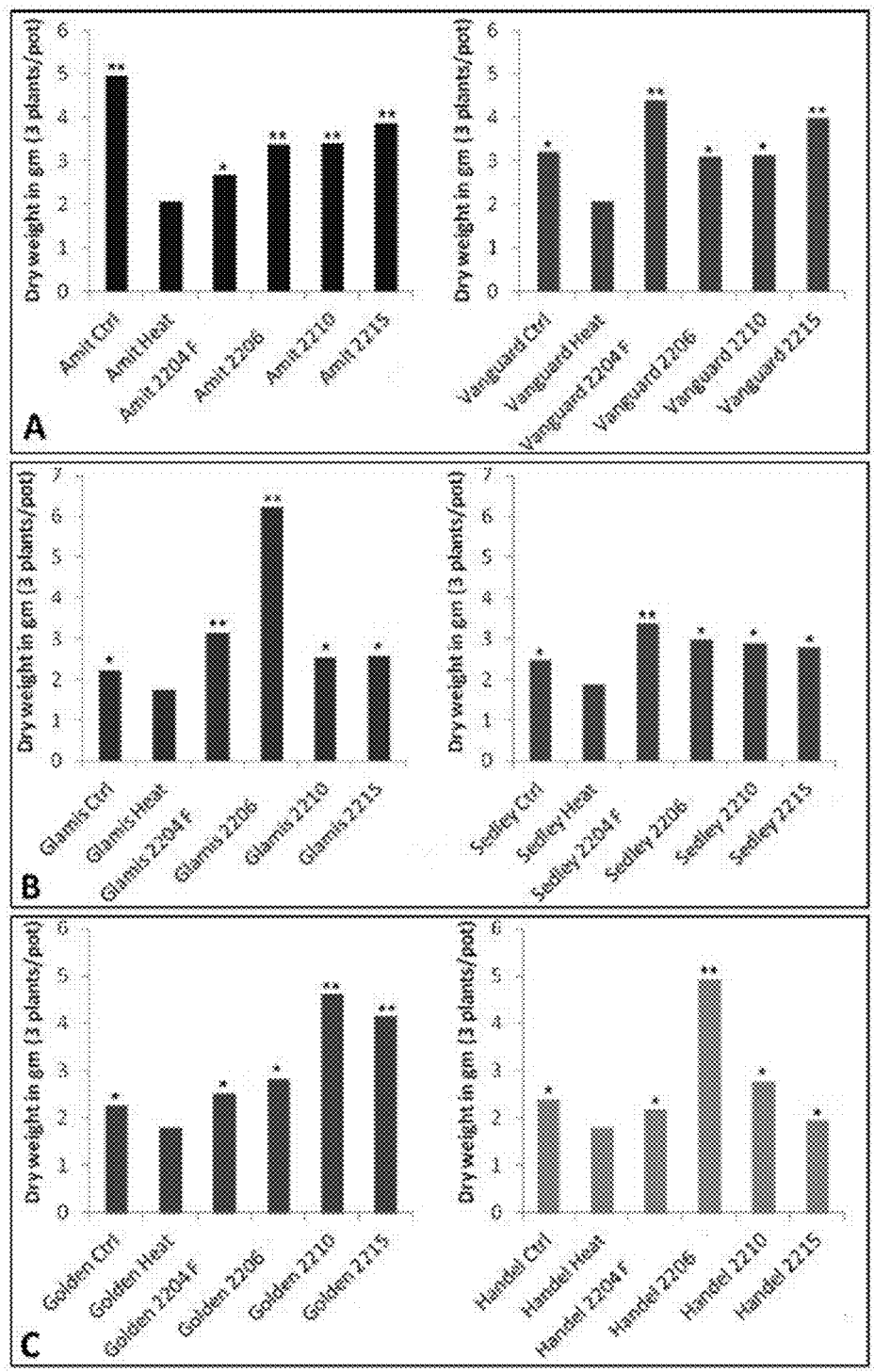
FIG. 25 shows roots dry weight of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).

In summary, the results show that the efficacy of each tested endophyte in conferring heat stress tolerance is related to the particular plant genotype or host variety (A—chickpea, B—lentil, and C—pea), and that the improvement in the biomass is associated to a particular plant organ as each organ: pod (FIG. 23), stem (FIG. 24) and root (FIG. 25), is differentially impacted by heat stress.

SMCD 2215 mostly enhanced the biomass of the stem and pod in pea, and the biomass of root in chickpea. SMCD 2206 increased the biomass of the stem and pod in lentil, and the biomass of root in chickpea, pea, and lentil. SMCD 2210 mostly improved the biomass of the stem and pod in chickpea, and the biomass of root in pea. SMCD 2204F improved the biomass of pods in most of the tested crops (chickpea, pea, and lentil). The best performer endophyte-crop genotype combination (E+) showed an improvement of about 300% in the biomass of pod, stem, and root compared to no endophyte (E−) heat stressed control.

Stem:

The following endophytes showed the best response to heat stress: Chickpea: Amit: SMCD 2210. Vanguard: SMCD 2204F; Pea: Golden: SMCD 2215. Handel: SMCD 2215; and Lentil: Glamis: SMCD 2206. Sedley: SMCD 2206.

Pods:

The following endophytes showed the best response to heat stress: Chickpea: Amit: SMCD 2210. Vanguard: SMCD 2204F; Pea: Golden: SMCD 2204F. Handel: SMCD 2215; Lentil: Glamis: SMCD 2206. Sedley: SMCD 2204F.

Root:

The following endophytes showed the best response to heat stress: Chickpea: Amit: SMCD 2215. Vanguard: SMCD 2206; SMCD 2215; Pea: Golden: SMCD 2210; SMCD2215. Handel: SMCD 2206; Lentil: Glamis: SMCD 2206; Sedley: SMCD 2204F.

Example 7

Greenhouse Drought Stress Experiment on Pulses

Six seed varieties [Amit, Vanguard (chickpeas), Golden, Handel (peas) and Glamis, Sedley (lentils)] and endophytes SMCD 2204, SMCD 2204F, SMCD 2206, SMCD 2210, and SMCD 2215 were used in this study. These experiments were conducted in the greenhouse. After sowing the seed and inoculating endophytes, pots were allowed to stay without water for 14 days to mimic severe drought as proposed by Chariton et. al. [2008] and as per the methodology and conditions outlined by Gan et al. [2004].

Results

Figure 26:
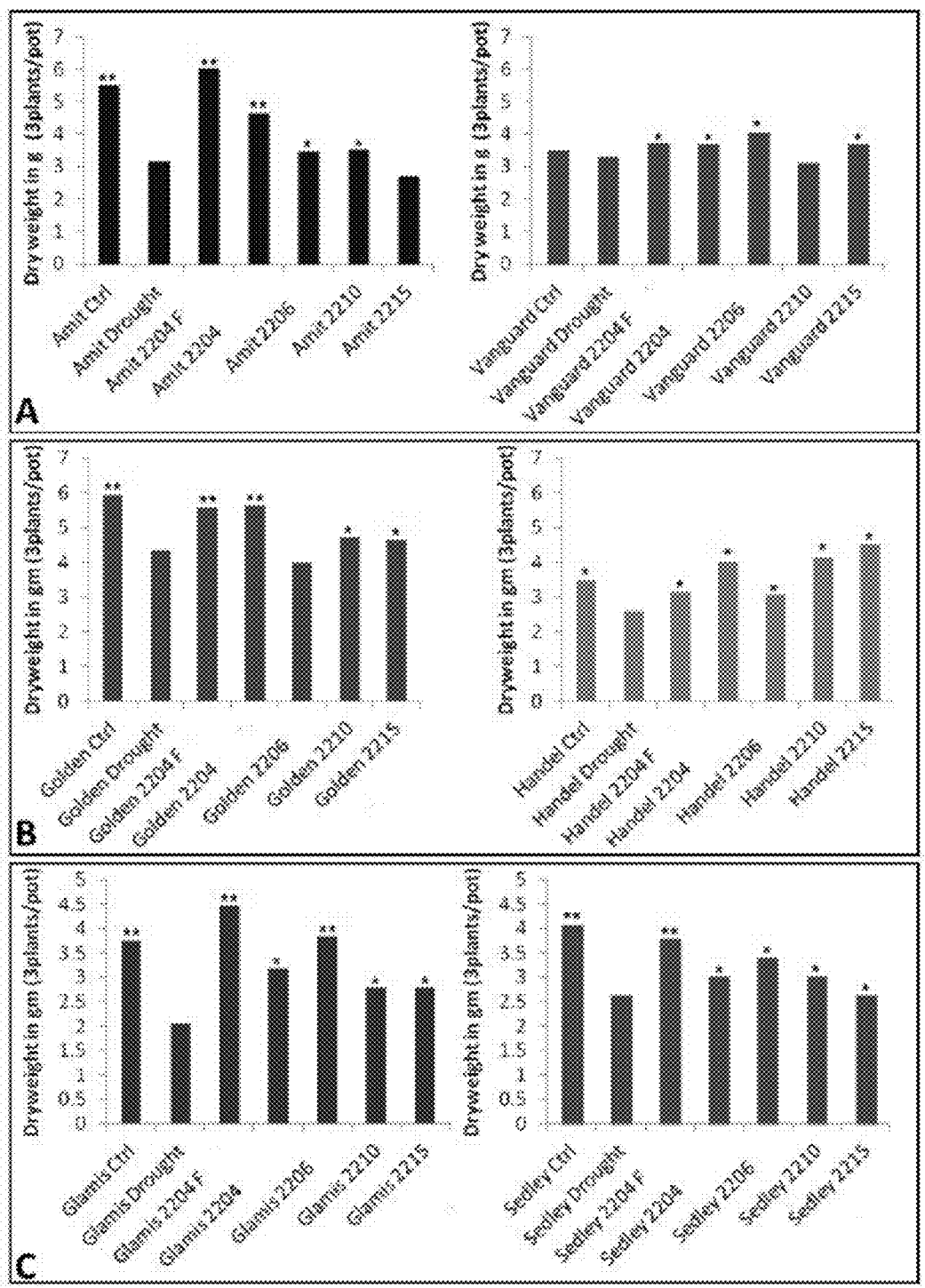
FIG. 26 shows stem dry weight of (A) chickpeas, (B) peas, and (C) lentils under drought stress in a greenhouse. Bars labeled with one (*) or two asterisks (**) are significantly, or highly significantly, different from the no endophyte (E−) stressed control (p≤0.05 or p≤0.01, respectively; ANOVA, followed by post-hoc LSD test).
Figure 27:
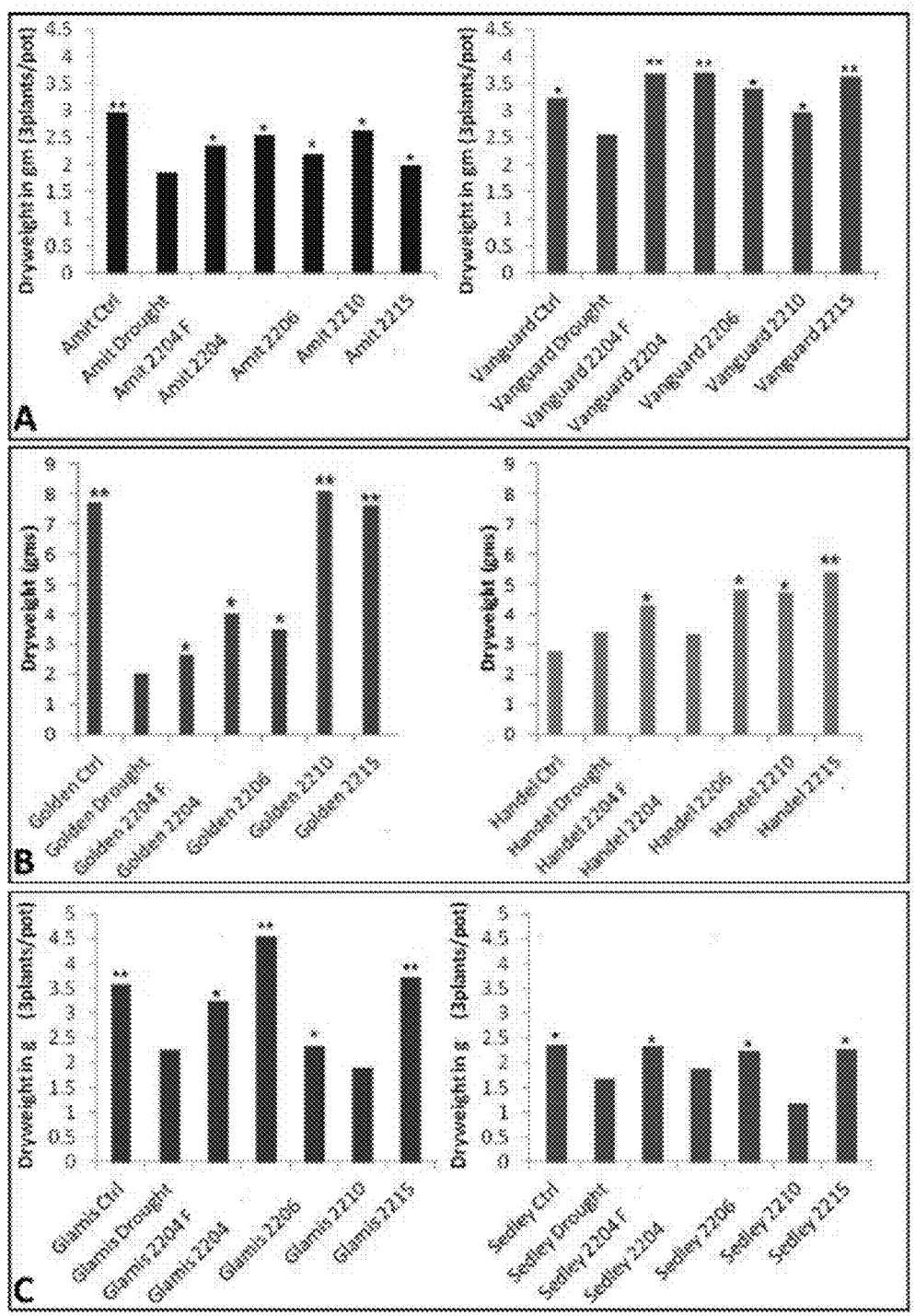
FIG. 27 shows dry weights of (A) chickpeas, (B) peas, and (C) lentils pods in association with an endophyte (E+) under drought stress in the greenhouse. Bars labeled with one (*) or two asterisks (**) are significantly different from the no endophyte (E−) stressed control (p≤0.05 or p≤0.01, respectively; ANOVA, followed by post-hoc LSD test).
Figure 28:
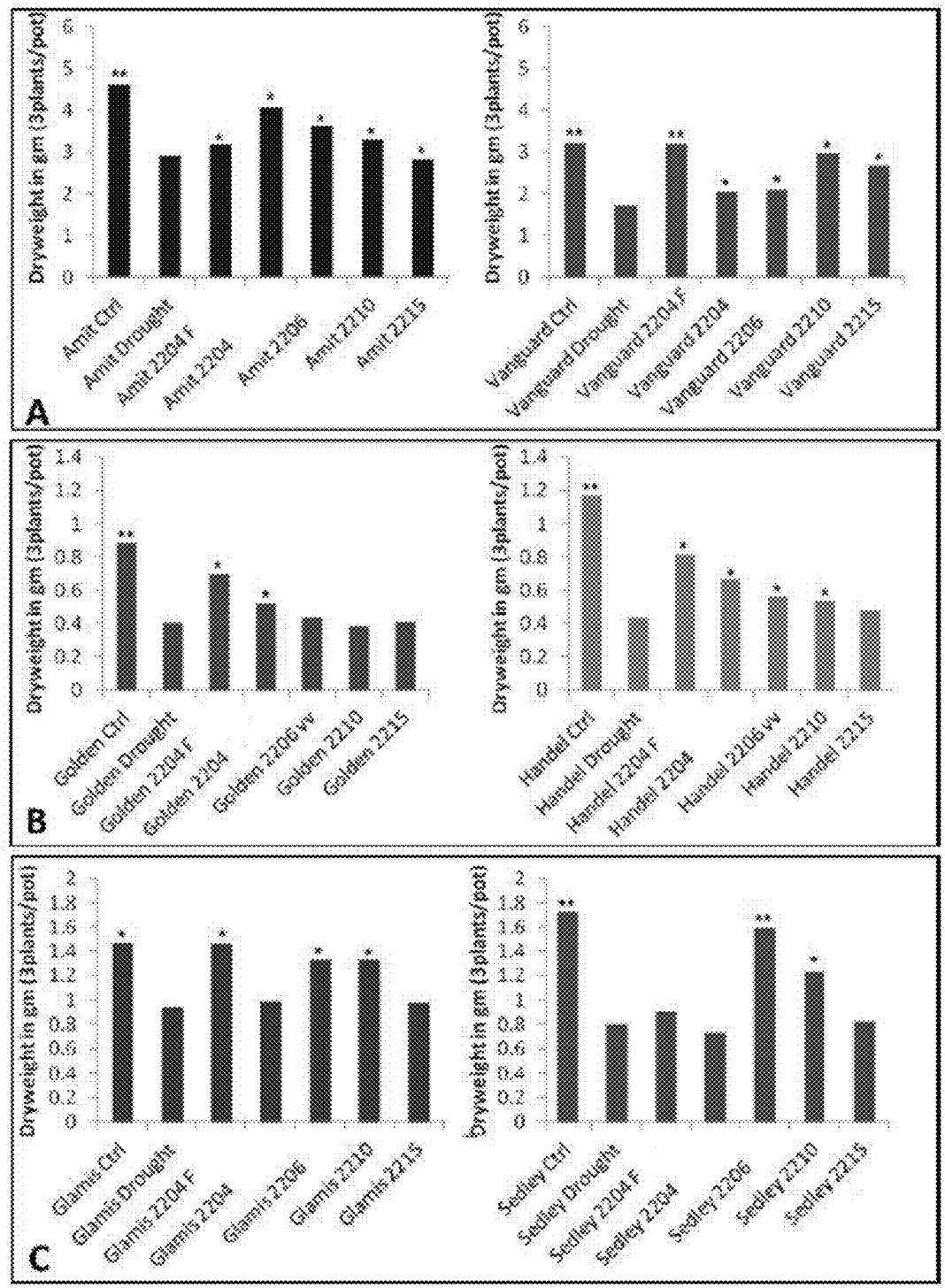
FIG. 28 shows roots dry weight of (A) chickpeas, (B) peas, and (C) lentils under drought stress in the greenhouse. Bars labeled with one (*) or two asterisks (**) are significantly, or highly significantly, different from no endophyte (E−) stressed control (p≤0.05 or p≤0.01, respectively; ANOVA, followed by post-hoc LSD test).

In summary, the results show that each SMCD strain positively affects several agricultural parameters on pod production or yield (FIG. 27), and biomass of stem (FIG. 26) and root (FIG. 28) in chickpea (A), pea (B), lentil (C) and under drought stress. Overall, crop genotypes colonised by the symbiotic endophyte (E+) became more resistant to drought vs. heat stress. The level of efficacy of the tested endophytes in conferring drought tolerance varied with the particular plant organ: the pod yield was highly improved in Glamis by SMCD 2204, in Vanguard by SMCD 2204F, in Sedley by SMCD 2206, in Golden by SMCD 2210, and in Handel by SMCD 2215.

Stem:

The following endophytes showed the best response to drought stress: Chickpea: Amit: SMCD 2204F, Vanguard: SMCD 2206; Pea: Golden: SMCD 2204, Handel: SMCD 2204; SMCD 2210; SMCD 2215; Lentil: Glamis: SMCD 2204F; SMCD 2206. Sedley: SMCD 2204F; SMCD 2206.

Pods:

The following endophytes showed the best response to drought stress: Chickpea: Amit: SMCD 2204; SMCD 2210. Vanguard: SMCD 2204; SMCD 2206; SMCD 2215; Pea: Golden: SMCD 2210; SMCD2215. Handel: SMCD 2204F; SMCD 2206; SMCD 2215; Lentil: Glamis: SMCD 2204F; SMCD 2206. Sedley: SMCD 2210; SMCD2215.

Root:

The following endophytes showed the best response to drought stress: Chickpea: Amit: SMCD 2204; SMCD 2215. Vanguard: SMCD 2204F; SMCD 2206; Pea: Golden: SMCD 2204F; SMCD2215. Handel: SMCD 2204F; Lentil: Glamis: SMCD 2204F; SMCD 2206; SMCD 2210. Sedley: SMCD 2206; SMCD 2210.

Example 8

Figure 29:
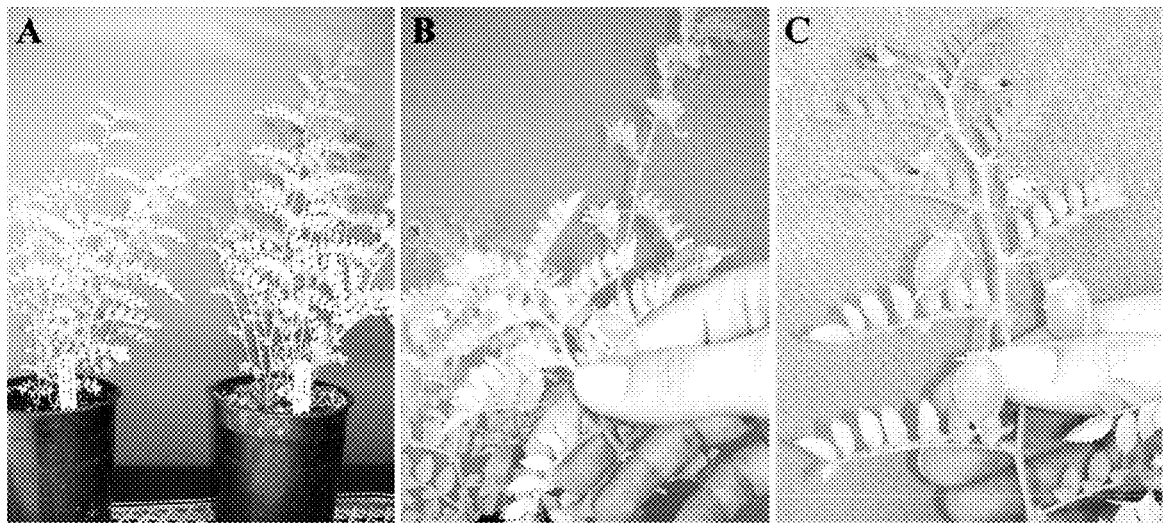
FIG. 29 shows A. Chickpea Vanguard flowering plants bearing pods under drought stress in a greenhouse—left plant is non-symbiotic (E−) and right plant is symbiotic with strain SMCD 2215 (E+); B and C, Chickpea Vanguard plants bearing pods under drought stress in a greenhouse—(B) non-symbiotic and (C) symbiotic with SMCD 2215.
Figure 30:
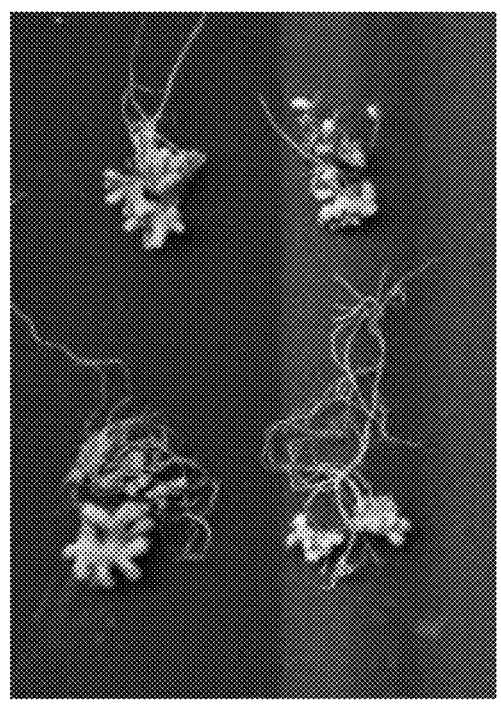
FIG. 30 shows root nodulation of pea varieties under heat stress in a phytotron: Hendel (Above) and Golden (Below) inoculated (left) and uninoculated (right) with SMCD 2215. Note: in all samples natural infection with *Rhizobium* sp. from pea seeds has been observed.

*Streptomyces* sp. SMCD 2215 Increases *Rhizobium* Activity and Nodulation Frequency in Peas Under Heat Stress As was recently observed for another *Streptomyces* species, *S. lydicus* WYEC10 [Tokala et al. 2002], the *Streptomyces* sp. nov. SMCD2215 colonizes the roots of young pea seedlings from seeds produced from plants grown under control conditions. It specifically enhances plant flowering and pod yield (FIG. 29), and root nodulation by *Rhizobium* sp. (FIG. 30), a native endophytic colonizer of pea seeds discovered in this study (Table 5). Vegetative hyphae of *Streptomyces* sp. nov. SMCD2215 colonize the cells of emerging nodules as discovered by culture plate (PDA), fluorescence microscopy (Carl Zeiss Axioskop 2) and PCR (BioRad) amplification methods [Schrey and Tarkka 2008]

Example 9

Endophytes Confer Abiotic Stress Tolerance to Pulses Via Enhanced Seed Viability Pulse crops refer to a group of more than sixty different grain legume crops grown around the world. The seeds of pulse crops are important to human nutrition. The chief constraints to pulse production are biotic and abiotic stresses such as drought, heat, cold and salinity. Recent research suggests that endophytic microbe-plant interactions are an instrumental determinant of plant adaptation.

This study hypothesizes that endophytes increase the rapidity and uniformity of seed germination under optimal and stress conditions in-vitro. The aim was, firstly, to measure the intrinsic symbiotic capacity of endophytes to trigger germination; and, secondly, to measure the efficiency of the compatible endophytes in conferring heat and drought resistance to pulses genotypes.

Material and Methods

Figure 31:
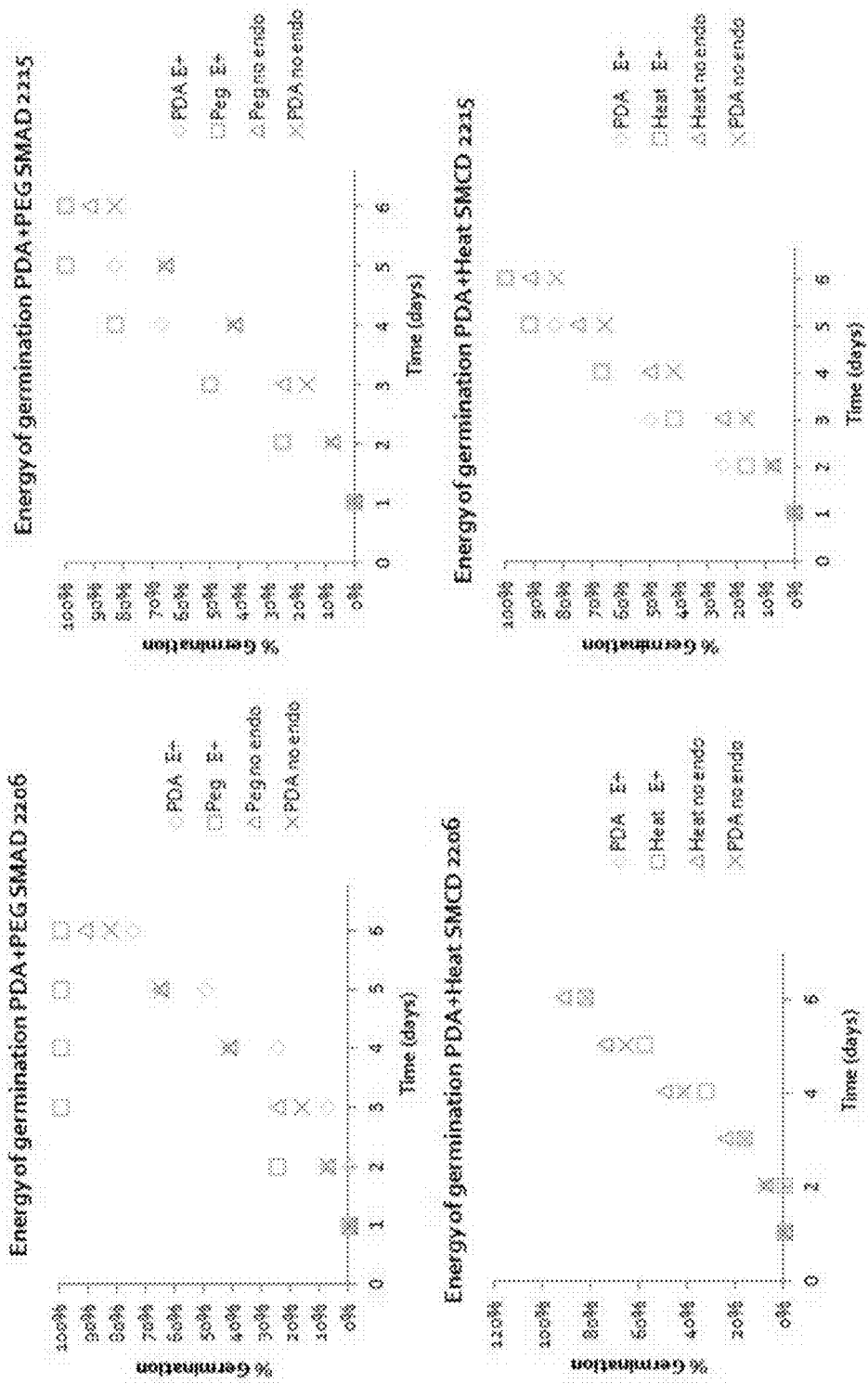
FIG. 31 shows SMCD2206 and SMCD 2215 considerably increase energy of seed germination (≥50%) in Glamis (lentil) as a function of time under heat and drought in vitro.
Figure 32:
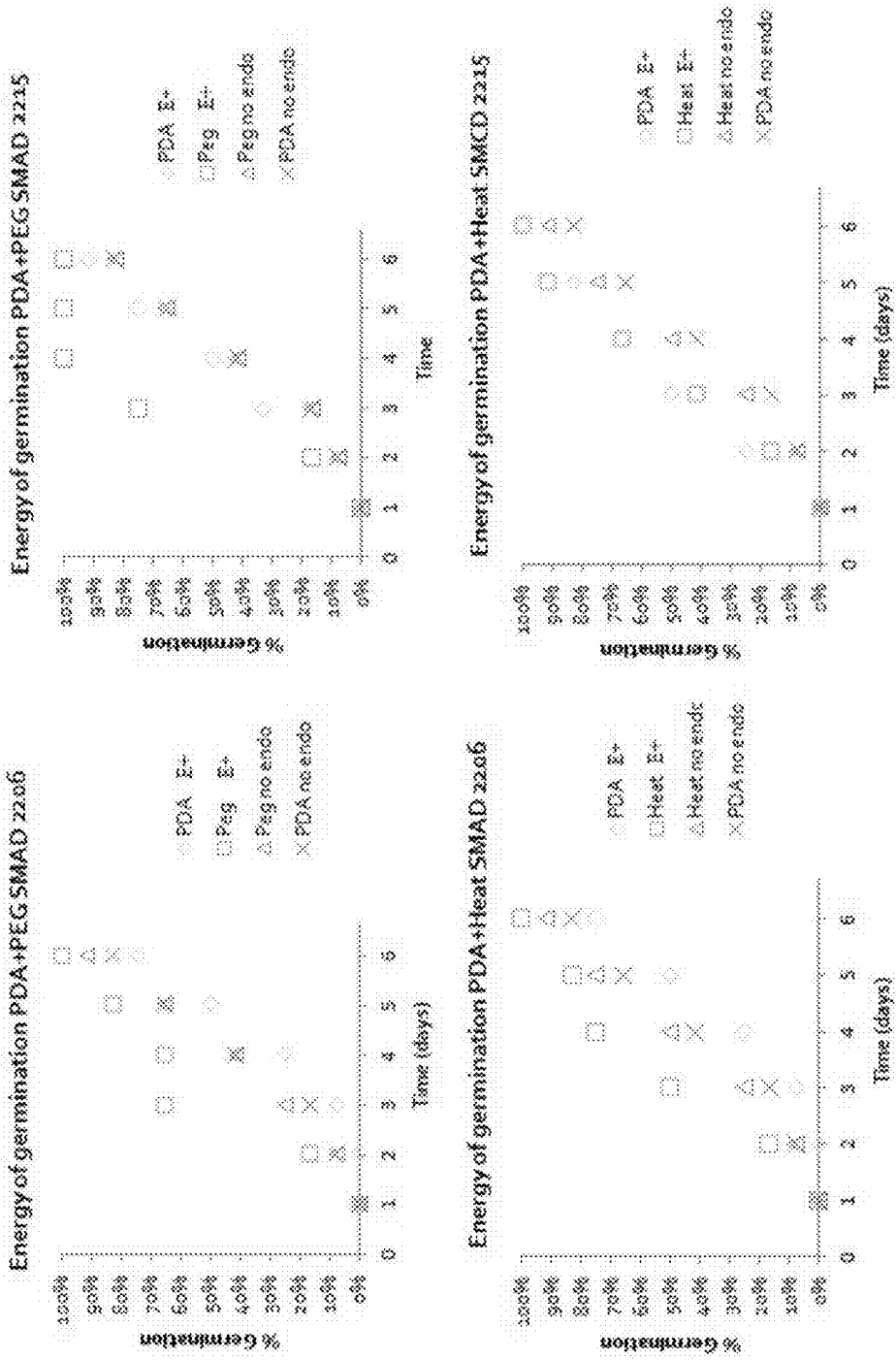
FIG. 32 shows SMCD2206 and SMCD 2215 considerably increase (energy of seed germination (≥50%) in Handel (pea) as a function of time under heat and drought in vitro.

Two varieties of pulses, Glamis (lentil) and Handel (pea), were co-cultured with compatible SMCD 2206 and SMCD 2215, fungal and bacterial symbiotic strains, respectively. The endophytic strains' ability to confer stress tolerance to Golden (FIG. 31) and Handel (FIG. 32) genotypes were tested during in-vitro seed germination modelling drought (6% PEG) and heat (33° C.) environments.

Seeds were surface sterilized with 95% ethanol for 20 s, rinsed twice in sterile distilled water for 10 s followed by 2 min in 3% sodium hypochlorite (Javex). Finally, seeds were rinsed in sterile distilled water 4 times. Seeds were inoculated on PDA media with and without endophytes in the dark at room temperature [Abdellatif et al. 2009]. Microbial organisms were grown on PDA for at least three days at room temperature in darkness prior to experimental use. The endophytic ability to confer plant stress resistance was assessed using the energy of germination, which is meant to capture the temporal nature of germination and which is defined as the number of days required to reach 50% of germinating seeds.

Results

The present study demonstrates the differential capacity of fungal or bacterial endophytes to confer drought and heat resistance in pulses specific to a fungal or bacterial strain-plant genotype-abiotic stress combination. This study used molecular and proteomic analyses to better understand the mechanism by which endophytes confer symbiotic stress resistance to pulses.

Figure 33:
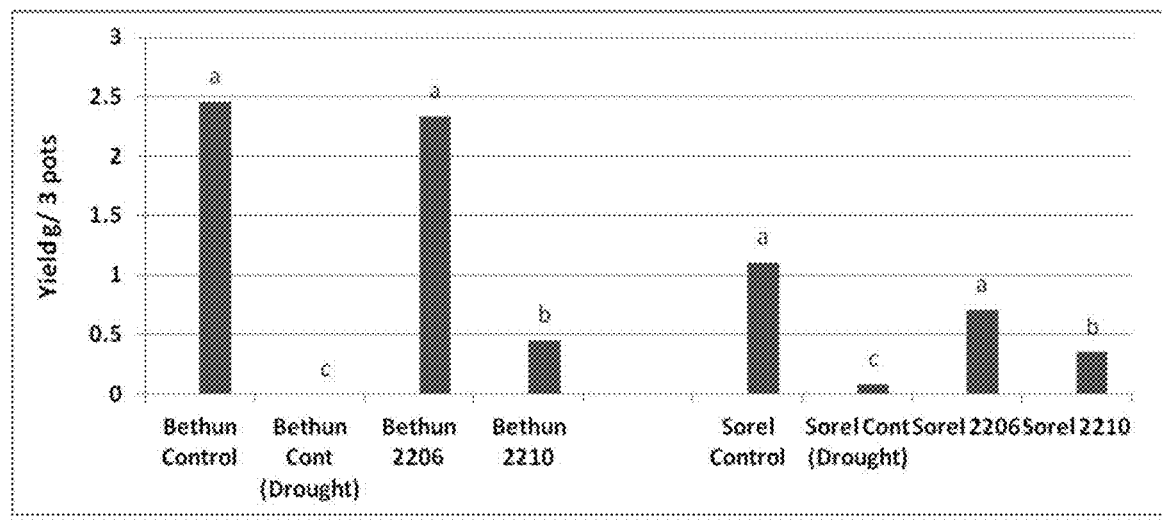
FIG. 33 shows endophytic inoculants (SMCD 2206 and SMCD 2210) improve flax yield under drought conditions in a greenhouse. Different letters above the bars indicate statistically significant differences between samples (p<0.05, Kruskal-Wallis test).

SMCD strains significantly increased the frequency of pulse seed germination under standard in-vitro conditions (FIG. 33). Under stressful conditions, both endophytes (SMCD 2206 and SMCD 2215) increased the frequency of germination when compared to non-colonized seeds. Frequency of germination was from 70-100% in symbiotic treatments and 60-80% germination in the control, meaning that the tested endophytes have the potential to increase seed germination vigour (SGV) by >15%. The highest frequency of germination (100%) was observed in Glamis (lentil) associated with both SMCD 2206 and SMCD 2215 under drought stress vs. heat stress. When co-inoculated with SMCD strains, the energy of germination (>50% germinating seeds) in Glamis was achieved in 2 days under drought and in 3 days under heat conditions. Similar results were achieved in Handel (pea), except that this genotype has inherently a higher ability to support heat shock than Glamis (lentil).

Example 10

Endophytes Enhance Yield of Flax and Canola Genotypes Under Severe Drought Stress in Greenhouse Experiment The aim of this study was to use three randomly selected isolates (SMCD 2206, SMCD 2210 and SMCD 2215 and to expand the efficiency test on flax and canola yield production under drought stress.

Material and Methods

The experimental design, flax (Bethun and Sorel) and canola (1768S) seed manipulation, endophytic inoculant (SMCD 2206, SMCD 2210 and SMCD 2215) application, drought conditions, and yield assessment are as detailed under Example 5 with small modifications. Briefly, control plants were watered to 100% water retention capacity three times per week, while drought stressed plants were watered to 100% water retention capacity weekly. This drought regime was adopted in order to mimic the natural cycle of drought that can occur during the Canadian prairie growing season in which no precipitation falls for seven consecutive days, or more.

Results and Discussion

Figure 34:
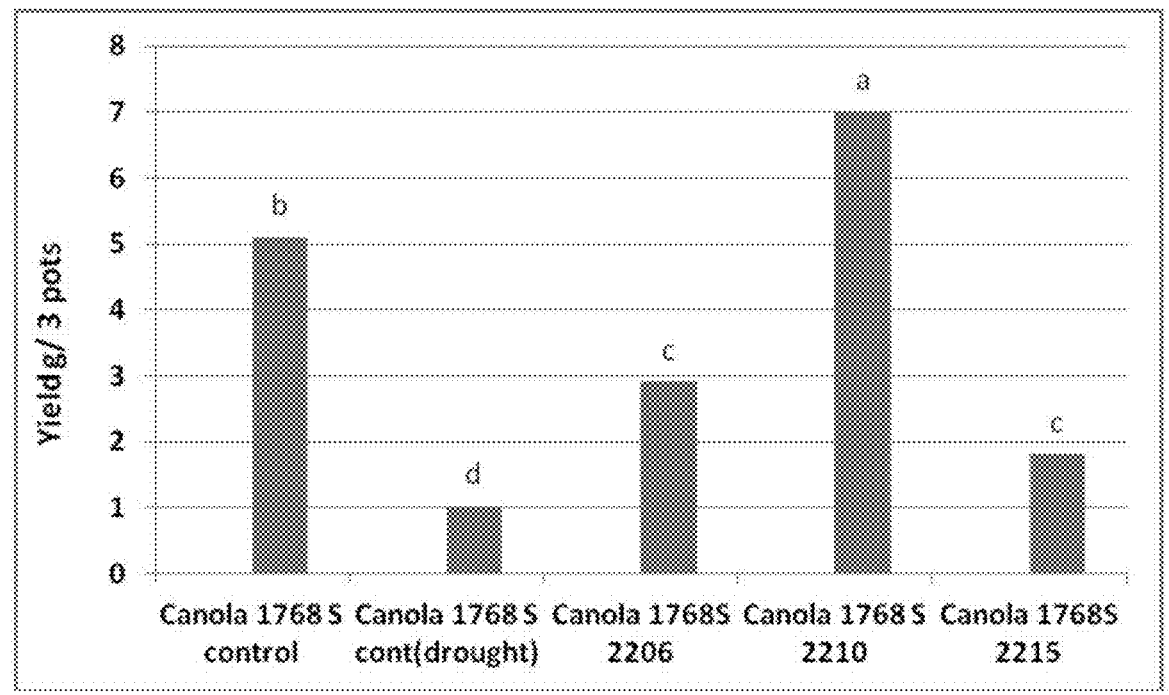
FIG. 34 shows endophytic inoculants (SMCD 2206, SMCD 2210, and SMCD 2215) improve Canola yield under drought conditions in a greenhouse. Different letters above the bars indicate statistically significant differences between samples (p<0.05, Kruskal-Wallis test).
Figure 35:
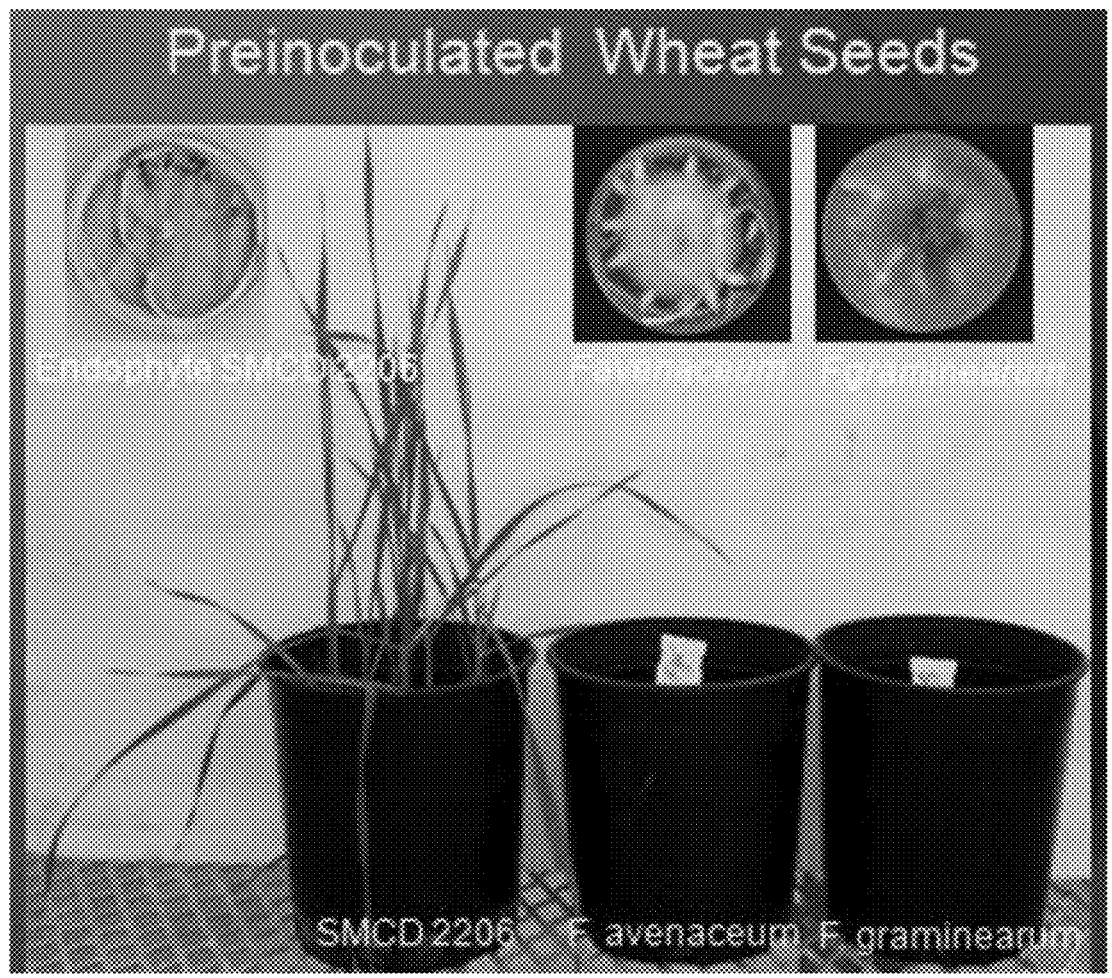
FIG. 35 shows the survival of wheat seeds pre-inoculated in-vitro (plates in above row) and wheat seedlings pre-inoculated in greenhouse (pots in below row) with endophytic SMCD 2206-showing healthy plant growth, and with pathogenic *Fusarium avenaceum* and *Fusarium graminearum*—showing disease symptoms and death of plants.

Severe drought conditions compromised non-symbiotic flax yield, while endophytic inoculants SMCD 2206 and SMCD 2210 dramatically improved flax yield in these same conditions. In particular, under drought conditions, SMCD 2206 maintains a nearly 100% yield in Bethun while SMCD 2210 provides a 50% yield compared to the unstressed control in the greenhouse (FIG. 34). In terms of canola, an improved yield was registered in combination with SMCD 2210 (>100%), followed by SMCD 2206 (~50%) and SMCD 2215 (~30%) compared with unstressed control (FIG. 35).

Figure 36:
FIG. 36 shows *Fusarium* inoculants produced on wheat kernels.
Figure 37:
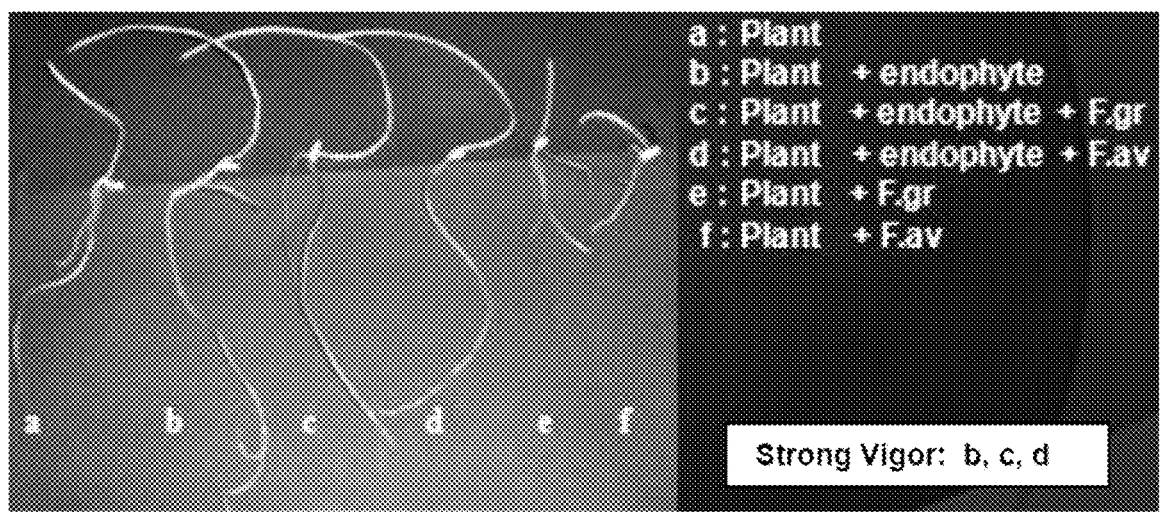
FIG. 37 shows that post-emergence damping-off has been prevented by SMCD 2206 endophyte in greenhouse.

The bioprotection capacity was also tested in greenhouse against *Fusarium avenaceum* and *F. graminearum*. Autoclaved seeds were infected by Fusaria inoculants in darkness for 7 days at 25° C. (FIG. 36), and were inoculated by endophytes produced on petri plates as described by Abdellatif et al. [2009].

Mixed pot soil was inoculated with twenty seeds bearing *Fusarium*. The composition of mixed soil was 55-65% Canadian Sphagnum Peat Moss, Perlite, and Limestone mixed with sand. Standard greenhouse conditions were 8 h day light interchanged with a 16 h photoperiod (1000 lux) regime under a relative humidity of 70% and a constant temperature of 25° C.±2° C.

Plants treatments were as follows:
T1: Untreated plants (control)
T2: Plant+endophyte
T3: Plant+pathogen, *Fusarium avenaceum*
T4: Plant+pathogen, *Fusarium graminearum*
T5: Plant+endophyte fungus+*Fusarium avenaceum*
T6: Plant+endophyte+*Fusarium graminearum*

Each treatment was replicated in three pots, and seedlings were watered three times a week under controlled conditions. The endophyte-root colonisation was tested using a fluorescence microscope to distinguish symbiotic vs. pathogenic endophyte-wheat relationships [Abdellatif et al. 2009].

Figure 38:
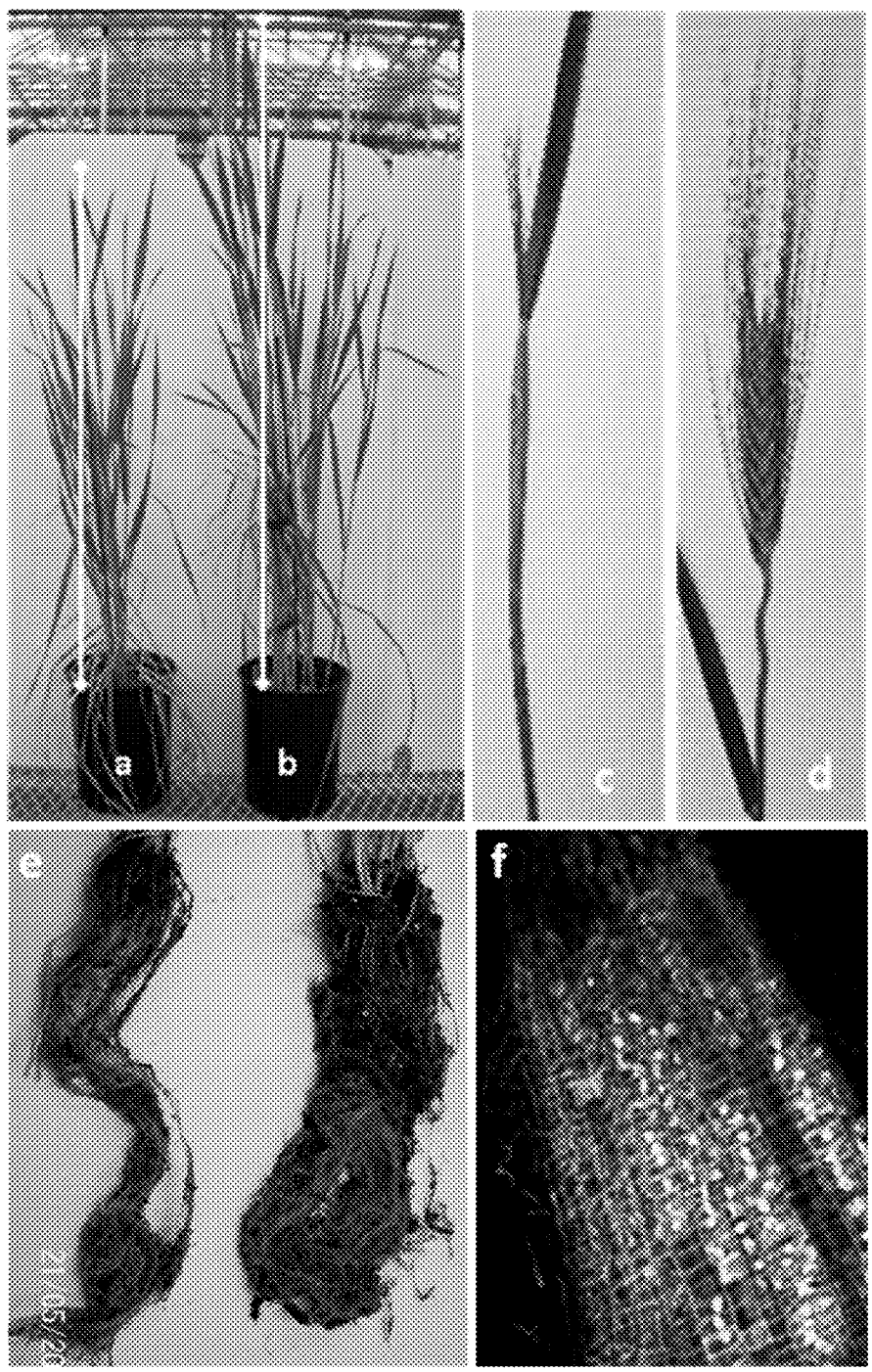
FIG. 38 shows wheat biomass (aerial a-d and root e-f) improved in the presence of SMCD 2206 endophyte compared to untreated plants. (a) control plant (E−), (b) inoculated plant (E+), (c) control flowering plant, (d) inoculated flowering plant, (e) control plant (E−, left) compared to SMCD 2206 inoculated plant (E+, right), and (f) fluorescent microscopy of SMCD 2206 wheat root-colonization (E+).
Figure 39:
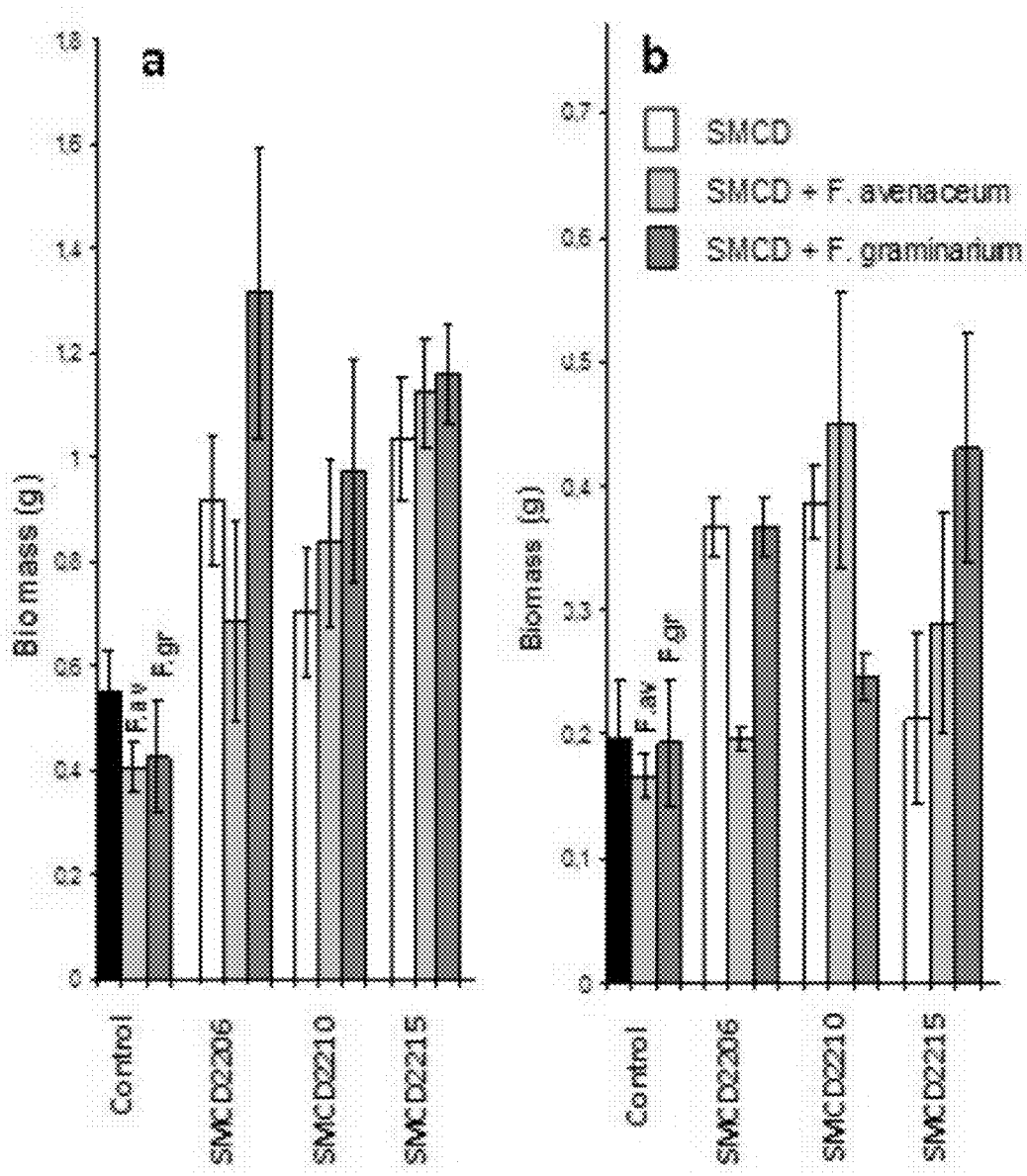
FIG. 39 shows aerial plant biomass/plant (left) and underground (root) biomass/plant (right) in control (E−) and SMCD inoculated plants (E+) against *F. graminearum* and *F. avenaceum*. Vertical error bars on data points represent the standard error of the mean.
Figure 40:
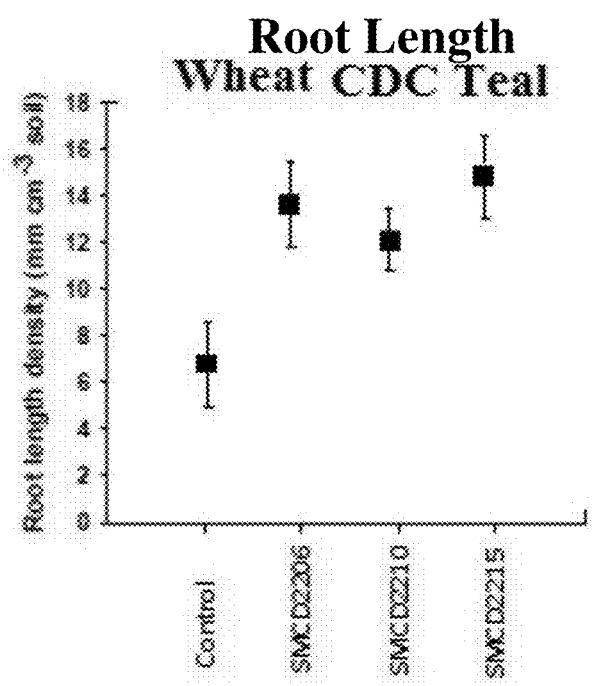
FIG. 40 shows root length in control plant (CDC Teal) without SMCD endophyte compared to inoculated plant with SMCD strains. Bars on data points represent the standard error of the mean.

FIGS. 37-40 show the positive effect of endophytes on wheat post-emergency seedling resistance (FIG. 37), foliage and root biomass (FIG. 38 and FIG. 39), and flowering/anthesis stage and spikes (FIG. 38, FIG. 39, and FIG. 40). All tested endophytes induced well-developed foliage compared to control, as well as well-developed flowers in the presence of endophytes.

To confirm the ability of the endophytes to stimulate mature plant growth in the presence of *Fusarium* pathogens, the performance of the flowering stage bearing the spikes we assessed as a more advanced growth stage.

Figure 41:
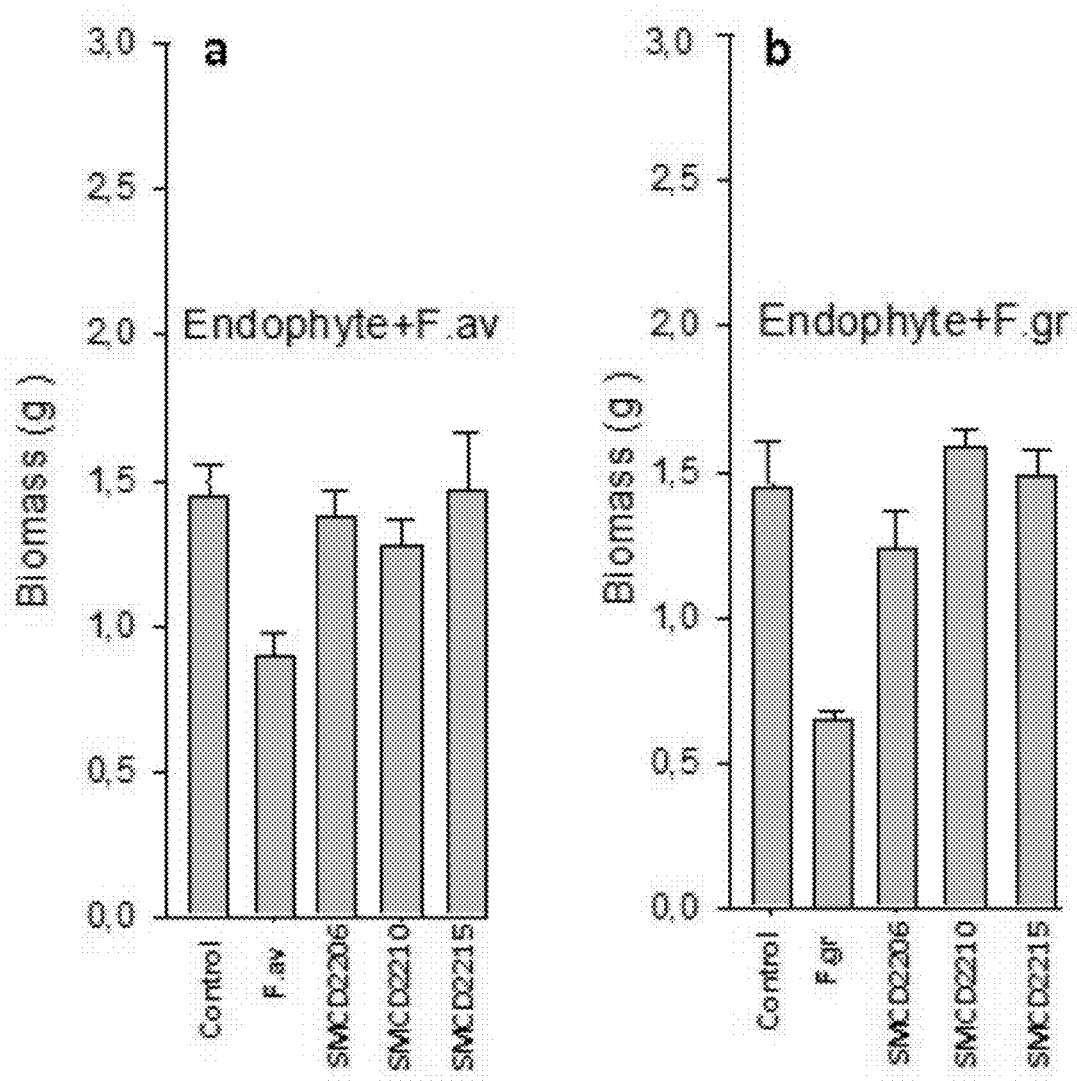
FIG. 41 shows dry weight of kernels/plant (TEAL cultivar) using the double pre-inoculation approach: a) SMCD endophyte+*Fusarium avenaceum* (F.av), and b) SMCD endophyte+*Fusarium graminearum* (F.gr). Vertical error bars on data points represent the standard error of the mean.

The histograms in FIG. 41 illustrate the performance of endophytes in improving the biomass or dry weight of wheat spikes after double inoculation (SMCD endophyte and *Fusarium* pathogen).

Figure 42:
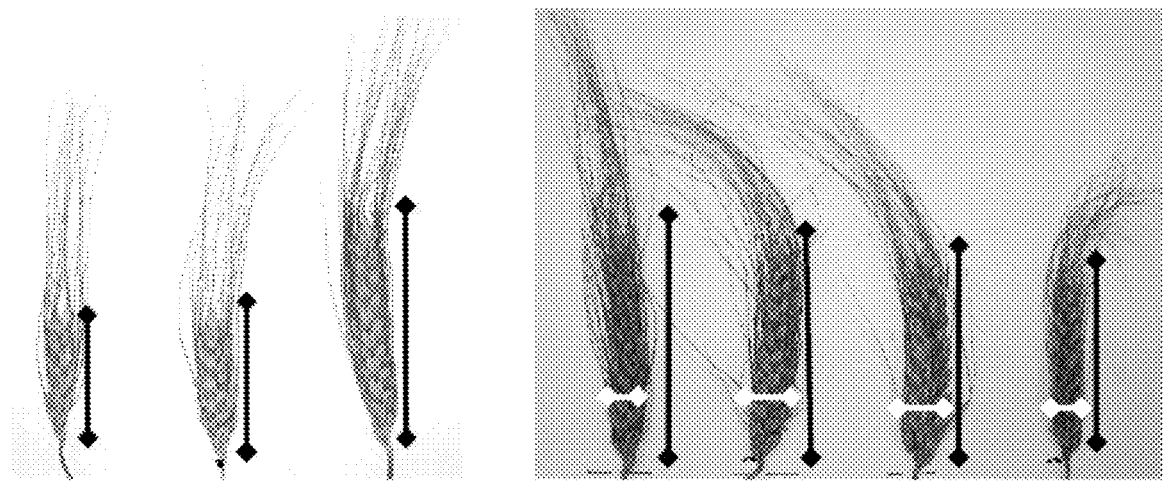
FIG. 42 shows comparison of TEAL spike sizes in the presence of pathogen (negative control) and without presence of pathogen (positive control). Left Figure—from left to right: i) plant+F.gr, ii) plant+F.av, and (iii) plant; Right Figure—from left to right: i) plant; ii) plant+endophyte; iii) plant+endophyte+F. av; and iv) plant+endophyte+F.gr.

The yield of wheat in the presence of an endophyte and *Fusarium* significantly improves using all endophytic strains compared with treatment infected with *F. graminearum* and *F. avenaceum* but without an endophyte (E−) (FIG. 41). Plants treated with the pathogen alone show a significantly lower size of spikes compared to control plants and plants with endophytes (E+) (FIG. 42).

Example 11

Endophyte-Mediated Abiotic Stress Resistance Gene Expression in Pulses

Abstract:

The genomic and proteomic mechanisms of plant endophytes beneficial effects on host plant resistance to abiotic stressors are poorly understood. One of the contemporary theories suggests that the symbiotic plants are protected from oxidative stress produced by heat, drought and salt stressors by the production of antioxidant molecules. The aim of this study is to shed more light on defensive symbiosis of pea, chickpea and lentil genotypes assessing the Pro, SOD, and MnSOD gene expressions triggered by the association between host genotypes and endophytes. The results of this study demonstrated endophyte-mediated gene expression in endophyte-inoculated plants. These genes play an important role and provide the host protection through an enhanced stress tolerance to the tested abiotic stressors.

Materials and Methods

Figure 43:
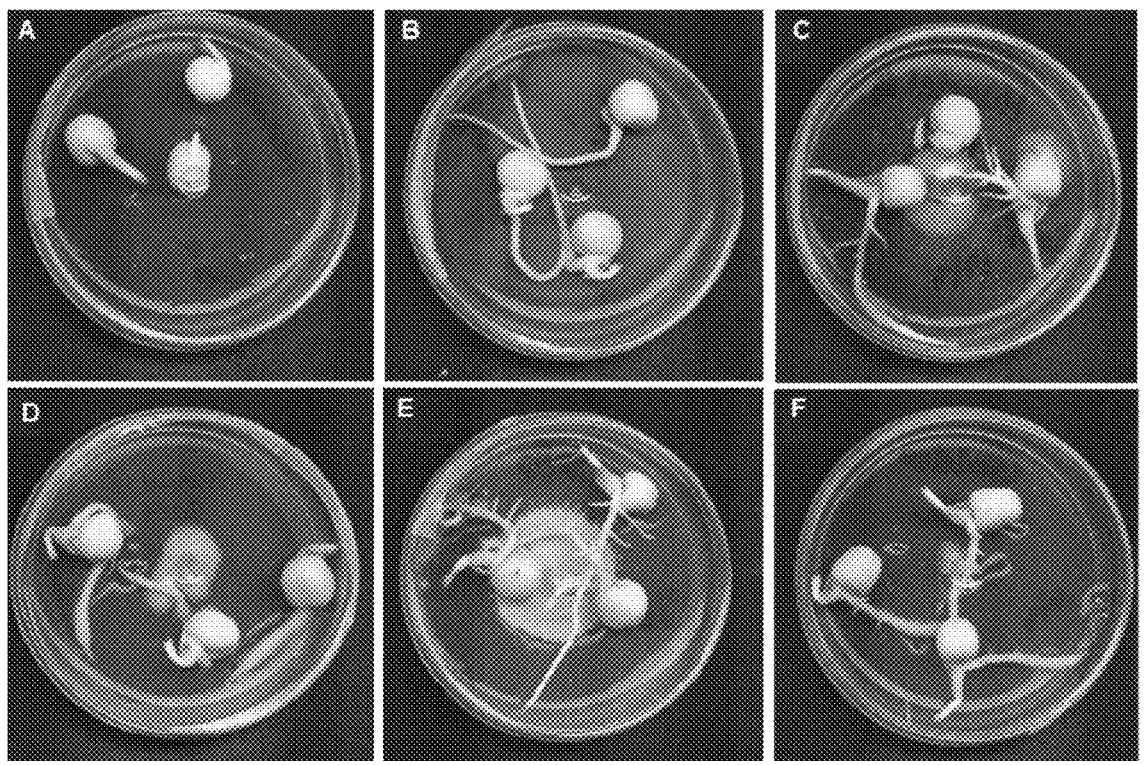
FIG. 43 shows a strain specific pattern of symbiotic seed germination depicting mycovitality: Handel+6% PEG—Control (A), Handel+6% PEG+SMCD 2204 (B); Handel+6% PEG+SMCD 2204F (C), Handel+6% PEG+SMCD 2206 (D), Handel+6% PEG+SMCD 2210 (E), Handel+6% PEG+SMCD 2215 (F) after 7 d at 21° C. in darkness.

Leaves were collected for this analysis from normal and stressed 6 seed varieties (Amit, Vanguard [chick pea] (FIG. 43), Golden, Handel [peas] and Glamis, Sedley [lentils]) with or without endophytes.

Real-Time PCR was used to amplify genes such as Proline (Pro), SOD and Mn SOD using primers as shown in SEQ ID NOs: 8-15 (Table 6), stress proteins generally found to play special roles in protecting cytoplasm from dehydration and in protecting plants by palliating the toxicity produced by the high concentrations of ions. PCR was conducted under the following conditions: 3 min at 95° C. (enzyme activation), 40 cycles each of 30 sec at 95° C. (denaturation) and 30 s at 60° C. (anneal/extend). Finally, a melting curve analysis was performed from 65° to 95° C. in increments of 0.5° C., each lasting 5 s, to confirm the presence of a single product and absence of primer-dimer. Quantitation is relative to the control gene by subtracting the CT of the control gene from the CT of the gene of interest (ΔCT). The resulting difference in cycle number is then divided by the calibrator normalized target value, and the value obtained (ΔΔCT) is the exponent of base 2 (due to the doubling function of PCR) to generate the relative expression levels.

Results

Different gene expressions during drought stress were analyzed. Table 6 shows the genes that were tested. Some of the results obtained from Handel variety when exposed to 6% PEG.

SOD and MnSOD

Figure 44:
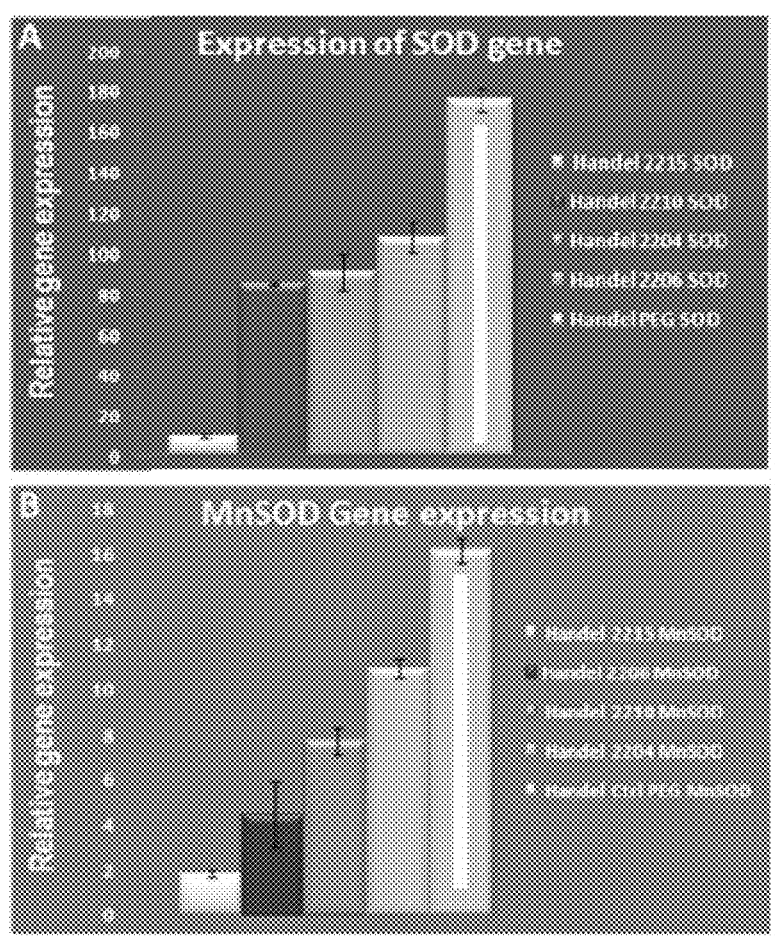
FIG. 44 shows (A) SOD and (B) MnSOD relative gene expressions in Handel exposed to PEG with and without endophytes.

In general, SODs play a major role in antioxidant defense mechanisms. In the present study very high levels of SOD expression were observed in normal (E−, control) leaves exposed to 6% PEG, an almost 200 fold increase. Endophytes played a very significant role in decreasing this stress. Especially, SMCD 2215, followed by and SMCD 2210, SMCD 2204 and SMCD 2206. These symbionts drastically reduced the stress with only a 9 and 24 fold increased expression observed (FIG. 44A).

MnSOD is one of the SOD forms. Control leaves showed a 16 fold increase in the gene expression, whereas SMCD 2215 suppressed the stress and decreased the fold change from 16 fold to 2 fold, followed by SMCD 2206, SMCD 2210 and SMCD 2204 (FIG. 44B).

Proline

Figure 45:
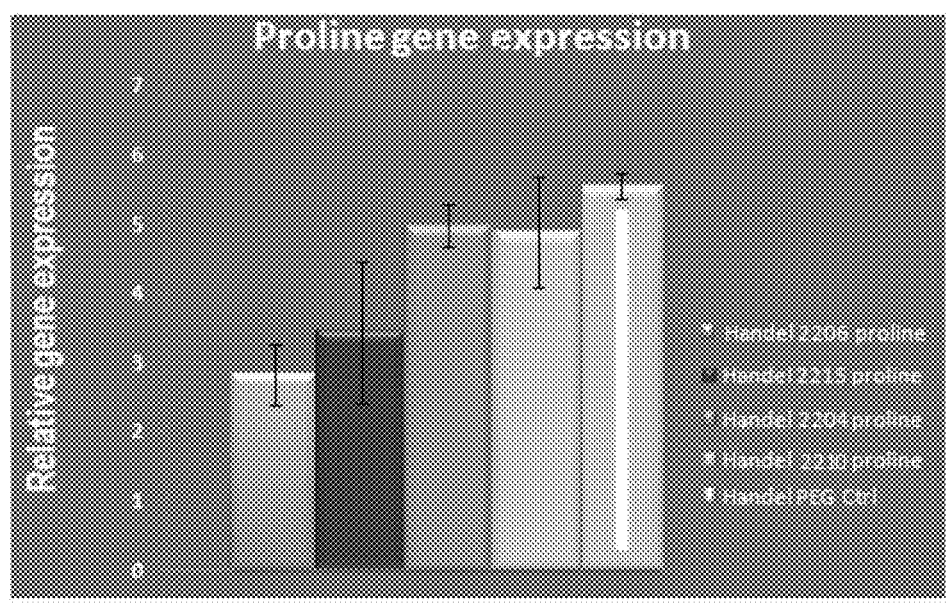
FIG. 45 shows Proline relative gene expression in Handel exposed to PEG with and without endophytes.

Proline is essential for primary metabolism. Proline biosynthesis is controlled by the activity of two P5CS genes in plants. This gene was assessed in Pea variety Handel with endophytes under drought condition. As expected P5CS gene was upregulated and increased expression by 5 fold in the leaves collected from PEG exposed plants. Whereas the leaves collected from seeds associated with SMCD 2206 expressed 2.8 fold followed by SMCD 2215 at 3.4 fold expressed proline coding gene (FIG. 45). These results confirmed that endophytes play major role in stress resistance modifying proline gene expression compared to uninoculated stressed plants.

Example 12

Gene Expression Patterns in Wheat Coleorhiza Under Cold and Biological Stratification Abstract:

Wheat is one of the widely used major crops in the world. However, global wheat production has decreased about 5.5% in last two decades and a further decline has been predicted due to pervasive global warming. Thus, elucidating conditions and techniques that enhance seed germination is of great importance. Cold stratification is a long-known method of releasing seed dormancy and promoting germination. Biological stratification through fungal endophytes can also stimulate seed germination in many cereal crops. Coleorhiza is one of the most active tissues in seed and it is also the first part to emerge out of germinating seeds. To evaluate the efficiency of the stratification methods, germination percentage of wheat seeds was assessed under cold and biological stratification and the expression level of gibberellin and abscisic acid genes in coleorhiza were determined. Both cold and biological stratification treatments significantly (P<0.05) enhanced the rate and efficacy of germination. Spatial distance between the fungal endophyte and seeds is a determining factor of biological stratification as seeds in direct contact with fungal endophyte showed highest germination percentage (up to 86%). High expression of GA3ox2 gene in wheat coleorhiza was found throughout the germination period revealing consistent production of the bioactive GA3 molecule. The 14-3-3 gene expression was lowest under endophyte-direct treatment. The expression of abscisic acid-ABA biosynthesis gene, TaNCED2, was considerably high in cold stratification seeds reflecting the role of abscisic acid as a stress-adaptation hormone. High expression of TaABA8'OH1 gene was also found in coleorhiza. Overall, this study provides molecular evidence of the importance of coleorhiza in germinating wheat seeds. By comparing cold and biological stratification methods, seed germinability can be markedly enhanced through application of fungal endophytes, and the spatial distance between seed and endophyte is a factor driving mycovitality.

Materials and Methods

Wheat Seeds

Seeds of the durum wheat cultivar AC Avonlea with low resistance to environmental stress conditions were used in this study. These seeds were produced by Agriculture and Agri-Food Canada Seed Increase Unit Research Farm in 2006 under greenhouse conditions, and were recommended as free of microbes. Seeds were kept in sterile ziplock bags and stored in 4° C. cold room until further use.

Comparison of Seed Sterilization Protocols

Various methods have been proposed for surface sterilization of wheat seeds. Here four widely acknowledged seed-sterilization methods were compared to identify the best suitable protocol that efficiently sterilize seed-surface without affecting seed quality and vitality in this variety of wheat. In the first method, seeds were surface sterilized with 95% ethanol for 10 s, followed by rinsing in sterile distilled water three times for 1 min [Zhang et al., 2007. BMC Genetics 8]. Second protocol was bleach-sterilization where seeds were surface sterilized in 5% sodium hypochlorite for 3 min followed by thorough rinsing in sterile distilled water three times for 1 min. In the third protocol, seeds were surface sterilized with 95% ethanol for 10 s, rinsed in sterile distilled water, then submerged for 3 min in 5% sodium hypochlorite, rinsed three times in sterile distilled water and placed on potato dextrose agar (PDA) for germination [Abdellatif et al. 2009]. The fourth method was vapour phase sterilization of seeds with chlorine gas [Desfeux et al., 2000]. In fume hood chamber, a small beaker with 20 ml bleach is placed in a 5 litre snaptite box. Wheat seeds were placed in a 96 well-plate and kept in the snaptite box. Then 3 ml of concentrated hydrochloric acid was added into the small beaker to create chlorine gas. Lid was kept closed for 4 hours to retain seeds in contact with chlorine gas. After sterilization, the 96 well-plate was placed for 1 hour in a laminar flow hood to disperse trace chlorine gas. Sterilized seeds were then rinsed three times in sterile distilled water and were plated out on PDA plates. Comparison of these sterilization methods suggests that chlorine gas sterilization protocol was the most effective method showing 80% germination without contamination while control seeds had highest percentage of contamination (Table 7). Although bleach and ethyl methods successfully inhibited contamination, seed germination was affected considerably. Therefore, chlorine gas protocol is a highly efficient method of sterilization of wheat seeds and it was selected to sterilize the seeds required for experiments conducted in this study.

Cold and Biological Stratification

For cold stratification, surface sterilized seeds were kept on moist filter paper at 4° C. cold-room for 48 hours [Mukhopadhyay et al., 2004; Wu et al., 2008]. After 2 days, cold stratified seeds were taken to room temperature where they were quickly rinsed in sterilized distilled water and placed on potato dextrose agar (PDA) plates. For biological stratification, sterilized seeds were incubated in presence of SMCD 2206. Fungal endophyte was grown on PDA at room temperature in darkness for at least three days before use. To assess this efficiency, wheat seeds were germinated in direct contact and at a certain distance from the fungal endophyte. An agar plug (5 $mm^2$) of the endophyte dissected from the margins of a parent colony was placed in the centre of a 90 cm petri dish with PDA. Then 10 surface sterilized seeds were placed at the periphery of the petri dish encircling the fungal agar plug at approximately 4 cm distance. All petri dishes were sealed with 5 layers of Parafilm® (Pechiny Plastic Packaging) to avoid any biological contamination and diffusion of volatile/gaseous compounds. The impact of direct-contact of the fungal endophyte was elucidated by placing a 3 $mm^2$ agar plug between two adjacent surface sterilized wheat seeds and 5 $mm^2$ plug in the centre of the PDA plates. All treatments were carried out with three replicates of PDA plates with ten surface sterilized seeds on each plate. Petri dishes were incubated in a bench-top incubator at room temperature (~20° C.) in darkness. Incubation time was recorded and data collection and coleorhiza isolation were carried out after 24, 48, and 72-hours.

Germination Percentage

Emergence of early radicles was carefully monitored. Percentage of germination was calculated by estimating the number of seeds germinated out of 10 wheat seeds on each PDA plate. The 50% germination rate was assumed as the energy of germination. The efficacy of germination in different treatments was calculated by following equation:

$$\text{Efficacy} = \% \text{ germination in a treatment} - \% \text{ germination in control} \quad [\text{Eqn. 1}]$$

Rate of germination was observed for all treated samples and replicates. For Day 2 and Day 3 samples, germination rate was monitored from Day 1 to assess the overall vitality. The PDA plates were kept sealed throughout the data collection period.

Isolation of Coleorhiza

After observing the rate of germination, PDA plates were immediately transferred to a sterile biosafety hood chamber for coleorhiza isolation. Wheat seeds were carefully dissected under compound microscope and layers of coleorhiza were cleaved off using sterilized needle and scalpel. Isolated coleorhizas were stored in an RNase-free sterilized microcentrifuge tube. Seeds from all biological replicates of a treatment were combined and approximately 20 to 30 coleorhizas were isolated to obtain optimum amount plant material for RNA extraction.

RNA Extraction and cDNA Synthesis

To avoid any degradation in plant material, RNA extraction was carried out forthwith after coleorhiza isolation on each day. Approximately 20 mg of coleorhiza samples were taken for RNA extraction. Total RNA was extracted using Aurum™ Total RNA Mini Kit according to manufacturers instructions (Bio-Rad Laboratories). RNA concentration was spectrophotometrically measured by Nanodrop (Thermo Scientific). Immediately after RNA extraction, cDNA synthesis was performed using iScript cDNA Synthesis Kit following manufacturers instructions (Bio-Rad Laboratories). A 600 ng aliquot of RNA was taken for cDNA synthesis. Reverse transcription was carried out at 42° C. for 30 minutes with a final denaturation at 85° C. for 5 minutes.

Quantitative Real-Time PCR

Expression of gibberellin and abscisic acid functional genes was estimated by relative quantification using quantitative real-time PCR (QRT-PCR). Various catabolic and biosynthetic genes were selected to assess their respective roles in cold and biological stratification. Wheat actin gene of 131 bp length fragment was used as the internal control [Nakamura et al., 2010]. QRT-PCR was performed using a MJ-Mini Gradient Thermal Cycler (Bio-Rad Laboratories) following manufacturers instructions. The PCR condition was 1 cycle of 95° C. for 1 minute and 40 cycles of 94° C. for 20 s, 60° C. for 30 s, and 72° C. for 1 min. For real-time PCR, cDNA samples from the treatments were used and all reactions were carried out in three replicates and two negative controls. Each 25 µl reaction contained 18 µl of iQ™ SYBR® Green supermix (Bio-Rad Laboratories), 10 pmol of the appropriate forward and reverse primers, 2.5 µl bovine serum albumin, and 25 ng template cDNA. Relative quantification was performed according to Zhang et al. [2007].

Expression levels were calculated using cycle threshold (Ct) value determined according to manually adjusted baseline. The difference between the Ct values of target gene and actin ($Ct^{target} - Ct^{actin}$) was estimated as $\Delta Ct$ and then the expression level was calculated as $2^{-\Delta Ct}$. The mean values of $2^{-\Delta Ct}$ were used to assess difference in expression between control and stratification treatments. To ensure the specificity and consistency of amplicons, melting curve analysis and agarose gel electrophoresis were performed after each QRT-PCR run.

Sequencing

Amplicons of Actin and various GA and ABA genes were purified using BioBasic PCR Purification Kit (Bio Basic Inc.). For each treatment, purified amplicons were sent for sequencing at Plant Biotechnology Institute (NRC-PBI). Gene sequences were identified by Basic Local Alignment Search Tool (BLAST) analyses as found at blast.ncbi.nlm.nih.gov.

Statistical Analysis

One way analysis of variance of germination percentage and gene expression data was performed using IBM SPSS Statistics software version 19. Differences between control and stratification treatments were examined with the Duncan's post-hoc test.

Results and Discussion

Percentage and Efficacy of Germination

Figure 46:
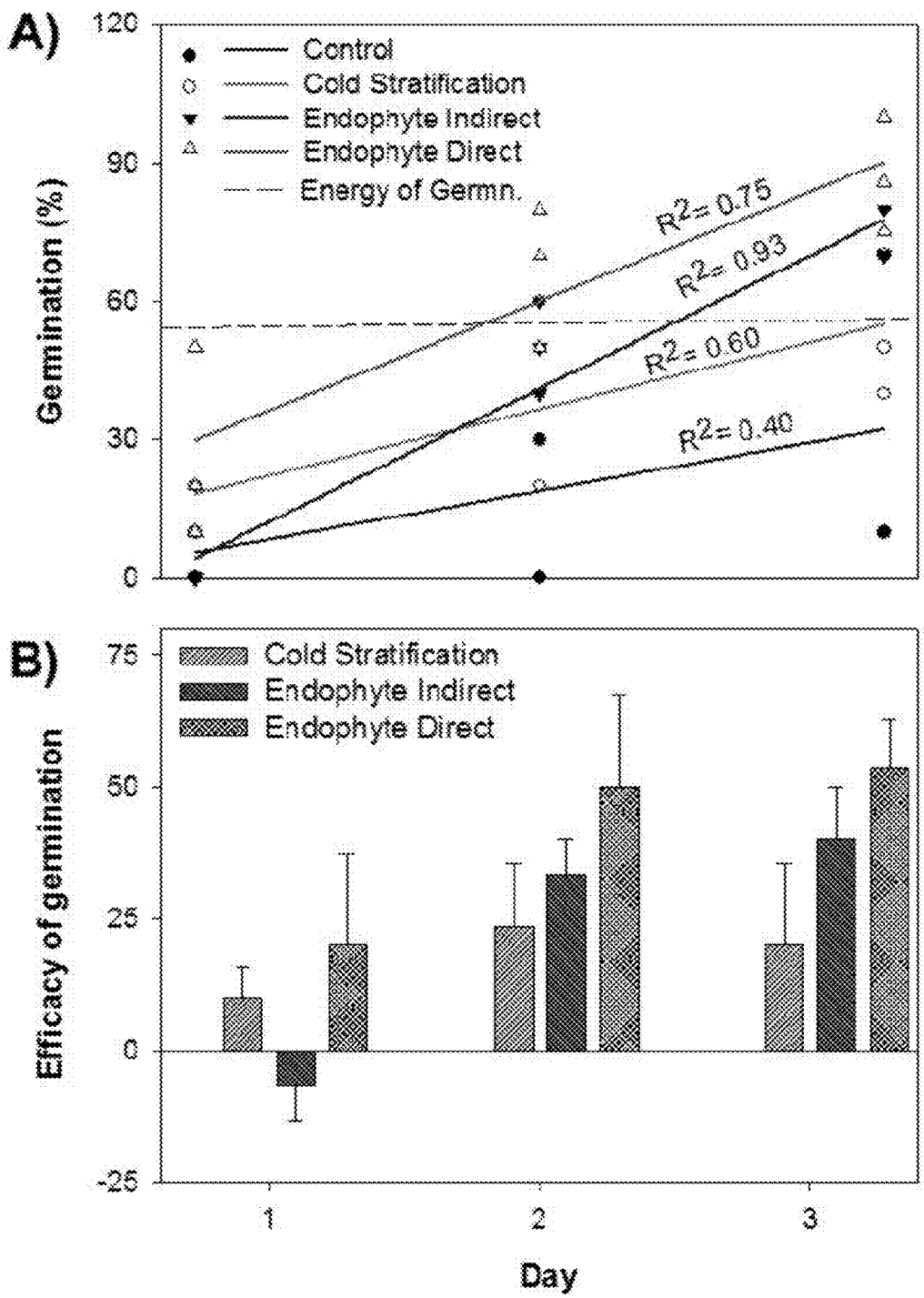
FIG. 46 shows germination of wheat seeds in vitro after three days on potato dextrose agar (PDA). Cold stratification was imposed by keeping seeds at 4° C. cold-room for 48 hours. For endophyte-indirect and endophyte-direct treatments, seeds were germinated at approximately 4 cm distance and in direct contact respectively. A) Percentage of germination in comparison with energy of germination (50% germination). B) Efficacy of germination of wheat seeds subjected to cold and biological stratification. Efficacy was calculated by subtracting the germination percentage of control from treated seeds.

Both cold stratification and biological stratification treatments significantly enhanced the rate of germination with all three treatments exhibiting higher germination percentage than control (FIG. 46A; Table 8). Endophyte-direct showed highest germination percentage after each day and increased 60% from Day 1 to Day 3. Throughout the germination period (3 days) it demonstrated significantly (P<0.05) higher germinability than the other three treatments. Only biological stratification treatments produced more than 50% germination after Day 2. Interestingly, endophyte-indirect treatments showed no germination after Day 1 but produced a remarkable 50% germination after Day 2. Cold stratification treatment demonstrated no significant difference from control after Day 1, and then steadily increased showing significant difference after Day 2 and Day 3. Pattern of increase in germination is also reflected in $R^2$ values. Whereas control showed an $R^2$ value of 0.40, cold stratification and endophyte-direct treatment showed 0.60 and 0.75 respectively. On the other hand, owing to its 50% increase from Day 1 to Day 2, endophyte-indirect treatment had the highest $R^2$ value of 0.93, which is about 2.5 times higher than control. Energy of germination is a critical parameter determining the capacity of seeds to break dormancy and start germination. Energy of germination is assumed as the percentage of seed germination after certain time or the number of days necessary to achieve 50% germination. Endophyte-direct showed highest efficacy followed by endophyte-indirect and cold stratification (FIG. 46B). As there was no germination in endophyte-indirect seeds after Day 1, the efficacy of germination was negative. Overall, the stratification treatments showed tremendously positive result by reaching 50% germination after 48 hours.

Stratification plays an important ecological role in the release of primary dormancy and enhancement of seed germination [Bewley and Black 1982; Probert et al., 1989]. Alleviation of seed dormancy and improvement of germination through cold stratification have been achieved in many species including grasses [Schutz and Rave 1999], mulberry [Koyuncu 2005], pine [Carpita et al., 1983], tobacco [Wu et al., 2008], rice [Mukhopadhyay et al. 2004], and apple [Bogatek and Lewak 1988]. Germination was also increased by cold stratification in 33 annual weed species and stratification has been proposed to even be capable of nullifying differences in seed germinability between populations [Milberg and Andersson 1998]. However, little information is available on the impact of cold stratification on wheat seed germination. This study found that the effect of cold stratification requires an initial period and thus seed germination was not significantly different from the control on Day 1. However, it demonstrated considerable impact on germination from Day 2 and the percentage of germination increased as much as 20% higher than the control. The time period of cold stratification in this study was selected from previous reports that showed a period of 48 hours is effective for cold stratification in tobacco [Wu et al., 2008] and rice [Mukhopadhyay et al. 2004]. Earlier studies have shown that the impact of cold stratification is proportional to its time-length [Baskin et al. 1992; Cavieres and Arroyo, 2000]. The findings support this and further extend the notion to envisage that a slightly longer stratification period (~4 days) may be required for wheat to attain maximum germinability.

Several reports have shown the enhancement of seed germination through the application of fungal endophytes [Vujanovic 2007b; Hubbard et al. 2012; Vujanovic and Vujanovic 2007]. The present study supports the concept of "mycovitalism", which is the increase of vitality through fungal colonization. Fungal endophytes are well known to produce volatile compounds that affect plant phenophases [Mitchell et al., 2009; Strobel et al., 2004]. Thus, endophytes may be capable of affecting seed germination even when they are not in direct contact with seeds, and this attribute is particularly useful in field conditions. Here it was also tested how physical distance may influence seed germination under biological stratification. These findings suggest that seeds in direct contact with fungal endophyte are undoubtedly more benefitted than their counterparts. Endophyte-direct produced highest percentage and efficacy of seed germination on each day of the germination period. Similar to endophyte-direct contact, seeds placed at 4 cm from the endophyte also germinated at a significantly higher rate than control. However, the germination percentage and efficacy were indeed affected by the distance and indirect-contact seeds have between 14% and 27% less germination than direct-contact ones. Furthermore, no germination activity was observed on Day 1 which was followed by a sharp rise (50%) on Day 2. Seed germination is an extremely complex process and its underlying mechanisms are relatively less understood [Nonogaki et al., 2010]. Thus it is not clear how fungal endophytes facilitate the release of dormancy and onset seed germination. Considering fungi are capable of producing a range of plant-growth promoting substances, it is possible these substances are more effective in close vicinity. Consequently, endophyte-direct seeds have significantly higher germination rate than other treatments. On the contrary, endophyte-indirect seeds showed high efficacy of germination after 48 hours, this period may have allowed enough accumulation of growth promoting substances. There is a difference in germination percentage (6.6%) between the control and endophyte-indirect treatments on Day 1, however, it is not substantial.

Expression Level of Gibberellin and Abscisic Acid Genes in Coleorhiza

Figure 47:
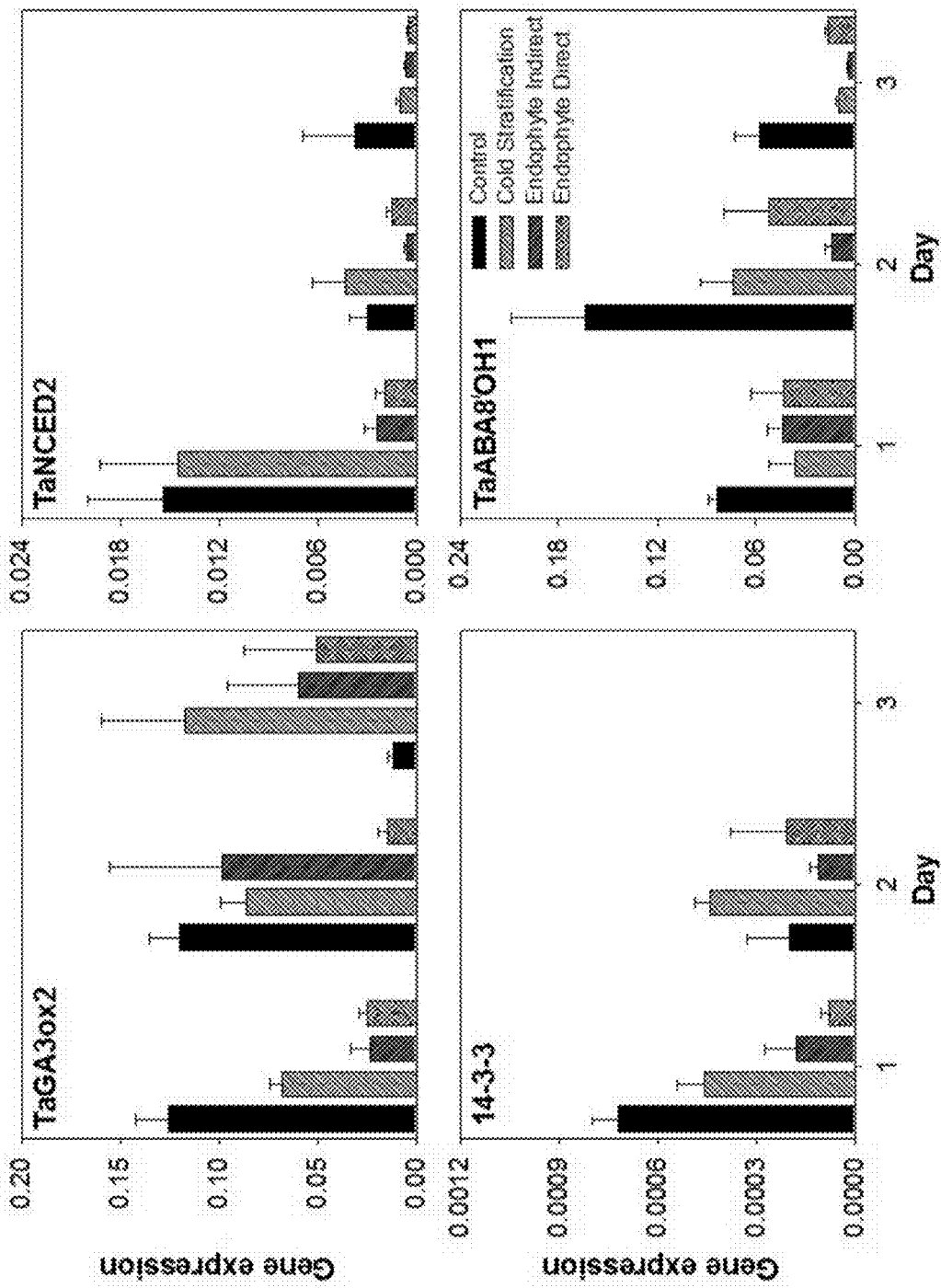
FIG. 47 shows differential expression patterns of gibberellin (TaGA3ox2 and 14-3-3) and ABA (TaNCED2 and TaABA8'OH1) genes in coleorhiza of germinating wheat seeds for three days under cold and biological stratification. Gene expression was calculated as $2^{-\Delta C_T}$.

The GA3-oxidase 2 and 14-3-3 genes were selected as GA biosynthetic gene and negative regulator of the GA biosynthesis pathway respectively [Ji et al., 2011; Zhang et al., 2007]. The NCED gene is well known for its role in ABA biosynthesis pathway whereas ABA 8'-hydroxylase gene is involved in ABA catabolic pathway [Ji et al., 2011]. Real-time quantitative PCR analysis indicated that the differential (FIG. 47) and ratio expression (FIG. 48) values of distinct functional genes varied significantly (P<0.05) among the treatments. Except for the 14-3-3 gene on Day 3, detectable expression was observed for all four genes on each day. On Day 1, all genes were down-regulated in comparison with control. Expression of GA biosynthesis gene, TaGA3ox2, was considerably higher in cold stratification treatment than that of biological stratification. On the other hand, 14-3-3 expression did not vary significantly among cold and endophyte treatments although the expression of cold stratification was slightly higher than endophytic ones. The transcript level of ABA biosynthesis gene, TaNCED2, did not vary between control and cold stratification, and was significantly up-regulated than endophytic treatments. The ABA 8'-hydroxylase gene, TaABA8'OH1, showed significant down-regulation in all three stratification treatments, with lowest expression observed under cold stratification. The expression pattern did not vary between endophyte-indirect and endophyte-direct treatments. On Day 2, TaGA3ox2 expression was significantly down-regulated in all stratification treatments than control. Expression did not vary between cold stratification and endophyte-indirect treatments, and lowest expression was detected in endophyte-direct coleorhizas. No significant difference was observed for 14-3-3 transcript level among all four treatments, although expression was somewhat higher under cold stratification. The expression of TaNCED2 gene was significantly lower in endophytic treatments than control and cold stratification. Similarly, TaABA8'OH1 gene demonstrated considerable down-regulation in stratification treatments than control. The lowest expression was detected in endophyte-indirect treatment. The transcript level of TaGA3ox2 gene also varied significantly among the treatments on Day 3. Cold stratification showed about ten times higher expression than control while two endophytic treatments did not vary significantly. Conversely, TaNCED2 and TaABA8'OH1 genes were significantly down-regulated in all stratification treatments with lowest expression in endophyte-direct and endophyte-indirect treatments respectively. No detectable expression was observed for the 14-3-3 gene on Day 3.

Figure 48:
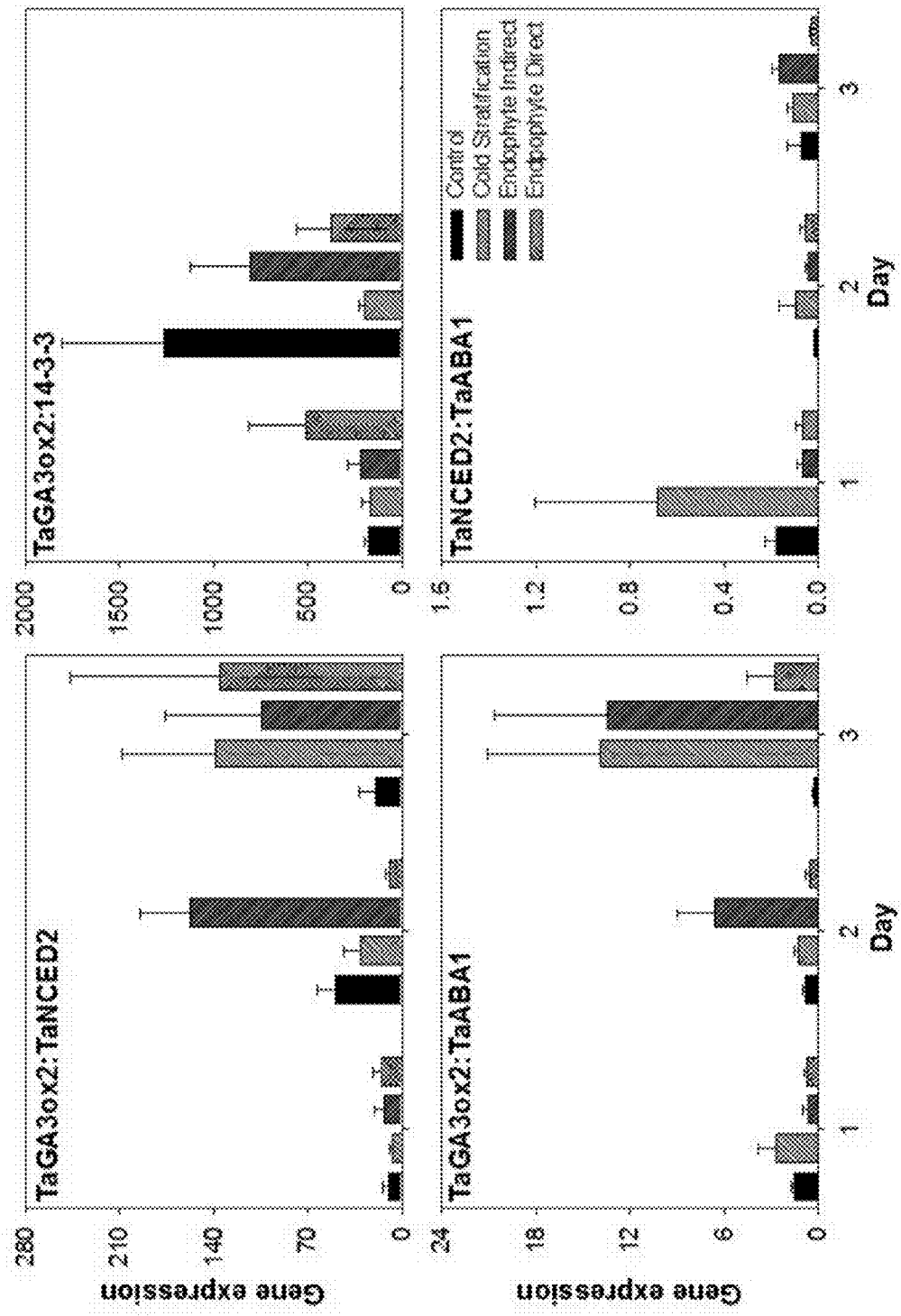
FIG. 48 shows the ratio of expression levels ($2^{-\Delta C_T}$) of gibberellin (TaGA3ox2 and 14-3-3) and ABA (TaNCED2 and TaABA8'OH1) genes in coleorhiza of germinating wheat seeds for three days under cold and biological stratification.

The ratio of GA and ABA biosynthesis gene expression, TaGA3ox2:TaNCED2, shows no considerable difference among the treatments on Day 1 but steadily increased thereafter (FIG. 48). Endophyte-indirect exhibited highest value on Day 2, which is about 5-10 times higher than the other treatments; however, all three stratification treatments demonstrated similar values on Day 3. Conversely, for the ratio of GA biosynthesis and catabolic genes (TaGA3ox2:14-3-3), endophyte-direct showed highest value on Day 1 followed by endophyte-indirect, cold stratification, and control, which is fairly similar to their germination percentage. The ratio of GA biosynthesis and ABA catabolic genes, TaGA3ox2:TaABA1, exhibited similar patterns for all treatments on Day 1, however, endophyte-indirect was considerably higher than others on Day 2. On Day 3, cold stratification and endophyte-indirect demonstrated similar expression level and control was negligible. The ratio between ABA biosynthesis and catabolic genes (TaNCED2:TaABA1) did not vary among the treatments throughout the germination period although cold stratification showed slightly higher expression level on Day 1.

Genes encoding GA and ABA biosynthesis and catabolism enzymes show differential expression patterns depending on the accumulation of transcript [Hedden and Phillips, 2000]. Expression patterns of GA3ox1 genes have been studied in plethora of plant species including *Arabidopsis* [Phillips et al., 1995], rice [Oikawa et al., 2004], and wheat [Zhang et al., 2007]. Whereas other GA biosynthesis genes such as GA-20ox are associated with growing vegetative tissues, and flowers, GA3ox (GA3ox2 or GA4H) is exclusively expressed in during seed germination and supposedly plays a crucial role [Phillips et al., 1995; Yamaguchi et al., 1998; Hedden and Phillips, 2000]. Similar to previous reports, this study also demonstrated high expression of GA3ox2 gene in wheat coleorhiza throughout the germination period. Potentially, without wishing to be bound by theory, this reflects consistent production of the bioactive GA molecule GA3 in wheat coleorhiza during germination. On the other hand, the low expression of 14-3-3 gene, a negative regulator of GA biosynthesis, was also detected in coleorhiza. With gradual seedling growth and increase in endogenous GA content, the transcript level of 14-3-3 also declined and finally diminished after Day 2. Interestingly, control had highest 14-3-3 level followed by cold stratification, endophyte-indirect, and endophyte-direct, which was somewhat reflected in their germinability. These results were in accordance with previous report by Zhang et al. [2007] who showed GA biosynthesis and catabolic genes closely linked to GA content and shoot growth.

Expression patterns of the ABA pathway genes have been studied in a wide range of cereals and pulses including rice [Oliver et al., 2007], wheat [Ji et al., 2011; Nakamura et al., 2010], bean [Qin and Zeevart, 1999]. The present results show that except control and cold stratification on Day 1, expression of TaNCED2 gene did not vary among treatments. Abscisic acid plays a pivotal role in plant stress-adaptation pathways [Nakamura et al., 2010]. Since the cold stratification seeds were kept at 4° C. for 48 hours prior to their incubation at room temperature, the abscisic acid content may have been higher. On the other hand, high TaNCED2 expression in control may have resulted in higher ABA synthesis and thereby in slower germination rate. Recent reports suggest that the catabolism of ABA mainly occurs in coleorhiza [Millar et al., 2006; Okamoto et al., 2006]. Furthermore, Barrero et al. [2009] reported up-regulation and highest expression of ABA8'OH-1 in barley coleorhiza. Similar to these reports, here high expression pattern of TaABA8'OH1 gene was found in wheat coleorhiza. The ratio of GA and ABA biosynthesis genes was fairly linked to percentage of germination. Although, TaGA3ox2:TaNCED2 did not vary remarkably on Day 1, it was highest in endophyte-indirect on Day 2 owing to its significant increase. On the other hand, all three stratification treatments showed considerable up-regulation of TaGA3ox2:TaNCED2 on Day 3, which may have reflected in their germination.

The underlying mechanisms of biological stratification are still relatively unknown but they could reveal how plant-fungus interactions take place in the early stages of germination. The role of fungal endophytes as bioenhancers is widely acknowledged [Amold et al., 2001; Hubbard et al. 2011; Saikkonen et al., 1998; Khan et al. 2012]. In this study, we demonstrated that fungal endophytes can stimulate seed germination significantly, and this mycovitality is proportional to the physical distance between the seed and fungal endophyte. Moreover, the effect of biological stratification mediated by fungal endophyte is considerably higher than cold pre-treatment. Previous studies have shown that initiation of germination is proportional to the time of cold stratification [Cavieres and Arroyo, 2000b] considering this, future study may extend cold stratification period (>48 hours) to increase seed germinability in wheat. Although, cold stratification increased the transcript level of ABA biosynthesis gene, fungal endophytes did not directly stimulate the expression of phytohormone genes in coleorhiza. However, this study specifically assessed the expression of four genes in coleorhiza.

No study has compared germination patterns under cold and biological stratification, and elucidated GA and ABA biosynthesis and catabolic gene expression in wheat coleorhiza. Coleorhiza has recently been shown as a highly active component of germinating seed [Barrero et al., 2009]. In accordance with this Example, high expression of various functional genes in coleorhiza of germinating wheat seeds was also demonstrated. Seed germinability can be substantially enhanced through the application of fungal endophytes: 1) via indirect mycovitality or without the endophyte-seed contact on tested distance (for example, the 4 cm distance was used in this Example) and 2) via direct mycovitality or once the endophyte reaches seed.

Example 13

Figure 49:
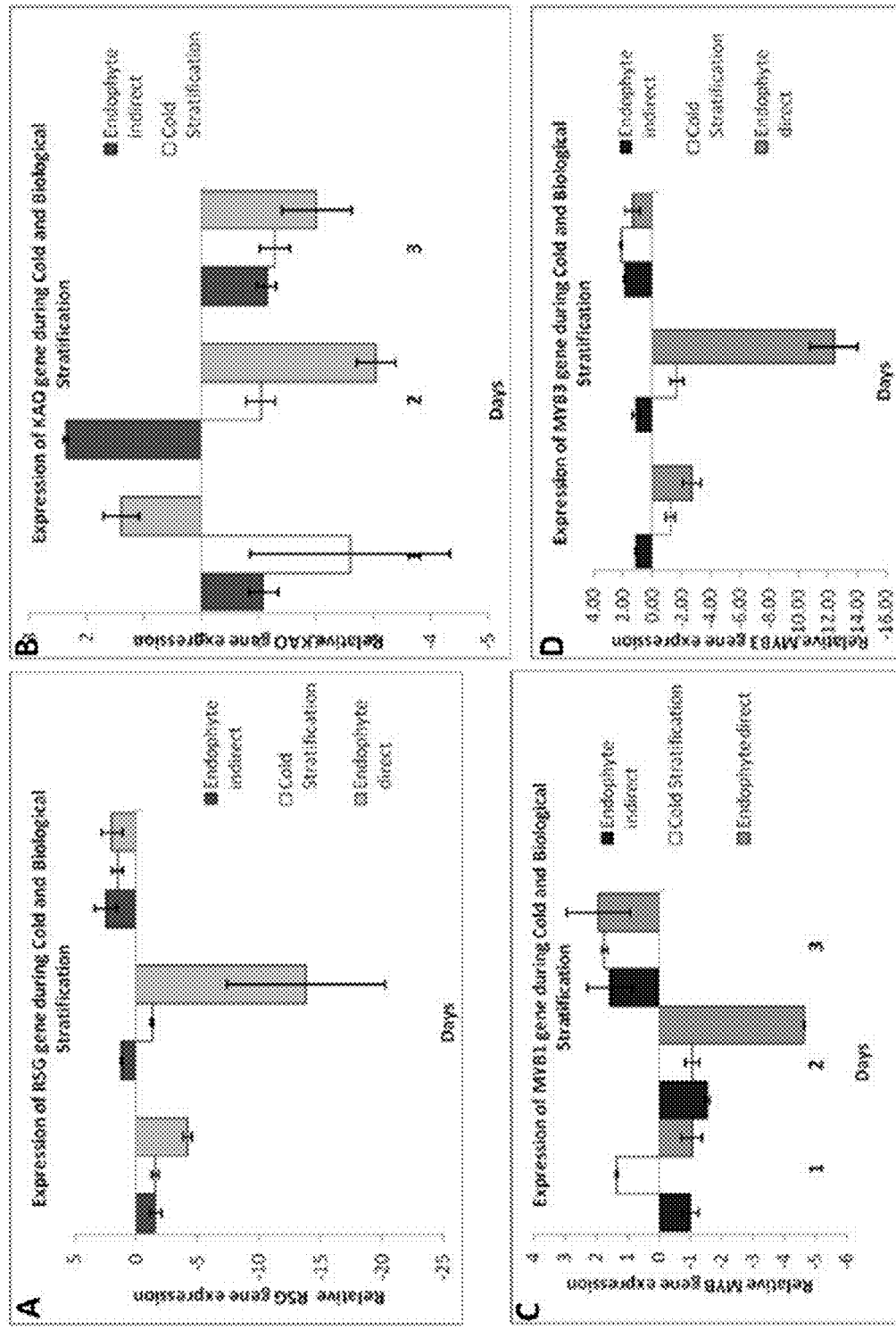
FIG. 49 shows relative expression patterns of hormonal RSG and KAO regulator genes and MYB 1 and MYB 2 resistance genes in coleorhiza of germinating wheat seeds for three days under cold and biological stratification. Gene expression was calculated as $2^{-\Delta C_T}$.
Figure 50:
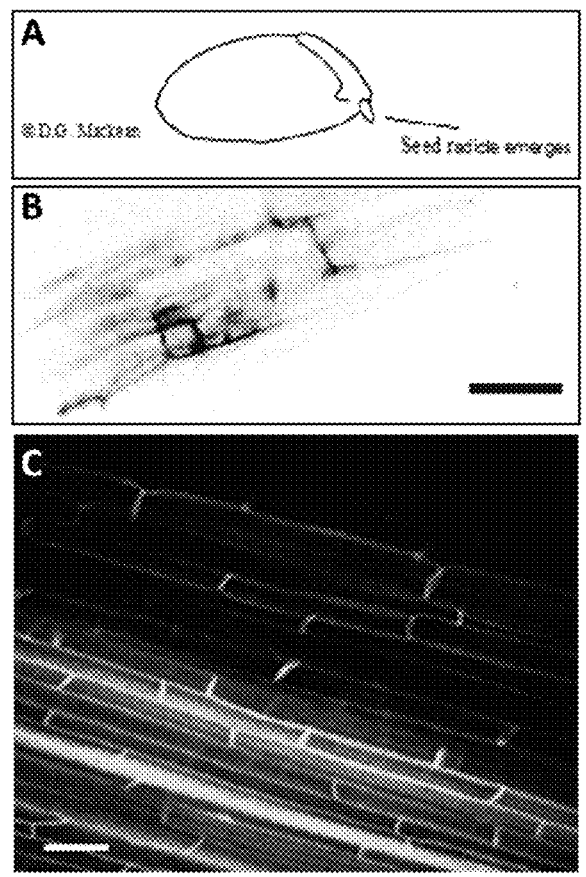
FIG. 50 shows emerging radicle from wheat geminating seed (A) Inverted fluorescence (B) and fluorescence imaging of DAF-2DA fluorescence upon reaction with NO in radicle cells (C) of AC Avonlea germinant at 5 min after treatment [Nakatsubo et al. 1998] with the fungal SMCD 2206 exudate. No fluorescence reaction observed in control radicle cells. Bar=25 μm; Bar=50 μm.

Endophytic Stratification Effects on Hormonal Regulators (RSG and KAO) and Resistance MYBs Genes Stratification is the exposure of seeds to cold and moist conditions in order to break dormancy, or enhance seed germination. As stratification is presently limited to the role of abiotic factors, this study aims to render the definition more inclusive by recognizing the role of biotic factors using mycovitality, or a seed-fungus symbiosis as a model. This acknowledges the existence of both cold and biological stratifications. Germination of wheat seeds subjected to cold stratification at 4° C. was compared to that of inoculated wheat seeds at room temperature. Seeds were inoculated with endophytic SMCD2206 strain. Changes in the seed's expression pattern of plant growth promoting genes—regulators (RSG and KAO) and phytohormonal gibberellins (GAs); and acquired resistance genes (MYBs) in abiotic vs. biotic conditions, during the early breakage of seed dormancy and germination, were assessed. Measurements were made in the coleorhiza cells using qRT-PCR (as described under Example 12). The results indicate that the RSG and KAO genes (FIG. 49), coding for enzymes promoting biosynthesis of GAs, and the MYBs resistance genes (FIG. 49) are up-regulated in inoculated seeds. Mycovitality, thus, demonstrates a reprogramming effect in pre- and post-germination events of wheat seed towards enhanced dormancy breakage and germination, effectively contributing to the prenatal care of cereal crops.

Material and Methods

RNA Samples

This study is the continuation of Example 12. The same material (wheat and SMCD 2206) and in vitro methods as well as the extracted RNA samples were used to assess phytohormone RSG and KAO regulators and resistance MYB gene expression by qRT-PCR.

Before RNA extraction started, tubes carried with coleorhiza tissues were stored in liquid nitrogen immediately as soon as coleorhiza tissues were isolated to preserve the cells and prevent denaturation of RNA. Aurum™ Total RNA Mini Kit (Bio-Rad Laboratories) was used in total RNA extraction from plant tissues, and it suggested a minimum 20 mg of plant tissues were suitable for each sample. The extraction steps were done rapidly and the entire process was kept either in ice, as $RNA_s$ were easily denatured at room temperature. Fresh extracted total $RNA_s$ were directly loaded with premixed cDNA synthesis agents obtained from iScript cDNA Synthesis Kit (Bio-Rad Laboratories). Reverse transcription was carried out at 42° C. for 30 minutes with a final denaturation at 85° C. for 5 minutes in a Thermo cycler. cDNA concentration was measured by Nanodrop spectroscopy (Thermo Scientific) and diluted or concentrated to 100 ng/μl.

Quantitative RT-PCR and Statistical Analysis

The quantitative real-time PCR (QRT-PCR) was performed on a MiniOpticon™ Real-Time PCR Detection System (Bio-Rad Laboratories) with iQ™ SYBR® Green supermix kit (Bio-Rad Laboratories). In order to normalize QRT-PCR data, actin gene (131 bp length fragment) was selected as a reference gene and served as internal control to avoid fluctuation bias of gene expression under low cDNA concentration [Zhang et al. 2007; Nicot 2005]. KAO and RSG gene's primer according to Zhang et al. [2007] were tested in this experiment, whereas original primers were designed for MYB1 and MYB2 based on Triticum aestivum sequences publicly available (compbio.dfci.harvard.edu/cgi-bin/tgi/geneprod_search.pl) in Computational Biology and Functional Genomics Laboratory (Harvard University). The MBY newly designed primers (Table 9):

Transcription factor Myb2 mRNA (158 bp) which comprises the sequences as shown in SEQ ID NO:16 and SEQ ID NO:17 and transcription factor Myb1 mRNA (152 bp) which comprises the sequences as shown in SEQ ID NO:18 and SEQ ID NO: 19 (Table 9).

100 ng/μl cDNA samples were further diluted to 10 ng/μl and 2 μl cDNA were used for each 25 μl reaction. In addition, 12.5 μl of iQ™ SYBR® Green supermix, 8.5 μl sterile milli-Q water, 1 μl of each forward and reverse primer (10 pmol) were made up to 25 μl reaction mix. The protocol of thermo-cycle was suggested as 95° C. for 10 minutes and 40 cycles of 94° C. for 20 s, 60° C. for 30 s, and 72° C. for 1 min. All the cDNA samples from the treatments were carried out in three replicates and two negative controls in QRT-PCR. The gene expression levels referred to quantitative curves were carried out by CFX Manager Software (Bio-Rad Laboratories). Cycle quantification (Cq) value from the recorded fluorescence measurements were adjusted manually with baseline. Relative quantitation is the statistical method chosen in this study [Gizinger 2002]. Gene of interest relative to the endogenous control gene was used to compare with different treatments. The quantification (ΔCT) was done relative to the subtraction from Cq value of the gene of interest to Cq value of the control gene. ΔCT was further subtracted by calibrator value and generated corresponding ΔΔCT values which were transformed to log 2 (doubling function of PCR) to synthesize relative gene expression levels [Jurado et al., 2010]. Amplified, RSG, KAO and MYB genes were purified by using BioBasic PCR Purification Kit (Bio Basic Inc.) and sent for sequence job at Plant Biotechnology Institute (NRC-PBI). Gene sequences were identified by Basic Local Alignment Search Tool (BLAST) analyses (http://blast.ncbi.nlm.nih.gov). High identity or similar genes corresponding to different homologous organisms were assembled and aligned by software MEGA5 (Molecular Evolutionary Genetics Analysis). A phylogeny tree was made with the statistical method of Neighbor-joining based on the aligned genes.

Example 14

Nitric Oxide (NO) Showed the Regulatory Effect on Mycovitalism During Early Seed Germination Events Nitric oxide (NO) is a highly reactive signal molecule common to fungal, animal and plant systems. NO is also known as a signaling molecule involved in eukaryotic cell hormonal signaling [Guo et al. 2003] and plant response to abiotic and biotic stresses [Hayat et al. 2010]. While there is evidence for NO accumulation, increased activation of SOD and proline contributing to the delay of $O^{2-}$ and $H_2O_2$ accumulation in wheat leaves under salt stress, almost no information exists for fungal endophytes and there interaction with seed germination (mycovitalism). Here, the occurrence of NO in the early stages of germinating wheat AC Avonlea seeds was investigated for three days—endophyte SMCD 2206 on PDA, focusing on the radicle response to fungal diffusible molecules. NO was visualized in radicle (early root organ) in culture germinants by fluorescence microscopy using the specific probe 4,5-diaminofluoresce in diacetate; the assessment was conducted after five-minute of exposition to the fungal exudate, as sufficient to induce significant NO accumulation [Calcagno et al. 2012]. Since, SMCD 2206 exudate induced a significant production of NO in the wheat's root tissues; without wishing to be bound by theory, it is possible that this production is regulated by a molecular dialogue occurring in the wheat symbiosis.

Material and Methods

The accumulation of NO in radicle tissues was analyzed in wheat AC Avonlea germinating seed (in vitro approach presented under Example 12) using the cell permeable NO-specific probe DAF-2DA according to Calcagno et al. [2012] which is converted into its fluorescent triazole derivate DAF-2T upon reaction with NO. The formation of DAF-2T was visualized by fluorescence (Carl Zeiss Axioscop 2) microscopy. AC Avonlea germinant was assessed at 5 min after treatment with the fungal SMCD 2206 exudate following procedure proposed by Nakatsubo et al. [1998]

The specificity of this response to endophytic SMCD 2206 was confirmed by the lack of response in the non-inoculated radical cells. The analyses were repeated in three independent biological replicates.

Results and Discussion

Seed treatment with the fungal exudate can mimic—to some extent—the approach of endophytic hyphae during the presymbiotic phase of the interaction, as suggested for AM mycorrhiza in co-culture with *Arabidopsis* roots [Calcagno et al. 2010]. The fungal exudate could, therefore, be confidently used to test whether diffusible fungal signals elicit NO accumulation in the host wheat tissues (FIG. 51) during the early germination events enhancing mycovitality.

Figure 51:
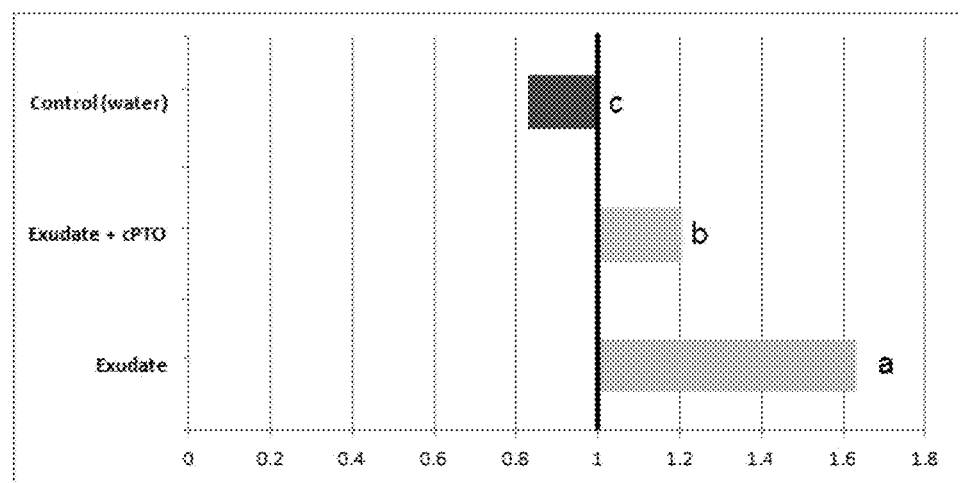
FIG. 51 shows DAF-2T fluorescence intensity values at 5 min after treatment of wheat radicle from AC Avonlea germinants with the SMCD 2206 fungal exudate, fungal exudate together with the NO scavenger cPTIO, and sterile water. Radicle segments were incubated for 30 min in 2 ml of detection buffer (10 mM Tris-Hd, pH 7.4, 10 mM KCl) containing 15 μM DAF -2DA (Sigma-Aldrich) with or without 1 mM 2-(4-carboxyphenyl)-4,4,5,5-tetramethylimidazoline-1-oxyl-3-oxide (cPTIO) as an NO scavenger. Average fluorescence values are reported as a ratio of the fluorescence intensity at 5 min to the fluorescence intensity at time 0. Different letters indicate statistically significant differences between samples (p<0.05, Kruskal-Wallis test).

Cellular evidence, therefore, suggests that NO accumulation is a novel component in the signaling pathway that leads to mycosymbiosis related with mycovitalism of wheat seed (FIG. 51). This finding has both theoretical and practical values in attempts to improve plant prenatal-care using endophytic symbionts.

Example 15

Study of the Effects of Endophytes on Phytoremediation and Phytoreclamation

Phytoremediation is a promising environmental technique. It has been shown to be cost-effective for reclamation of hydrocarbon/petroleum, salt, heavy metal and radioisotope-contaminated soils. In this study, the effects of coniferous (*Picea* or *Pinus*) and deciduous (*Salix* or *Populus*) trees, shrubs (*Caragana* or *Krascheninnikovia*), and grasses (*Festuca* or *Elymus*) infected (E+) and non-infected (E−) by endophytic organisms (via plant propagation material, seed or root infection and colonization) (SMCD 2204, 2206, 2208, 2210 and 2215) on the decomposition, transformation or degradation of petroleum hydrocarbons in petroleum contaminated soil will be investigated. Plants will be grown in pots containing petroleum contaminated and non-contaminated soils. Plants will be inoculated and incubated for 6 months using the greenhouse method suggested by Soleimani et al. (2010). Unplanted pots will be used as control. At the end of the experiment, plant-root colonization (Abdellatif et al. 2009), soil hydrophobicity (Chau 2012), total petroleum hydrocarbons (TPHs), and polycyclic aromatic hydrocarbons (PAHs) contents will be analysed (Germida et al. 2010). The difference in E+vs. E− plants root and shoot biomass and leaf photosynthesis will be compared (Hubbard et al. 2012) with PAH and TPH removal in the rhizosphere of the plants. Unplanted pots will be used as control to calculate the efficacy of symbiotic (E+) plants on degradation of petroleum hydrocarbons (Soleimani et al. 2010). The infected plants will decompose, transform or degrade hydrocarbons and salts, uptake and accumulate and dean up or eliminate the heavy metals and radioisotopes in the contaminated site, soil or environment.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

2204 ITS rDNA
CCTATAGCTGACTGCGGAGGGACATTACAAGTGACCCCGGTCTAACCAC
CGGGATGTTCATAACCCTTTGTTGTCCGACTCTGTTGCCTCCGGGGCGA
CCCTGCCTTCGGGCGGGGGCTCCGGGTGGACACTTCAAACTCTTGCGTA
ACTTTGCAGTCTGAGTAAACTTAATTAATAAATTAAAACTTTTAACAACG
GATCTCTTGGTTCTGGCATCGATGAAGAACGCAGCGAAATGCGATAAGT
AATGTGAATTGCAGAATTCAGTGAATCATCGAATCTTTGAACGCACATTG
CGCCCCCTGGTATTCCGGGGGGCATGCCTGTTCGAGCGTCATTTCACCA
CTCAAGCCTCGCTTGGTATTGGGCAACGCGGTCCGCCGCGTGCCTCAA
ATCGACCGGCTGGGTCTTCTGTCCCCTAAGCGTTGTGGAAACTATTCGC
TAAAGGGTGTTCGGGAGGCTACGCCGTAAAACAACCCCATTTCTAAGGT
TGACCTCGGATCAGGTAGGGATACCCGCTGAACTTAAGCATATCAATAA
GCGGAGGAAAAGAAACCAACAGGGATTGCCCCAGTAACGAA
(SEQ ID NO: 1)

>2204F ITS rDNA
TCGATCTAGCTCATAGTGACTGCGGAGGGACATTACAAGTGACCCCGGT
CTAACCACCGGGATGTTCATAACCCTTTGTTGTCCGACTCTGTTGCCTCC
GGGGCGACCCTGCCTTCGGGCGGGGCTCCGGGTGGACACTTCAAACT
CTTGCGTAACTTTGCAGTCTGAGTAAACTTAATTAATAAATTAAAACTTT
TAACAACGGATCTCTTGGTTCTGGCATCGATGAAGAACGCAGCGAAATGC
GATAAGTAATGTGAATTGCAGAATTCAGTGAATCATCGAATCTTTGAACG
CACATTGCGCCCCCTGGTATTCCGGGGGGCATGCCTGTTCGAGCGTCAT
TTCACCACTCAAGCCTCGCTTGGTATTGGGAAACGCGGACCGACGCGTG
CCTCAAATCGACCGGCAGGGTCTTCTGTCCCCTAAACGTTGTGAAAATTA
TTCGATAAAGGATGTTCCGTGCTACATTGTGAATAGAACCGCATTTATAA
CATTGATTATAAACTAATTACGACTACATGGTAAGATAGATATATCAAGG
AACTTCCTCTAAATGACCAAGAAACC (SEQ ID NO: 2)

TABLE 1-continued

>2206 ITS rDNA
TCGACGGCGTATCCTAGTGACTGCGGAGGATCATTACCGAGTGAGGGC
CCTCTGGGTCCAACCTCCCACCCGTGTTTAATTTACCTTGTTGCTTCGGC
GGGCCCGCCTTAACTGGCCGCCGGGGGGCTTACGCCCCCGGGCCCGC
GCCCGCCGAAGACACCCTCGAACTCTGTCTGAAGATTGTAGTCTGAGTG
AAAATATAAATTATTTAAAACTTTCAACAACGGATCTCTTGGTTCCGGCA
TCGATGAAGAACGCAGCGAAATGCGATACGTAATGTGAATTGCAAATTCA
GTGAATCATCGAGTCTTTGAACGCACATTGCGCCCCTGGTATTCCGGG
GGGCATGCCTGTCCGAGCGTCATTGCTGCCCTCAAGCACGGCTTGTGT
GTTGGGCCCCGTCCTCCGATCCCGGGGACGGGCCCGAAAGGCAGCG
GCGGCACCGCGTCCGGTCCTCGAGCGTATGGGGCTTTGTCACCCGCTC
TGTAGGCCCGGCCGGCGCTTGCCGATCAACCCAAATTTTTATCCAGGTT
GACCTCGGATCAGGTAGGGATACCCGCTGAACTTAAGCATATCAATAAG
CGGAGGAA (SEQ ID NO: 3)

>2208 ITS rDNA
TAACTGATTTGGCGGACTGGCGGAAGGACATTAAAGAGACGTTGCCCTT
CGGGGTATACCTCCCACCCTTTGTTTACCTTTTCCTTTGTTGCTTTGGCG
GGCCCGTCCTCGGACCACCGGTTTCGGCTGGTCAGTGCCCGCCAGAGG
ACCTAAAACTCTGTTTGTTCATATTGTCTGAGTACTATATAATAGTTAAA
ACTTTCAACAACGGATCTCTTGGTTCTGGCATCGATGAAGAACGCAGCGA
AATGCGATAAGTAATGTGAATTGCAGAATTCAGTGAATCATCGAATCTTT
GAACGCACATTGCGCCCCTGGTATTCCGGGGGGCATGCCTGTTCGAG
CGTCATTACAACCCTCAAGCTCTGCTTGGTATTGGGCTCTGCCGGTCC
GGCAGGCCTTAAAATCATTGGCGGTGCCATTCGGCTTCAAGCGTAGTAA
TTCTTCTCGCTTTGGAGACCCGGGTGCGTGCTTGCCATCAACCCCCAAT
TTTTTCAGGTTGACCTCGGATCAGGTAGGGATACCCGCTGAACTTAAGC
ATATCAATAAGCGGAGGAAAAGAAACCAACAGGGATTGTCCCAATAACG
AATTTATAAATAATA (SEQ ID NO: 4)

>2210 ITS rDNA
TCGAGAGTTCGGACTAAGTGCCTGATCCGAGGTCAAGACGGTAATGTTG
CTTCGTGGACGCGGGCCACGCCCCCCCGCAGACGCAATTGTGCTGCGC
GAGAGGAGGCAAGGACCGCTGCCAATGAATTTGGGGCGAGTCCGCGCG
CGAAGGCGGGACAGACGCCCAACACCAAGCAGAGCTTGAGGGTGTAGA
TGACGCTCGAACAGGCATGCCCCATGGAATACCAAGGGGCGCAATGTG
CGTTCAAAGATTCGATGATTCACTGAATTCTGCAATTCACACTACTTATC
GCATTTCGCTGCGTTCTTCATCGATGCCAGAGCCAAGAGATCCATTGTTG
AAAGTTGTAACGATTGTTTGTATCAGAACAGGTAATGCTAGATGCAAAAA
AGGTTTTGTTAAGTTCCAGCGGCAGGTTGCCCCGCCGAAGGAGAACGAAA
GGTGCTCGTAAAAAAAGGATGCAGGAATGCGGCGCGTGAGGGTGTTAC

CCCTACCACCCGGGAGAGAACCCCCGAGGGCCGCGACCGCACCTGGTT
GAGATGGATAATGATCCTTCCGCAGGTTCACCTACGGAAACC
(SEQ ID NO: 5)

>2215 16S rDNA
CCGGGGGCACTCCACTGCGTATGTGTGACGAGTAGACCGCTGCGCTTA
GCTGAGGTCTGATGAAATGTAGAACACTTAACAAAAATATGCCCGGATG
GATATACTTTTCAACGACAGGGCTGCGATTGGATGATCTCCTTTGAAACA
CAGAACTAGTCACGGCGACGAATACTCAACTTCGACCCCCCCCCTTTCT
GGAGGCGCGTCTTAGTCCCCTCCTTGATGGAGCTGCCCCGTGCTCGGC
GGCCGGAGTCGGCGGTGTTTTCCGCTGTACCTGAGACGCTGGACCAAC
TCCTTCGGGAGGCAGCAGTGGGGAATATTGCACAATGGGCGCAAGCCT
GATGCAGCGACGCCGCGTGAGGGATGACGGCCTTCGGGTTGTAAACCT
CTTTCAGCAGGGAAGAAGCGCAAGTGACGGTACCTGCAGAAGAAGCGC
CGGCTAACTACGTGCCAGCAGCCGCGGTAATACGTAGGGCGCAAGCGT
TGTCCGGAATTATTGGGCGTAAAGAGCTCGTAGGCGGCTTGTCACGTCG
ATTGTGAAAGCCCGAGGCTTAACCTCGGGTCTGCAGTCGATACGGGCAG
GCTAGAGTGTGGTAGGGGAGATCGGAATTCCTGGTGTAGCGGTGAAAT
GCGCAGATATCAGGAGGAACACCGGTGGCGAAGGCGGATCTCTGGGCC
ATTACTGACGCTGAGGAGCGAAAGCGTGGGGAGCGAACAGGATTAGAT
ACCCTGGTAGTCCACGCCGTAAACGGTGGGAACTAGGTGTTGGCGACAT
TCCACGTCGTCGGTGCCGCAGCTAACGCATTAAGTTCCCCGCCTGGGG
AGTACGGCCGCAAGGCTAAAACTCAAAGGAATTGACGGGGGCCCGCAC
AAGCGGCGGAGCATGTGGCTTAATTCGACGCAACGCGAAGAACCTTACC
AAGGCTTGACATACACCGGAAACATCCAGAGATGGGTGCCCCCTTGTGG
TCGGCGTACAGGTCGTGCATGGCTGTCGTCAGCTCGTGTCGTGAGATGT
TGGGTAAGTCCCGCAACGAGCGCAACCTTGTTCTGGTGCTGCCAGCATG
CCCTTCGGGTGATGGGACTTCACCACGGAGACCGCGGCTCCACTCCGA
CGAGGTGGGGGACGACGTCAGTCATCATGCCCTAATGTCTGGCTG
(SEQ ID NO: 6)

TABLE 2

SMCD endophytic root colonization frequency assessed in 3D wheat germinant radicles.

| Endophytes | SMCD2204 | SMCD2206 | SMCD2210 | SMCD2215 |
|---|---|---|---|---|
| % colonization | 43 | 40 | 49 | 48 |

TABLE 3

Energy of germination (EG) and hydrothermal time (HTT) of wheat seeds grown under heat (36° C.), drought (potato dextrose agar (PDA) media plus 8% polyethylene glycol (PEG) 8000), heat and drought combined and control in vitro conditions. Within a column, data followed by an asterisk (*) are significantly different from the no endophyte control ($p \leq 0.05$; ANOVA, followed by a post-hoc LSD test).

| | Heat | | Drought | | Heat and Drought | | Control | |
|---|---|---|---|---|---|---|---|---|
| Endophyte | EG (days) | HTT to 50% germination (MPa ° C. days) | EG (days) | HTT to 50% germination (MPa ° C. days) | EG (days) | HTT to 50% germination (MPa ° C. days) | EG (days) | HTT to 50% germination (MPa ° C. days) |
| SMCD 2204 | 3.7 ± 0.3 | 91 ± 7 | 2.9 ± 0.3 | 52 ± 5' | 2.0 ± 0.8 | 22 ± 8 | 1.6 ± 0.2 | 65 ± 8 |
| SMCD 2206 | 2.5 ± 0.3 | 62 ± 7 | 1.9 ± 0.1* | 34 ± 2* | 2.0 ± 0.8 | 22 ± 8 | 1.5 ± 0.2 | 61 ± 8 |
| SMCD 2208 | 3.7 ± 0.3 | 91 ± 7 | 3.0 ± 0.3 | 53 ± 5 | 4.0 ± 1.0 | 43 ± 10 | 1.6 ± 0.2 | 65 ± 8 |
| SMCD 2210 | 1.8 ± 0.2* | 44 ± 5* | 2.2 ± 0.2* | 39 ± 3* | 1.0 ± 0.5 | 11 ± 5 | 1.6 ± 0.2 | 65 ± 8 |
| SMCD 2215 | 2.5 ± 0.3 | 62 ± 7 | 2.3 ± 0.2* | 41 ± 3* | 1.3 ± 0.2 | 14 ± 2 | 1.5 ± 0.2 | 61 ± 8 |
| No Endo | 3.8 ± 0.5 | 94 ± 11 | 4.5 ± 0.5 | 80 ± 8 | 3.0 ± 1.5 | 32 ± 15 | 1.6 ± 0.2 | 65 ± 8 |

Note:
The seeds used in EG and HTT determination were from the second round of experiments, and hence subjected to sterilization in 5% sodium hypochlorite for one minute, rather than three;
SMCD—Saskatchewan Microbial Collection and Database

TABLE 4

Endophytes increase drought tolerance efficiency (DTE) and yield in barley and wheat under stress conditions.

| Crop | Genotypes | DTE‡ (%) | Control conditions Average YIELD spikes g (3plants/pot) | | | Drought Stress Average YIELD spikes g (3plants/pot) | | |
|---|---|---|---|---|---|---|---|---|
| | | | E − | E + | Increased % | E − | E + | Increased % |
| WHEAT | AC Avonlea (Cont) | 16.1 | 18.27 | 25.52 | 28.41 | 2.94 | 10.62 | 72.32 |
| | PT 580 Control | 57.3 | 23.42 | 32.60 | 28.16 | 13.38 | 21.53 | 37.85 |
| | CDC Utmost VB | 72.3 | 20.55 | 35.4 | 41.95 | 16.67 | 29.8 | 44.06 |
| | Strongfield | 75.6 | 13.54 | 16.77* | 19.26 | 10.23 | 14.98 | 31.71 |
| | Unity VB | 75.3 | 20.72 | 26.6 | 22.11 | 15.61 | 23.2 | 32.72 |
| | CDC Teal | 76.9 | 19.51 | 30.37 | 35.76 | 14.90 | 25.1 | 40.64 |
| | Carberry | 83.8 | 17.31 | 33.07 | 47.66 | 14.52 | 22.9 | 36.59 |
| | BW 423 | 85.0 | 13.26 | 25.83 | 48.66 | 12.28 | 21.41 | 42.64 |
| | CDC Veronna | 87.8 | 15.35 | 22.58 | 32.02 | 13.49 | 20.16 | 33.09 |
| | Lillian | 87.8 | 20.50 | 28.3 | 27.56 | 18.1 | 23.6 | 23.31 |
| Two row barley | | | | | | | | |
| BARLEY | CDC Copeland | 4.9 | 6.01 | 10.78 | 44.25 | 2.91 | 6.95 | 58.13 |
| | CDC Kendall | 13.2 | 9.93 | 24.19 | 58.95 | 0.32 | 1.03 | 68.93 |
| | AC Metcalfe | 43.2 | 16.5 | 22.4* | 26.34 | 7.3 | 14.05 | 48.04 |
| | New Dale | 72.1 | 9.55 | 26.88 | 64.47 | 6.89 | 12.17 | 43.39 |
| Six row barley | | | | | | | | |
| | Legacy | 1.1 | 20.42 | 26.87* | 24.00 | 2.26. | 2.38* | 5.04 |
| | CDC Bold | 57.0 | 9.16 | 19.9 | 53.97 | 5.22 | 7.5 | 30.40 |

‡Drought tolerance efficiency (DTE) = (Yield under stress/Yield under non-stress) × 100, presented in increasing order within the Table. Genotypes with high DTE are considered as drought resistant; whereas genotypes with low DTE are considered as drought susceptible. Note: Effect of the endophyte's absence (E−) or presence (E+) on genotype yield was calculated as an average of all three tested SMCD 2206, SMCD 2210, and SMCD 2215 strains.
*Within the rows, a mean is not statistically significant at $p \geq 0.05$.

TABLE 5

Rhizobium sequence maximum identity against GenBank database

| Accession | Description | Max score | Total score | Query coverage | E value | Max ident |
|---|---|---|---|---|---|---|
| EF549401.1 | Rhizobium sp. CCBAU 83431 16S ribosomal DNA gene, partial sequence | 1007 | 1007 | 46% | 0.0 | 99% |

Native Rhizobium nodulator in interaction with Streptomyces SMCD2215 16S F (Golden)
Rhizobium sp.
GGAAGGGGGCGGCTTACCATGCAAGTCGAGCGCCCCGCAAGGGG
AGCGGCAGACGGGTGAGTAACGCGTGGGAATCTACCCTTGACTACG
GAATAACGCAGGGAAACTTGTGCTAATACCGTATGTGTCCTTCGGGA
GAAAGATTTATCGGTCAAGGATGAGCCCGCGTTGGATTAGCTAGTTG
GTGGGGTAAAGGCCTACCAAGGCGACGATCCATAGCTGGTCTGAGA
GGATGATCAGCCACATTGGGACTGAGACACGGCCCAAACTCCTACG
GGAGGCAGCAGTGGGGAATATTGGACAATGGGCGCAAGCCTGATCC
AGCCATGCCGCGTGAGTGATGAAGGCCCTAGGGTTGTAAAGCTCTTT
CACCGGAGAAGATAATGACGGTATCCGGAGAAGAAGCCCCGGCTAA
CTTCGTGCCAGCAGCCGCGGTAATACGAAGGGGGCTAGCGTTGTTC
GGAATTACTGGGCCGTAAAGCGCACGTAGGCGGATCGATCAGTCAGG
GGTGAAATCCCAGGGCTCAACCCTGGAACTGTCTTTGATACTGTCGA
TCTGGAGAACTTCCTGCTCGAGTGATTTACCCACATGGCGAGCACCG
GCACCCCGTTTCGACATGCAAAAAATGATGCCCAGGCTTATGTTTGA
CCTGGCTGCTACGGCTCTCTTCGGCGTGGACCCCGGCCTCCTATCC
CCGGAGATGCCACCCATGGACGCCGCAGTCTCCATGGATATATCATG
GAGGTGGGTTTTCTCCGACTCATGATGCCGGCTTCTTGCTGGAAGTT
GATGAAGCAACTAAACATCAGCCCTGAGAGAAAGCTTCGCATGCCGC
GCAGGGTGCTCCGAGTGTTCGTCTGGAGATGATGAAATAGACGAAGA
TCATCTCATGTCATGTTGGTAACGACGAGAACAAGATGGTGTGGATTT
TGTGTCTTCCATCCTCCATGACCCTGACGATGCTGATGATGACGTGG
TTCATGCTATGATGACTCGATACTGGTCGCTGCAAGCGGATACAGTT
GGGACCTACCGCTAACATGGTTCTTTCTACAACCTCCCCCCAAACCG
CATAGGATCGTGGTCAATCATTCGGCACGAACCTCTTCCCCCATTGC
CTCCAACTAGTTTATCGCTCTAGAGTTGGGGAGCCCTGTGTGACCTT
TCGTACGCGA (SEQ ID NO: 7)

TABLE 6

Set of SOD, MnSOD and Pro primers used to assess pea [Handel] genes expression exposed to PEG drought/osmotic stress by qPCR

| Gene Name | Primer | Reference |
|---|---|---|
| PP2A internal control | CCACATTACCTGTATCGGAT GACA (F) (SEQ ID NO: 8) GAGCCCAGAACAGGAGCTA ACA (R) (SEQ ID NO: 9) | Die et.al, Planta (2010) 232: 145-153 |
| MnSOD salt and drought | gcagaaaaaccctatcctccgtgct (F) (SEQ ID NO: 10) gctccaaagctccgtagtcg (R) (SEQ ID NO: 11) | Wong Vega et.al., Plant Mol. Biol. 17 (6), 1271-1274 (1991) |
| Pea SOD | ctgtactcgctgttggggtg (F) (SEQ ID NO: 12) gcatggatatggaagccgtg (R) (SEQ ID NO: 13) | Nakamura et.al., Plant Biotechnol. 20, 247-253 (2003) |
| Proline (Pro) | aatggccgaaagcattgcca (F) (SEQ ID NO: 14) aaggacggtgatgccgatggactc (R) (SEQ ID NO: 15) | Williamson, C.L. and Slocum, R.D., Plant Physiol. 100, 1464-1470 (1992) |

TABLE 7

Evaluation of the efficiency of seed sterilization methods. Seeds were germinated on potato dextrose agar for 4 days at ambient temperature (20° C.). Each petri dish had 10 wheat seeds.

| Sterilization type | Potato dextrose agar (PDA) | |
|---|---|---|
| | Contamination | Germination |
| Control | 50% | 80% |
| 50% Bleach | 0 | 50% |
| 95% Ethyl alcohol | 0 | 70% |
| 50% Bleach + 95% Ethyl alcohol | 0 | 50% |
| Chlorine gas | 0 | 80% |

TABLE 8

Average germination of wheat seeds under cold and biological stratification treatments

| Day | Control | Cold Stratification | Endophyte-indirect | Endophyte direct |
|---|---|---|---|---|
| 1 | 6.66 ± 6.66$^{ab}$ | 16.6 ± 3.33$^{ab}$ | 0.00 ± 0.00$^{a}$ | 26.6 ± 12.02$^{b}$ |
| 2 | 16.6 ± 8.81$^{p}$ | 40.0 ± 11.5$^{pq}$ | 50.0 ± 5.77$^{q}$ | 66.6 ± 8.81$^{q}$ |
| 3 | 33.3 ± 12.01$^{x}$ | 53.3 ± 8.81$^{xy}$ | 73.3 ± 3.33$^{yz}$ | 86.9 ± 7.24$^{z}$ |

* Duncan test was performed to test significant difference among the treatments (Control, Cold Stratification, Endophyte-indirect, and Endophyte direct) on Day 1 (a, b, c), Day 2 (p, q), and Day 3 (x, y, z)
** Different letters indicate significant difference at $P < 0.05$

TABLE 9

| Transcription factor Myb2 mRNA (158 bp) | | |
|---|---|---|
| TaMyb2 1F | acatcaagcgcggcaacttca | (SEQ ID NO: 16) |
| TaMyb2 1R | gagccgcttcttgaggtgggtgt | (SEQ ID NO: 17) |
| Transcription factor Myb1 mRNA (152 bp) | | |
| TaMyb1 1F | ccagggaggacggacaacga | (SEQ ID NO: 18) |
| TaMyb1 1R | ctctgcgccgtctcgaagga | (SEQ ID NO: 19) |

REFERENCES

Abdellatif et al. 2009. Mycological Research, 113:782-791.
Abdellatif et al. 2010. Can J Plant Pathol, 32: 468-480.
Adriaensen et al. 2006. Mycorrhiza, 16: 553-558.
Agius et al. 2006. PNAS, 103: 11796-11801.
Ali et al. 1994. Annals of Applied Biology, 125: 367-375.
Allen 1958. Forest Chron, 34: 266-298.
Armas et al. 2004. Ecology, 85: 2682-2686.
Arnold et al. 2001. Mycological Research, 105: 1502-1507.
Bacon and White 2000. In: Bacon C W and White J F J (Eds), *Microbial endophytes*. Marcel Dekker Inc; New York, N.Y., USA. 237-263.
Bae et al. 2009. J Exp Bot 60: 3279-3295.
Baird et al. 2010. Mycorrhiza. 20: 541-549.
Barrero et al. 2009. Plant Physiology, 150: 1006-1021.
Baskin et al. 1992. International Journal of Plant Sciences, 153: 239-243.
Baskin and Baskin 2004. Sci. Res., 14: 1-16.
Bewley and Black 1982. Physiology and Biochemistry of Seeds. 2. Viability, Dormancy, and Environmental Control. Springer-Verlag, Berlin.
Bloom and Richard 2002. ASAE Paper No 027010. ASAE, St. Joseph, Mich.
Bogatek and Lewak 1988. Physiologia Plantarum, 73: 406-411.
Boyko and Kovalchuk 2008. Environmental and Molecular Mutagenesis, 49: 61-72.
Bradford 2002. In: J. Kigel J, Galili G (eds), *Seed Develop and Germin*. Marcel Dekker Inc, New York, pp. 351-396.
Calcagno et al. 2012. Mycorrhiza, 22:259-69.
Cao and Moss. 1989. Crop Sci, 29: 1018-1021.
Carpita et al. 1983. Physiologia Plantarum 59: 601-606.
Cavieres and Arroyo, 2000. Plant Ecology 149: 1-8.
Cavieres and Arroyo, 2000b. Gayana Botanica 64: 40-45.
Chariton et. al. 2008. Metabolomics, 4: 312-327.
Chau et al. 2012. Fungal Biology, 116:1212-1218.
Chipanshi et al. 2006. Clim Res, 30: 175-187.
Choi and Sano, 2007. Molecular Genetics and Genomics, 277: 589-600.
Davitt et al. 2010. New Phytol, 188: 824-834.
de Bary 1866. Vol. II. Hofmeister's Handbook of Physiological Botany. Leipzig, Germany.
Desfeux et al., 2000. Plant Physiology, 123: 895-904.
Dong-dong et al. 2009. J Zhejiang Univ-Sci B, 9: 964-968.

Farquhar and Richards 1984. Australian Journal Plant Physiology 11: 539-552.
Farquhar et al. 1989 In: Jones H G, Flowers T J and Jones M B (Eds) Plants under stress. Cambridge University Press, Cambridge, pp 47-69.
Farquhar et al. 1989b. Annual Review of Plant Physiology and Plant Molecular Biology. 40: 503-537.
Finnegan et al. 1998. Plant Molecular Biology 95: 5824-5829.
Freeman 1904. Philosophical Transactions of the Royal Society London (Biology) 196: 1-27.
Friend et al. 1962. Can J Bot, 40: 1299-1311.
Gan et al. 2004. Can. J Plant Sci, 84: 697-704.
Germida et al. 2010. Field-scale assessment of phytoremediation at a former oil tank battery in Bruderheim, Alberta. World Congress of Soil Science, Soil Solutions for a Changing World, 1-6 Aug. 2010. Brisbane, Australia. Available on-line at: http://www.iuss.org/19th%20WCSS/Symposium/pdf/0694.pdf
Gizinger 2002. Experimental Hematology, 30: 503-512.
Gornall et al. 2010. Phil. Trans. R. Soc. B, 365, 2973-2989.
Grant et al. 2009. Tree Physiology, 29: 1-17.
Gummerson 1986. J Exp Bot, 37: 729-741.
Gundel et al. 2010. Evol Appl, 3: 538-546.
Guo et al. 2003. Science, 302: 100-103.
Hayat et al. 2010. Nitric Oxide in Plant Physiology, Issue 58, Willey-VCH Verlag, Germany.
Hedden and Phillips, 2000. Trends in Plant Science, 5: 523-530.
Hubbard et al. 2011. In: Wheat: Genetics, Crops and Food Production. Nova Science Publishers Hauppauge, N.Y., USA. pp. 333-345.
Hubbard et al. 2012. Botany, 90(2): 137-149.
Jame et al. 1998. Agric Forest Meteorol 92: 241-249.
Ji et al., 2011. Plant Physiology, 156: 647-662.
Johannes et al. 2009. Plos Genetics 5: e1000530.
Johannes et al. 2011. Genetics, 188: 215-227.
Johnson et al. 1990. Crop Science, 30: 338-343.
Jost et al. 2001. Nucleic Acids Research, 29: 4452-4461.
Jumpponen and Trappe 1998. New Phytologist, 140: 295-310.
Jurado et al., 2010. Food Microbiology, 27: 50-57.
Kane 2011. Environmental and Experimental Botany, 71: 337-344.
Kang et al. 2008. International Journal of Sustainable Development and World Ecology, 15: 440-447.
Karavata & Manetas 1999. Photosynthetica, 36: 41-49.
Khan et al. 2010. Pakistan Journal of Botany, 42: 259-267.
Khan et al. 2012. BMC Microbiol, 12; 12:3.
Kiffer and Morelet 2000. Science Publisher Inc, Enfield, N.H., Plymouth.
Köchy and Tielbörger 2007. Basic Appl Ecol 8: 171-182.
Koyuncu 2005. Acta Biologica Cracoviensia Series Botanica, 47: 23-26.
Labeda et al 2012. Antonie van Leeuwenhoek, 101:73-104.
Lang-Mladek et al. 2010. Molecular Plant, 3: 594-602.
Larran et al. 2002. World Journal of Microbial Biotechnology, 18: 683-686.
Leone et al. 1994. Physiol Plantarum, 92: 21-30.
Li et al. 2008. Ecological Research, 23: 927-930.
Li et al. 2011. Agronomy Journal, 103: 1619-1628.
Lu et al. 2007. Plant Biology, 49: 1599-1607.
Lucht et al. 2002. Nature Genetics, 30: 311-314.
Madsood et al. 2005. Engineering Applications of Artificial Intelligence, 18: 115-125.
Margulis, 1991. In Symbiosis as a Source of Evolutionary Innovation, L. Margulis and R. Fester, ed. The MIT Press: Cambridge. pp. 1-14.
Marquez et al. 2007. Science, 315: 513-515.
McCormick M C, Siegel (eds.) 1999. Prenatal Care: Effectiveness and implementation. Cambridge University Press UK.
McDonald 2009. Handbook of biological statistics. 2nd ed. Sparky House Publishing, Baltimore, Md.
McMaster 2009. In: Carver B F (ed), *Wheat, science and trade*, Wiley-Blackwell, Iowa, USA, pp. 31-55.
Milberg and Andersson 1998. Plant Ecology, 134: 225-234.
Millar et al., 2006. Plant Journal, 45: 942-954.
Miransari et al. 2011. Applied Microbiology and Biotechnology, 92: 875-885.
Mitchell et al., 2009. Microbiology-SGM, 156: 270-277.
Mühlmann and Peintner 2000. Mycorrhiza, 18: 171-180.
Mukhopadhyay et al., 2004. PNAS, 101: 6309-6314.
Nakatsubo et al. 1998. FEBS Lett, 427:263-266.
Nakamura et al., 2010. Euphytica, 171: 111-120.
Nelson, 2004. Annu Rev Phytopathol, 42: 271-309.
Nicot 2005. Journal of Experimental Botany, 56: 2907-2914.
Nonogaki et al., 2010. Plant Science, 179: 574-581.
Oikawa et al., 2004. Plant Molecular Biology, 55: 687-700.
Okamoto et al., 2006. Plant Physiology, 141:97-107.
Oliver et al., 2007. Plant and Cell Physiology, 48: 1319-1330.
Penterman et al. 2007. PNAS, 104: 6752-6757.
Phillips et al., 1995. Plant Physiology, 108: 1049-1057.
Probert et al., 1989. Journal of Experimental Botany, 40: 293-301.
Qin and Zeevart, 1999. PNAS, 96: 15354-15361.
Reynolds et al. 2007 Journal of Experimental Botany, 58: 177-186.
Richards et al. 2002. Crop Science, 42: 111-121.
Ries et al. 2000. Nature, 406: 98-101.
Rivero et al. 2011. International Conference on *Arabidopsis* Research. June 22-25, Madison USA.
Ruan et al. 2002. Seed Sci Technol, 30: 61-67.
Ryan et al. 2008. FEMS Microbiol Lett, 278: 1-9.
Saikkonen et al., 1998. Annual Review of Ecology and Systematics, 29: 319-343.
Saze 2008. Seminars in Cell and Developmental Biology, 19: 527-536.
Schrey and Tarkka 2008. Antonie van Leeuwenhoek, 94:11-19.
Schutz and Rave 1999. Ecology, 144: 215-230.
Semenov and Shewry 2011. Scientific Reports, 1: 66-71.
Sinclair et al. 1984. BioScience, 34: 36-40.
Singh et al. 2011. Plant Signal Behav, 6: 175-191.
Smith and Read 2008. Mycorrhizal symbiosis, Third Edition. Elsevier Ltd. Mycorrhizas in acholorophyllous plants (mycoheterotrophs). Chapter 13: 458-507.
Solaiman et al. 2010. Australian Journal of Soil Research, 48: 546-554.
Soleimani et al. 2010. Chemosphere, 81: 1084-1090.
Stone et al., 2000. In: Bacon, C. W. and White, J. F. eds., Microbial Endophytes, Marcel Dekker New York Chap. 1: 3-29.
Strobel et al., 2004. Journal of Natural Products, 67: 257-268.
Sun et al. 2010. Journal of Plant Physiolog, 167: 1009-1017.
Tan and Zou, 2001. Nat Prod Rep, 18: 448-45.
Tokala et al. 2002. Appl Environ Microbiol, 68:2161-2171.
Vaughn et al. 2007. PloS Biology, 5: 1617-1629.
Verhoeven et al. 2010. New Phytologis, 185: 1108-1118.
Vujanovic et al. 2000. Annals of Botany, 86: 79-86.

Vujanovic and Brisson 2002. Mycological Progress. 1: 147-154.
Vujanovic and Vujanovic 2006. Floriculture, Ornamental and Plant Biotech, 63: 563-569.
Vujanovic and Vujanovic 2007. Symbiosis, 44: 93-99.
Vujanovic 2007b. Can J Plant Pathol, 29: 451-451.
Vujanovic 2008. 19th International Conference on *Arabidopsis*. Research Proceedings—ICAR13, July 23-27, Montreal, QC, Canada.
Waller et al. 2005. PNAS, 102: 13386-13391.
Wallin 1927. Symbionticism and the Origin of Species. London: Bailliere, Tindall and Cox.
Wang et al. 2011. Journal of Experimental Botany, 62: 1951-1960.
Whalley et al. 2006. Plant and Soil, 280: 279-290.
White and Torres 2010. Physiol. Plant, 138: 440-446.
Wu et al. 2008. Plant Physiology, 148: 1953-1963.
Wu and Sardo 2010. Lichtfouse E. (Ed.), Sociology, Organic Farming, Climate Change and Soil Science. Sustainable Agriculture Reviews. 3: DOI 10.1007/978-90-481-3333-8_3.
Yamaguchi et al. 1998. Plant Cell, 10: 2115-2126
Yang et al., 2002. Planta, 215: 645-652.
Zadoks et al. 1974. Weed Research, 14:415-421.
Zhang et al., 2007. BMC Genet, 2007, 8: 40.
Zhang et al. 2010. Journal of Cereal Science, 52: 263-269.
Zhang et al. 2011. African Journal of Microbiology Research, 5: 5540-5547.
Zhao et al. 2007. Journal of Plant Nutrition, 30: 947-963.
Zhong et al. 2009. African Journal of Biotechnology, 8: 6201-6207.
Zhu et al. 2007. Current Biology, 17: 54-59.
Foresight. The future of food and farming: challenges and choices for global sustainability. Final Project Report. London: The Government Office for Science, U K, 2011.
IPCC Climate Change 2007. In: Solomon S, Qin D, Manning M, Chen Z, Marquis M, Averyt K B, Tignor M and Miller H L (Eds). Cambridge University Press, Cambridge, UK.
Saskatchewan Ministry of Agriculture 2008. Varieties of Grain Crops. SaskSeed guide. Regina, SK, Canada

---

The invention claimed is:

1. A plant seed manually or mechanically coated with at least one endophyte, wherein the plant is a cereal that is not wheat and the endophyte is a *Streptomyces* sp. strain or culture thereof which is deposited under IDAC 081111-06 or which comprises the 16S rDNA sequence as shown in SEQ ID NO:6.

2. The coated plant seed of claim 1, wherein the plant is a barley plant.

3. A method of improving seed vitality, plant health and/or yield comprising cultivating the coated plant seed of claim 1 into a first generation plant.

4. The method of claim 3, wherein the plant is a barley plant.

5. The method of claim 3, wherein the improving seed vitality, plant health, and/or yield is for increasing seed germination, for decreasing time to reach the energy of germination, for reducing hydrothermal time required for germination, for increasing seed germination vigour, for increasing the fresh weight of seedlings, for enhancing *Rhizobium* nodulation traits, for increasing yield of seedlings, for reducing the effects of stress on the seed or cultivated plant, for reducing the effects of drought, heat and/or biotic stress on the seed or cultivated plant, for reducing a Fusarium infection on the seed or cultivated plant, for enhancing stratification, for breaking dormancy, for reducing the effects of stress by modulating gene expression of hormonal ent-kaurenoic (KAO), for repression of shoot growth (RSG), abscisic acid (ABA), gibberellic acid (GA), 14-3-3 genes and nitric oxide (NO) molecules, and/or for modulating gene expression of stress resistance superoxide dismutase (SOD), manganese SOD (MnSOD), proline (Pro) or MYB genes.

6. The method of claim 5, wherein the plant is a barley plant.

7. A method of improving plant health and/or yield comprising manually or mechanically coating a plant seed with at least one endophyte, wherein the plant is a cereal that is not wheat and the endophyte is a *Streptomyces* sp. strain or culture thereof which is deposited under IDAC 081111-06 or which comprises the 16S rDNA sequence as shown in SEQ ID NO:6; and cultivating the coated plant seed into a first generation plant.

8. The method of claim 7, wherein the plant is a barley plant.

9. The method of claim 7, wherein the improving plant health and/or yield is for reducing the effects of stress.

10. The method of claim 9, wherein the plant is a barley plant.

11. The method of claim 7, wherein the improving plant health and/or yield is for reducing the effects of stress wherein the stress is heat, drought or biotic stress.

12. The method of claim 11, wherein the plant is a barley plant.

13. A method of phytoremediation or phytoreclamation of a contaminated site comprising cultivating the coated plant seed of claim 1 on the site into a first generation plant; thereby remediating or reclaiming the site.

14. The method of claim 13, wherein the plant is a barley plant.

15. The method of claim 13, wherein the site is contaminated with an organic chemical, a salt or a metal.

16. The method of claim 13, wherein the site is contaminated with an organic chemical and the organic chemical is a hydrocarbon or a petroleum.

17. The method of claim 13, wherein the site is contaminated with metal and the metal is lead or cadmium and/or a radioisotope.

18. The plant seed of claim 1, wherein the endophyte is the *Streptomyces* sp. strain or culture thereof which is deposited under IDAC 081111-06 and the plant is a barley plant.

19. A method of improving seed vitality, plant health and/or yield comprising cultivating the coated plant seed of claim 18 into a first generation plant.

20. The method of improving plant health and/or yield of claim 7, wherein the plant seed is a barley plant seed and the endophyte is a *Streptomyces* sp. strain or culture thereof which is deposited under IDAC 081111-06.

* * * * *